United States Patent
Mudd, Jr. et al.

(10) Patent No.: US 12,357,636 B2
(45) Date of Patent: Jul. 15, 2025

(54) VIBEGRON FOR THE TREATMENT OF OVERACTIVE BLADDER SYMPTOMS

(71) Applicant: Urovant Sciences GmbH, Basel (CH)

(72) Inventors: Paul N. Mudd, Jr., Cary, NC (US); Cornelia Haag-Molkenteller, Irvine, CA (US); Jihao Zhou, Rancho Santa Margarita, CA (US)

(73) Assignee: Urovant Sciences GmbH, Basel (CH)

( * ) Notice: Subject to any disclaimer, the term of this patent is extended or adjusted under 35 U.S.C. 154(b) by 881 days.

(21) Appl. No.: 17/311,239

(22) PCT Filed: Dec. 5, 2019

(86) PCT No.: PCT/IB2019/060490
§ 371 (c)(1),
(2) Date: Jun. 4, 2021

(87) PCT Pub. No.: WO2020/115705
PCT Pub. Date: Jun. 11, 2020

(65) Prior Publication Data

US 2022/0117971 A1    Apr. 21, 2022

Related U.S. Application Data

(60) Provisional application No. 62/842,418, filed on May 2, 2019, provisional application No. 62/830,298, filed on Apr. 5, 2019, provisional application No. 62/775,818, filed on Dec. 5, 2018.

(51) Int. Cl.
*A61K 31/519* (2006.01)
*A61K 9/00* (2006.01)
*A61P 13/10* (2006.01)

(52) U.S. Cl.
CPC .......... *A61K 31/519* (2013.01); *A61K 9/0053* (2013.01); *A61P 13/10* (2018.01)

(58) Field of Classification Search
CPC ...... A61K 31/519; A61K 9/0053; A61P 13/10
See application file for complete search history.

(56) References Cited

U.S. PATENT DOCUMENTS

| | | |
|---|---|---|
| 6,251,925 B1 | 6/2001 | Donaldson et al. |
| 6,346,532 B1 | 2/2002 | Maruyama et al. |
| 6,525,202 B2 | 2/2003 | Hu et al. |
| 6,562,375 B1 | 5/2003 | Sako et al. |
| 7,342,117 B2 | 3/2008 | Kawazoe et al. |
| 7,396,958 B2 | 7/2008 | Courtemanche et al. |
| 7,982,049 B2 | 7/2011 | Kawazoe et al. |
| 8,247,415 B2 | 8/2012 | Berger et al. |
| 8,399,480 B2 | 3/2013 | Berger et al. |
| 8,415,126 B2 | 4/2013 | Mundorff et al. |
| 8,642,661 B2 | 2/2014 | Caltabiano et al. |
| 8,653,260 B2 | 2/2014 | Berger et al. |
| RE44,872 E | 4/2014 | Takasu et al. |
| 8,748,143 B2 | 6/2014 | Liang et al. |
| 8,748,433 B2 | 6/2014 | Berger et al. |
| 8,772,315 B2 | 7/2014 | Suzuki et al. |
| 8,835,474 B2 | 9/2014 | Takasu et al. |
| 9,522,129 B2 | 12/2016 | Caltabiano et al. |
| 9,809,536 B2 | 11/2017 | Chung et al. |
| 9,822,121 B2 | 11/2017 | Chung et al. |
| 9,907,767 B2 | 3/2018 | Caltabiano et al. |
| 9,956,194 B2 | 5/2018 | Ohlstein et al. |
| 10,065,922 B2 | 9/2018 | Stevens et al. |
| 10,087,189 B2 | 10/2018 | Chung et al. |
| 10,287,289 B2 | 5/2019 | Xu et al. |
| 10,350,182 B2 | 7/2019 | Caltabiano et al. |
| 10,435,410 B2 | 10/2019 | Chung et al. |
| 10,577,316 B2 | 3/2020 | Chung et al. |
| 10,696,681 B2 | 6/2020 | Xu et al. |
| 10,899,771 B2 | 1/2021 | Chung et al. |
| 11,091,493 B2 | 8/2021 | Xu et al. |
| 11,124,478 B2 | 9/2021 | Chung et al. |
| 11,649,243 B2 | 5/2023 | Xu et al. |
| 11,708,371 B2 | 7/2023 | Chung et al. |
| 11,767,292 B2 | 9/2023 | Chung et al. |
| 12,102,638 B2 | 10/2024 | Piscitelli et al. |
| 12,180,219 B2 | 12/2024 | Xu et al. |
| 2012/0202819 A1 | 8/2012 | Edmondson et al. |
| 2014/0242645 A1 | 8/2014 | Chung et al. |

(Continued)

FOREIGN PATENT DOCUMENTS

| | | | |
|---|---|---|---|
| JP | 6197971 B1 | | 9/2017 |
| WO | WO-2003072572 A1 | | 9/2003 |

(Continued)

OTHER PUBLICATIONS

Yoshida et al. Vibegron, a Novel Potent and Selective b3-Adrenoreceptor Agonist, for the Treatment of Patients with Overactive Bladder: A Randomized, Double-blind, Placebo-controlled Phase 3 Study, European Urology 73 (2018) pp. 783-790 (Year: 2018).*

Lee et al. Current role of treatment in men with lower urinary tract symptoms combined with overactive bladder, Prostate International, Apr. 2014, pp. 43-49. (Year: 2014).*

Otsuki et al. Î²3-Adrenoceptor agonist mirabegron is effective for overactive bladder that is unresponsive to antimuscarinic treatment or is related to benign prostatic hyperplasia in men, Internationally Urology and Nephroogy, Dec. 2012, pp. 53-60 (Year: 2012).*

Menghua, C. et al., "Research Progress of Therapeutic Drugs for Lower Urinary Tract Symptoms," Guangdong Chemical Industry, 2016, 43 (11), 107-109.

(Continued)

*Primary Examiner* — Sarah Pihonak
*Assistant Examiner* — Mikhail O'Donnel Robinson
(74) *Attorney, Agent, or Firm* — Sterne, Kessler Goldstein & Fox P.L.L.C.

(57) ABSTRACT

The present disclosure is directed to a method of treating overactive bladder symptoms in men with benign prostatic hyperplasia comprising orally administering to a subject in need thereof an amount of from about 60 mg to about 90 mg (e.g., about 75 mg) of vibegron per day.

29 Claims, 2 Drawing Sheets

(56) References Cited

U.S. PATENT DOCUMENTS

| | | | |
|---|---|---|---|
| 2015/0087832 | A1 | 3/2015 | Chung et al. |
| 2016/0031903 | A1 | 2/2016 | Nakai et al. |
| 2016/0176884 | A1 | 6/2016 | Chung et al. |
| 2016/0361380 | A1* | 12/2016 | Averback ............... A61K 38/10 |
| 2017/0035716 | A1 | 2/2017 | Ohstein et al. |
| 2017/0145014 | A1 | 5/2017 | Xu et al. |
| 2017/0348263 | A1 | 12/2017 | Ohlstein et al. |
| 2017/0348288 | A1* | 12/2017 | Ohlstein ............. A61K 31/445 |
| 2018/0147169 | A1 | 5/2018 | Caltabiano et al. |
| 2019/0083433 | A1 | 3/2019 | Ohlstein et al. |
| 2019/0083434 | A1 | 3/2019 | Ohlstein et al. |
| 2020/0392141 | A1 | 12/2020 | Xu et al. |
| 2021/0077495 | A1 | 3/2021 | Piscitelli et al. |
| 2021/0077496 | A1 | 3/2021 | Piscitelli et al. |
| 2021/0196720 | A1 | 7/2021 | Mudd et al. |
| 2021/0221815 | A1 | 7/2021 | Chung et al. |
| 2022/0073459 | A1 | 3/2022 | Chung et al. |
| 2022/0073523 | A1 | 3/2022 | Xu et al. |
| 2023/0027066 | A1 | 1/2023 | Mudd et al. |
| 2023/0218624 | A1 | 7/2023 | Piscitelli et al. |
| 2024/0050457 | A1 | 2/2024 | Mudd |
| 2024/0148735 | A1 | 5/2024 | Zhou |

FOREIGN PATENT DOCUMENTS

| | | | | |
|---|---|---|---|---|
| WO | WO-2009124166 | A1 | 10/2009 | |
| WO | WO-2009124167 | A1 * | 10/2009 | ........... A61K 31/428 |
| WO | WO2010020882 | A1 | 2/2010 | |
| WO | WO-2011043942 | A1 | 4/2011 | |
| WO | WO-2013062878 | A1 | 5/2013 | |
| WO | WO-2013062881 | A1 | 5/2013 | |
| WO | WO-2013074650 | A1 | 5/2013 | |
| WO | WO-2014150639 | A1 | 9/2014 | |
| WO | WO-2017070689 | A2 | 4/2017 | |
| WO | WO-2017210696 | A1 | 12/2017 | |
| WO | WO-2018224989 | A1 | 12/2018 | |
| WO | WO-2018224990 | A1 | 12/2018 | |
| WO | WO-2019124507 | A1 | 6/2019 | |
| WO | WO-2019224788 | A1 | 11/2019 | |
| WO | WO-2020188505 | A1 | 9/2020 | |

OTHER PUBLICATIONS

Wei, M., et al., "A Beta-3 Adrenergic Agonist to Treat Bladder Hyperactive Disorder: Vibegron," Modern Drugs & Clinic, Feb. 2017. 32(2), 347-350.

Search Report for CN Application No. 2019800805919, Jun. 22, 2024, 8 pages.

Yoshida, M. et al., "Efficacy of novel b3-adrenoreceptor agonist vibegron on nocturia in patients with overactive bladder: A post-hoc analysis of a randomized, double-blind, placebo-controlled phase 3 study," *Int. J. Urology* (2019) 26, 369-375.

Ichihara, K. et al., "A Randomized Controlled Study of the Efficacy of Tamsulosin Monotherapy and its Combination with Mirabegron for Overactive Bladder Induced by Benign Prostatic Obstruction," *J. Urology* (2015) 193, 921-926.

Herschron, S. et al., "Mirabegron Vs Placebo Add-on Therapy in Men With Overactive Bladder Symptoms Receiving Tamsulosin for Underlying Benign Prostatic Hyperplasia: A Safety Analysis From the Randomized, Phase 4 PLUS Study," *Urology* (2021) 147, 235-242. Available at https://doi.org/10.1016/j.urology.2020.09.040.

Kaplan, S. A. et al., "Efficacy and Safety of Mirabegron versus Placebo Add-On Therapy in Men with Overactive Bladder Symptoms Receiving Tamsulosin for Underlying Benign Prostatic Hyperplasia: A Randomized, Phase 4 Study (PLUS)," *J. of Urology* (2020) 203, 1163-1171.

Wu, Y. et al., "Mirabegron add-on tamsulosin for men with overactive bladder symptoms: a pooled analysis of four randomized controlled trials," *Urologica Internationalis* (2024) DOI: 10.1159/000536110.

Staskin, D. et al., "International Phase III, Randomized, Double-Blind, Placebo and Active Controlled Study to Evaluate the Safety and Efficacy of Vibegron in Patients with Symptoms of Overactive Bladder: Empowur," *J. of Urology* (2020) 204,316-324.

ClinicalTrials.gov Protocol Registration Preview for RVT-901-3004 (An Extension Study to Examine the Safety and Tolerability of a New Drug in Patients With Symptoms of Overactive Bladder (OAB) Empowur); Indicating first posted Jul. 11, 2018.

ClinicalTrials.gov Protocol Registration Preview for URO-901-3005 (Study to Evaluate the Efficacy, Safety and Tolerability of Vibegron in Men With Overactive Bladder (OAB) Symptoms on Pharmacological Therapy for Benign Prostatic Hyperplasia (BPH); Indicating first posted Apr. 3, 2019.

ClinicalTrials.gov Protocol Registration Preview for URO-901-3006 (Extension Study of Vibegron in Men With Overactive Bladder (OAB) Symptoms on Pharmacological Therapy for Benign Prostatic Hyperplasia (BPH)); Indicating first posted Sep. 25, 2019.

Co-pending U.S. Appl. No. 18/317,417, First Inventor, Xu, F. filed May 15, 2023 (Not Published).

Co-pending U.S. Appl. No. 18/508,594, First Inventor, Xu, F. filed Nov. 14, 2023 (Not Published).

Co-pending U.S. Appl. No. 18/258,953, Inventor, Mudd, P.N. filed Dec. 22, 2021 (Not Published).

Co-pending U.S. Appl. No. 18/546,585, Inventor, Zhou, J.. filed Feb. 16, 2022 (Not Published).

International Preliminary Report on Patentability and Written Opinion for International Application No. PCT/US2014/023858, The International Bureau of WIPO, Geneva, Switzerland, issued on Sep. 15, 2015, 5 pages.

International Search Report for International Application No. PCT/US2014/023858, United States Patent and Trademark Office, mailed on Jun. 6, 2014, 4 pages.

International Search Report and Written Opinion for International Application No. PCT/IB2020/052484, European Patent Office, Rijswijk, Netherlands issued on Jun. 26, 2020, 13 pages.

International Search Report and Written Opinion for International Application No. PCT/IB2021/062208, European Patent Office, Rijswijk, Netherlands issued on Mar. 9, 2022, 15 pages.

Xu, F., et al., "Asymmetric synthesis of cis-2,5-disubstituted pyrrolidine, the core scaffold of β3-AR agonists," *Organic Letters* 15(6):1342-1345, American Chemical Society, United States (Mar. 2013).

International Preliminary Report on Patentability and Written Opinion for International Application No. PCT/US2009/039249, the International Bureau of WIPO, Geneva, Switzerland, issued on Oct. 5, 2010, 6 pages.

International Preliminary Report on Patentability and Written Opinion for International Application No. PCT/US2009/039253 the International Bureau of WIPO, Geneva, Switzerland, issued on Oct. 5, 2010, 5 pages.

International Search Report for International Application No. PCT/US2009/039249, European Patent Office, Netherlands, mailed on Aug. 31, 2009, 4 pages.

International Search Report for International Application No. PCT/US2009/039253, European Patent Office, Netherlands, mailed on Jun. 17, 2009, 3 pages.

Morriello, G. J., "Design of a novel pyrrolidine scaffold utilized in the discovery of potent and selective human β3 adrenergic receptor agonists," *Bioorganic & Medicinal Chemistry Letters* 21(6):1865-1870, Elsevier, Netherlands (Mar. 2011).

International Preliminary Report on Patentability and Written Opinion for International Application No. PCT/IB2018/054069, the International Bureau of WIPO, Geneva, Switzerland, issued on Dec. 10, 2019, 7 pages.

International Preliminary Report on Patentability and Written Opinion for International Application No. PCT/IB2018/054070, the International Bureau of WIPO, Geneva, Switzerland, issued on Dec. 10, 2019, 7 pages.

Yoshida, M., et al., "1082—Vibegron, a novel potent and selective β3-adrenoreceptor agonist, for the treatment of patients with overactive bladder: A randomized, double-blind, placebo-controlled phase 3 study," *European Urology Supplements* 17(2):E1531-E1532, Elsevier, Netherlands (Mar. 2018).

(56) References Cited

OTHER PUBLICATIONS

Mitcheson, D., et al., "Once Daily Vibegron Improves Quality of Life Measures in Patients with Overactive Bladder," *Value in Health* 21(Suppl 1):S267-S268, Elsevier Inc., United States (May 2018).
International Search Report for International Application No. PCT/IB2018/054069, European Patent Office, NL, mailed on Sep. 24, 2018, 3 pages.
ClinicalTrials.gov Protocol Registration Preview for MK-4618-008 CSP (A Study of the Efficacy and Safety of Vibegron (MK-4618) in Participants with Overactive Bladder (OAB); Indicating first posted Mar. 15, 2011.
ClinicalTrials.gov Protocol Registration Preview for MK-4618-004 CSP (A Study of the Pharmacokinetics and Pharmacodynamics of Vibegron (MK-4618) in Women With Overactive Bladder; Indicating first posted Dec. 28, 2011.
ClinicalTrials.gov Protocol Registration Preview for MK-4618-014 CSP (Single-Dose Study of the Pharmacokinetics of Vibegron (MK-4618) in Participants with Renal Insufficiency; Indicating first posted Jun. 26, 2012.
ClinicalTrials.gov Protocol Registration Preview for MK-4618-013 CSP (Single-Dose Study of the Pharmacokinetics of Vibegron (MK-4618) in Adults with Hepatic Insufficiency; Indicating first posted Nov. 29, 2012.
ClinicalTrials.gov Protocol Registration Preview for RVT-901-3003 (An International Phase 3, Randomized, Double-Blind, Placebo- and Active (Tolterodine)-Controlled Multicenter Study to Evaluate the Safety and Efficacy of Vibegron in Patients with Symptoms of Overactive Bladder); Indicating first posted Apr. 10, 2018.
Yoshida, M., et al., "Vibegron, a Novel Potent and Selective β 3-Adrenoreceptor Agonist, for the Treatment of Patients with Overactive Bladder: A Randomized, Double-blind, Placebo-controlled Phase 3 Study," *European Urology* 73(5):783-790, Elsevier, Netherlands (May 2018).
Yoshida, M., et al., "Long-Term Safety and Efficacy of the Novel β3-Adrenoreceptor Agonist Vibegron in Japanese Patients with Overactive Bladder: A Phase III Prospective Study," *Int J Urol* 25(7):668-675, Wiley, United States (Jul. 2018).
Edmondson, S. D. et al., "Discovery of Vibegron: A Potent and Selective β3 Adrenergic Receptor Agonist for the Treatment of Overactive Bladder," *Journal of Medicinal Chemistry* 59(2):609-623, American Chemical Society, United States (Jan. 2016).
Edmondson, S. D., et. al., "Discovery and Early Development of Vibegron (MK-4618) : A Potent and Selective β3-AR Agonist for the Treatment of Overactive Bladder," Abstracts of Papers, 249$^{th}$ ACS Natl. Mtg. & Expo. Denver, CO, United States (Mar. 22-26, 2015).
Giarenis, I., et al., "Overactive Bladder and the β3-Adrenoceptor Agonists: Current Strategy and Future Prospects," Drugs 75(15):1707-1713, Springer, United States (Oct. 2015).
Zhu, C., et al., "Discovery of benzamides as potent human β3 adrenergic receptor agonists," *Bioorganic and Medicinal Chemistry Letters* 26(1):55-59, Elsevier, Netherlands (Jan. 2016).
Perabo, F. G. E. et al., "Drug development for LUTS—The challenge for industry," *Drug Discovery Today: Therapeutic Strategies* 9(1):E5-E14, Portal Komunikacji Naukowej, Poland (Spring 2012).
Polland, A., et al., "Emerging treatments for urinary incontinence," *Expert Opinion Emerg Drugs* 19(2):281-290, Informa PLC, United Kingdom (Jun. 2014).
International Search Report for International Application No. PCT/US2010/50328, United States Patent Office, mailed on Nov. 18, 2010, 2 pages.
International Preliminary Report on Patentability and Written Opinion for International Application No. PCT/US2010/050328, the International Bureau of WIPO, Geneva, Switzerland, issued Apr. 11, 2012, 7 pages.
International Preliminary Report on Patentability and Written Opinion for International Application No. PCT/US2012/061252, the International Bureau of WIPO, Geneva, Switzerland, issued Apr. 29, 2014, 4 pages.

International Search Report for International Application No. PCT/IB2018/054070, European Patent Office, NL, mailed on Sep. 24, 2018, 3 pages.
Abrams, P., "Describing bladder storage function: overactive bladder syndrome and detrusor overactivity," *Urology* 62(Supplement 5B):28-37, 40-42, Elsevier, Netherlands (Nov. 2003).
Abrams, P., et al., "The standardisation of terminology in lower urinary tract function: report from the standardisation subcommittee of the International Continence Society," *Urology* 61(1):37-49, Elsevier, Netherlands (Jan. 2003).
American Urological Association, "Management of Benign Prostatic Hyperplasia," available at accessed at URL:[https://web.archive.org/web/20190216022522/https://www.auanet.org/benign-prostatic-hyperplasia-(2010-reviewed- and-validity-confirmed-2014)] on Jan. 25, 2022, 19 pages (2010).
Chapple, C. R., et al., "Terminology report from the International Continence Society (ICS) Working Group on Underactive Bladder (UAB)," *Neurology and Urodynamics* 37(8):2928-2931, Wiley, United States (Nov. 2018).
Hashim, H., et al., "International Continence Society (ICS) report on the terminology for nocturia and nocturnal lower urinary tract function," *Neurology and Urodynamics* 38(2):499-508, Wiley, United States (Feb. 2019).
International Search Report and Written Opinion for International Application No. PCT/IB2019/060490, European Patent Office, Netherlands, mailed on Mar. 9, 2020, 11 pages.
Kitta, T., et al., "Benefits and limitations of animal models in partial bladder outlet obstruction for translational research," *Int J Urol* 25(1):36-44, Wiley, United States (Jan. 2018).
Otsuki, H., et al., "β3-Adrenoceptor agonist mirabegron is effective for overactive bladder that is unresponsive to antimuscarinic treatment or is related to benign prostatic hyperplasia in men," *Int Urol Nephrol* 45(1):53-60, Springer, United States (Feb. 2013).
Painter, C. E., and Suskind, A. M., "Advances in pharmacotherapy for the treatment of overactive bladder," *Curr Bladder Dysfunct Rep* 14(4):377-384, Springer, United States (Nov. 2019).
Rabin, R., et al., "From translation to version management: a history and review of methods for the cultural adaptation of the EuroQol five-dimensional questionnaire," *Value in Health* 17(1):70-76, Elsevier, Netherlands (Jan.-Feb. 2014).
Tubaro, A. et al., "Efficacy and Safety of Daily Mirabegron 50 mg in Male Patients with Overactive Bladder: A Critical Analysis of Five Phase III Studies," *Therapeutic Advances in Urology*, 2017, vol. 9(6) 137-154.
Russo, A. "Latest Pharmacotherapy Options for Benign Prostatic Hyperplasia," *Expert Opinion*, (2014) 15(16): 2319-2328.
Suarez, O., "Mirabegron for Male Lower Urinary Tract Symptoms," *Curr. Urol. Rep.* (2013) 14:580-584.
Yoshida, M., et al., "Vibegron, a Novel Potent and Selective β 3-Adrenoreceptor Agonist, for the Treatment of Patients with Overactive Bladder: A Randomized, Double-blind, Placebo-controlled Phase 3 Study," *European Urology* 73(5):783-790 (Supplementary Data), Elsevier, Netherlands (May 2018).
Badlani, G., "Overactive Bladder: Advancement or More of the Same," *European Urology* 73(5): 791-792 (Editorial) (Supplementary Data), Elsevier, Netherlands (May 2018).
Co-pending U.S. Appl. No. 18/761,169, First Inventor, Piscitelli, S. filed Jul. 1, 2024 (Not Published).
Co-pending U.S. Appl. No. 18/649,712, First Inventor, Xu, F. filed Apr. 29, 2024 (Not Published).
Gomelsky, A., "Overactive bladder in males," *Therapeutic Advances in Urology*, 2009, 1(4) 209-221.
International Search Report for International Application No. PCT/US2012/061249, United States Patent Office, mailed on Dec. 28, 2012, 2 pages.
International Preliminary Report on Patentability and Written Opinion for International Application No. PCT/US2012/061249, United States Patent Office, mailed on Dec. 28, 2012, 3 pages.
International Search Report and Written Opinion for International Application No. PCT/IB2022/051393, European Patent Office, Netherlands, mailed on May 20, 2022, 15 pages.
Yoshida, M., et al., "Vibegron, a Novel Potent and Selective β 3-Adrenoreceptor Agonist, for the Treatment of Patients with Over-

(56) References Cited

OTHER PUBLICATIONS active Bladder: A Randomized, Double-blind, Placebo-controlled Phase 3 Study," European Urology 73(5) Supplementary Data 1-10, Elsevier, Netherlands (May 2018).

Co-pending U.S. Appl. No. 19/003,660, inventors Xu, F., et al., filed Dec. 27, 2024 (Not yet Published).

Co-pending U.S. Appl. No. 18/951,194, inventors Piscitelli, S., et al., filed Nov. 18, 2024 (Not yet Published).

* cited by examiner

VIBEGRON FOR THE TREATMENT OF OVERACTIVE BLADDER SYMPTOMS

CROSS REFERENCE TO RELATED APPLICATIONS

The present application is a U.S. National Phase application under 35 U.S.C. § 371 of International Application No. PCT/IB2019/060490, filed Dec. 5, 2019, which claims priority to U.S. Provisional Patent Application No. 62/842,418, filed May 2, 2019; to U.S. Provisional Patent Application No. 62/830,298, filed Apr. 5, 2019; and to U.S. Provisional Patent Application No. 62/775,818, filed Dec. 5, 2018; which applications are incorporated by reference herein in their entirety.

BACKGROUND

Benign prostatic hyperplasia (BPH) is a condition characterized by the benign growth and/or changes in the prostate gland due to proliferation of smooth muscle and epithelial cells within the prostatic transition zone. Historically in men with BPH, lower urinary tract symptoms (LUTS) have been presumed to result from bladder outlet obstruction secondary to prostate enlargement. However, men may have overactive bladder (OAB) symptoms in the absence of, or in conjunction with voiding and/or storage symptoms associated with BPH. BPH can be associated with debilitating LUTS, categorized by storage symptoms (e.g., urinary frequency, urgency, and nocturia) and voiding dysfunction (e.g., decreased and intermittent force of stream and the sensation of incomplete bladder emptying).

Overactive bladder (OAB) is a chronic and often debilitating condition of the lower urinary tract affecting both males and females. The function of the lower urinary tract is to store and periodically release urine. This requires the orchestration of storage and micturition reflexes. Storage and micturition reflexes involve a variety of afferent and efferent neural pathways, leading to modulation of central and peripheral neuroeffector mechanisms, and resultant coordinated regulation of sympathetic and parasympathetic components of the autonomic nervous system, as well as somatic motor pathways. These proximally regulate the contractile state of bladder (detrusor) and urethral smooth muscle, and urethral sphincter striated muscle.

Overactive bladder, from a pathophysiologic perspective, has been possibly linked with detrusor overactivity. OAB is characterized by the symptoms of urinary urgency, with or without urgency urinary incontinence, usually associated with frequency and nocturia in the absence of urinary tract infection or other obvious pathology. The prevalence of OAB in the United States and Europe has been estimated at 16 to 17% in both women and men over the age of 18 years. Overactive bladder is most often classified as idiopathic, but can also be secondary to a neurological condition, bladder outlet obstruction, and other causes.

Initial pharmacologic therapy for OAB symptoms in men with BPH traditionally has been directed at minimizing the obstruction, and has included α1-adrenergic receptor antagonists to relax the muscles of the prostate and bladder neck or 5α-reductase inhibitors to reduce prostate growth. While patients may see some improvement in LUTS with these BPH therapies (e.g., improvement in urinary flow), control for OAB symptoms is incomplete and, for many, urinary urgency, incontinence, frequency, or nocturia persists. To address persistent OAB symptoms in men with BPH, combinations of BPH therapies with OAB medications, such as anticholinergics, have shown promise. However, the clinical use of anticholinergics is limited by mechanism-based side effects including dry mouth, constipation, increased risk of urinary retention, and the potential for CNS adverse effects. Further, contraindications and precautions exist due to the possibility of urinary retention.

Beta-3 adrenergic receptor ($\beta_3$-AR) activation is an effective way of relaxing the detrusor in normal and pathogenic states. Functional evidence in support of an important role for the $\beta_3$-AR in urine storage emanates from studies in vivo. $\beta_3$-AR agonists have demonstrated efficacy in alleviating symptoms of OAB. To date, only one $\beta_3$-AR agonist, mirabegron (Astellas Pharma Global Development, Inc), has received marketing approval in both the US and Japan for the treatment of OAB. Mirabegron activates the $\beta_3$-AR in the detrusor muscle in the bladder, which leads to muscle relaxation and an increase in bladder capacity. Reductions in micturition frequency, urinary incontinence and urgency episodes, and increases in mean volume voided per micturition were observed with mirabegron. See, e.g., Otsuki et al., *Int Urol Nephrol.* 45(1):53-60 (2013).

Vibegron, (6S)—N-[4-[[(2S,5R)-5-[(R)-hydroxy(phenyl)methyl]pyrrolidin-2-yl]methyl]phenyl]-4-oxo-7,8-dihydro-6H-pyrrolo[1,2-a]pyrimidine-6-carboxamide, is a potent and highly selective beta-3 adrenergic receptor ($\beta_3$-AR) agonist demonstrating >9,000 fold selectivity for activation of $\beta_3$-AR over $\beta_2$-AR and $\beta_1$-AR in cell based in vitro assays. See Edmondson et al., J. Med. Chem. 59:609-623 (2016). Vibegron was also studied in a Phase 3 clinical trial for treating patients with overactive bladder (OAB). See Yoshida et al., European Urology 73:783-790 (2018).

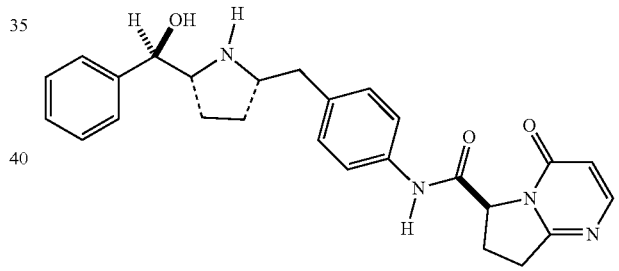

Vibegron is disclosed as a $\beta_3$-AR agonist in U.S. Pat. Nos. 8,399,480 and 8,247,415. Synthetic methods for preparing vibegron are disclosed in United States Publication Nos. US 2017/0145014, US 2015/0087832, US 2016/0176884 and US 2014/0242645. All of the cited publications are herein incorporated by reference in their entireties.

There is a need to develop novel methods for treating overactive bladder symptoms in men with BPH.

SUMMARY

Figure 1:
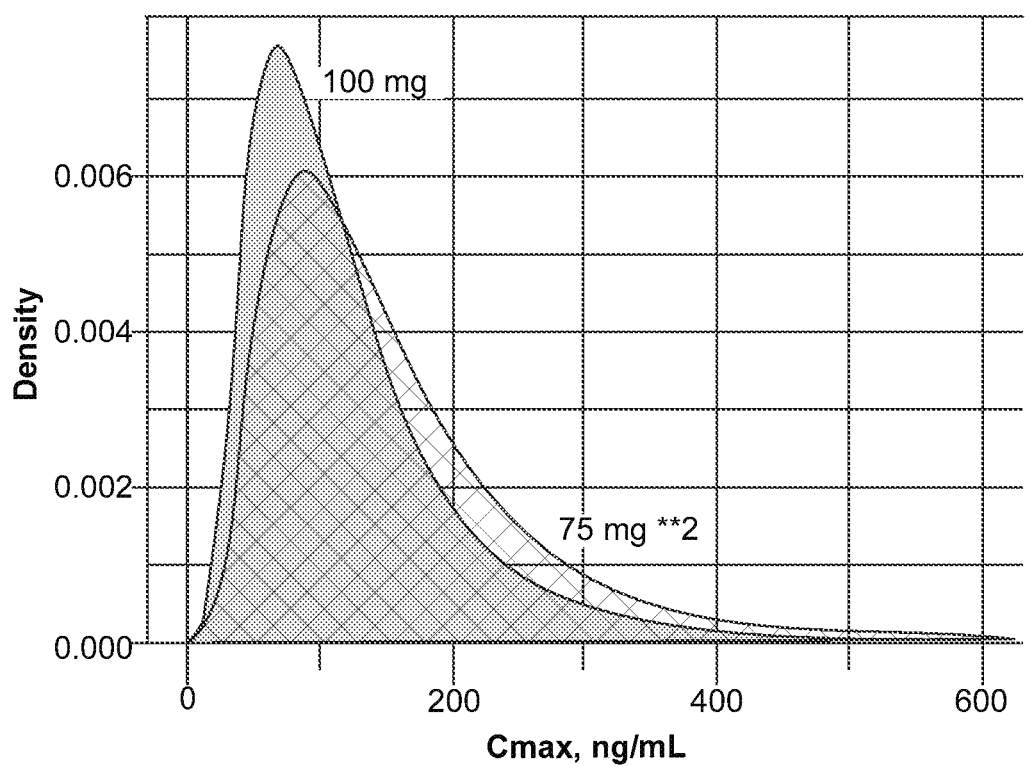
FIG. 1 depicts an overlay of density plots of exposure with vibegron 100 mg and 75 mg, as estimated in special populations.

The present disclosure provides a method of treating overactive bladder symptoms in a subject with benign prostatic hyperplasia, the method comprising orally administering to a subject in need thereof an amount of from 60 mg to 90 mg of vibegron per day.

DETAILED DESCRIPTION

In order that the present disclosure can be more readily understood, certain terms are first defined. As used in this application, except as otherwise expressly provided herein, each of the following terms shall have the meaning set forth below. Additional definitions are set forth throughout the application.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related.

The term "about" as used in connection with a numerical value throughout the specification and the claims denotes an interval of accuracy, familiar and acceptable to a person skilled in the art. Such interval of accuracy is ±10%.

The term "nocturia" as used herein refers to the number of times urine is passed during the main sleep period. According to the International Continence Society, when having woken to pass urine for the first time, each urination must be followed by sleep or the intention to sleep, which is quantified using a bladder diary. In some aspects, nocturia includes a complaint of interruption of sleep one or more times because of the need to micturate. In some aspects, each void may or may not be preceded and followed by sleep. (See Hashim, H. et al., "International Continence Society (ICS) Report on the Terminology for Nocturia and Nocturnal Lower Urinary Tract Function," *Neurology and Urodynamics* 2019, 1-10.

The term "overactive bladder" generally refers to a clinical syndrome characterized by urinary urgency, which can be accompanied by frequency and nocturia, with or without urge incontinence, in the absence of urinary tract infection or other obvious pathology. The term "overactive bladder" is defined by the International Continence Society (ICS) as follows: Overactive bladder (OAB) is a symptom complex consisting of urgency with or without urge incontinence, usually with frequency and nocturia, in the absence of local pathologic or hormonal factors (Abrams P et al., Urology 2003, 61(1): 37-49; Abrams P et al., Urology 2003, 62 (Supplement 5B): 28-37 and 40-42). Synonyms of overactive bladder (OAB) include "urge syndrome" and "urge frequency syndrome."

The term "urgency urinary incontinence" (UUI) as used herein refers to a complaint of involuntary loss of urine associated with urgency and can be used interchangeably with "urge urinary incontinence." UUI is distinguished from stress urinary incontinence, which is the involuntary loss of urine on effort or physical exertion (e.g., sporting activities), or on sneezing or coughing. "Urge incontinence" refers to complaint of involuntary loss of urine.

The term "impairment" as used herein means acute or chronic reduction in function. For example, renal impairment refers to a medical condition where the kidneys fail to maintain their normal function, so that waste products and metabolites accumulate in the blood.

The term "urinary urgency" as used herein refers to a complaint of a sudden compelling desire to urinate which is difficult to defer.

The term "urinary frequency" as used herein refers to a complaint by the patient who considers that he/she experiences too many micturitions by day.

The term "benign prostatic hyperplasia" is a histologic diagnosis that refers to the proliferation of smooth muscle and epithelial cells within the prostatic transition zone.

The term "detrusor" refers to the muscle of the bladder.

The term "detrusor overactivity" as used herein refers to the occurrence of involuntary detrusor contractions during filling cystometry. These contractions, which can be spontaneous or provoked, are unable to be suppressed by the patient. They can take a wave (phasic) form, of variable duration and amplitude, on the cystometrogram. Urinary incontinence may or may not occur. These contractions can be voiding contractions, partially-voiding contractions, non-voiding contractions (NVC) or combinations thereof. The term "detrusor overactivity" is defined by the International Continence Society (ICS) as follows: Detrusor overactivity is a urodynamic observation characterized by involuntary detrusor contractions during the filling phase that can be spontaneous or provoked (Abrams P et al., Urology 2003, 62 (Supplement 5B): 28-37 and 40-42).

The term "free base" as used herein refers to a basic chemical compound itself, not in the form of a salt. For example, vibegron free base refers to (6S)—N-[4-[[(2S,5R)-5-[(R)-hydroxy(phenyl)methyl]pyrrolidin-2-yl]methyl]phenyl]-4-oxo-7,8-dihydro-6H-pyrrolo[1,2-a]pyrimidine-6-carboxamide.

The term "micturition," as used herein, means urination.

The term "OAB wet" as used herein means overactive bladder as defined by urinary frequency and urinary urgency, with incontinence.

The term "OAB dry" as used herein means overactive bladder as defined by urinary frequency and urinary urgency, without incontinence.

The term "pharmaceutically acceptable salt" means those salts of compounds that are safe and effective for use in subjects and that possess the desired biological activity.

Pharmaceutically acceptable salts of a basic compound can be salts of organic or inorganic acids. In some embodiments, the organic and inorganic acids include but are not limited to hydrochloric acid, hydrobromic acid, sulfuric acid, phosphoric acid, citric acid, maleic acid, mandelic acid, succinic acid and methanesulfonic acid. See generally, *Journal of Pharmaceutical Science*, 66, 2 (1977), which is incorporated herein by reference in its entirety.

The term "$C_{max}$" as used herein refers to the maximum plasma concentration of a drug after it is administered.

The term "$T_{max}$" as used herein refers to the time after administration of a drug when the maximum plasma concentration is reached.

The term "AUC" as used herein refers to the area under the curve of a plot of plasma concentration versus time following administration of a drug.

The term "steady state" means that the amount of the drug reaching the system is approximately the same as the amount of the drug leaving the system. Thus, at "steady-state," the patient's body eliminates the drug at approximately the same rate that the drug becomes available to the patient's system through absorption into the blood stream.

The terms "treating," "treatment," or "therapy," as used herein refer to partially or completely alleviating, ameliorating, improving, relieving, delaying onset of, inhibiting progression of, reducing severity of, reducing incidence of, attenuating one or more of the overactive bladder symptoms associated with benign prostatic hyperplasia, or any combination thereof.

The term "treatment period" means the period of time during which the drug is administered to a subject. For example, the treatment period can be from about 2 weeks to about 2 years. In some embodiments, the treatment period can be about 2, about 4, about 6, about 8, about 10, about 12, about 14, about 16, about 18, about 20, about 24, about 52, about 76 or about 104 weeks. The efficacy of the drug can be assessed by measuring certain parameters and calculating the changes from baseline over the treatment period. The efficacy parameters include, but are not limited to, micturitions, urge urinary incontinence episodes, total incontinence episodes, and urgency episodes.

The term "subject" as used herein refers to someone who is at a heightened risk of suffering from, is currently suffering from, or has at any time in the past suffered from overactive bladder symptoms and has benign prostatic hyperplasia (BPH). A subject with BPH is at a heightened risk of suffering from overactive bladder symptoms for example, when the subject has developed BPH symptoms unrelated to overactive bladder symptoms or when overactive bladder symptoms have been relieved, reduced, or attenuated previously in the subject.

Additional definitions related to urological conditions can be found, e.g., in Chapple et al. (2018) "Terminology report from the International Continence Society (ICS) Working Group on Underactive Bladder (UAB)" Neurology and Urodynamics 37:2928-2931. Additional definitions related to benign prostatic hyperplasia can be found, e.g., at the "Guidelines for Management of Benign Prostatic Hyperplasia," available at www.auanet.org/benign-prostatic-hyperplasia-(2010-reviewed-and-validity-confirmed-2014). All these documents are herein incorporated by reference in their entireties.

Methods of Treatment

The present disclosure relates to a method of treating overactive bladder symptoms in men with BPH comprising orally administering to a subject in need thereof a dosage of vibegron such that the desired efficacy is maintained while the undesirable side effects are minimized. It is unexpected that side effects associated with elevated $C_{max}$ can be disproportionately reduced by selection of the dosage of vibegron.

The present disclosure provides a method of treating overactive bladder symptoms in men with BPH, the method comprising orally administering to a subject in need thereof an amount of from 50 mg to 100 mg of vibegron per day. As used herein, "per day" refers to a continuous 24-hour period, and sometimes refers to "per 24 hours."

The present disclosure provides a method of reducing or decreasing micturitions in a subject with BPH in need thereof, the method comprising orally administering to the subject an amount of from about 60 mg to about 90 mg of vibegron per day.

The present disclosure provides a method of treating overactive bladder symptoms in a subject with BPH, wherein the subject has a symptom selected from the group consisting of urgency urinary incontinence, urge incontinence, urinary urgency, urinary frequency, nocturia, and a combination thereof.

In some embodiments, the subject with BPH has persistent OAB symptoms selected from the group consisting of urgency urinary incontinence, urge incontinence, urinary urgency, urinary frequency, nocturia, and a combination thereof. In some embodiments, the subjects with BPH are treated with vibegron and are concomitantly taking a pharmacological therapy for BPH. In some embodiments, the method disclosed herein can also treat voiding dysfunction (e.g., decreased and intermittent force of stream and the sensation of urge).

In some embodiments, the amount of vibegron administered per day is from about 55 mg to about 100 mg, from about 60 mg to about 100 mg, from about 65 mg to about 100 mg, from about 70 mg to about 100 mg, from about 75 mg to about 100 mg, from about 80 mg to about 100 mg, from about 85 mg to about 100 mg, from about 90 mg to about 100 mg, or from about 95 mg to about 100 mg.

In some embodiments, the amount of vibegron administered per day is from about 50 mg to about 95 mg, from about 50 mg to about 90 mg, from about 50 mg to about 85 mg, from about 50 mg to about 80 mg, from about 50 mg to about 75 mg, from about 50 mg to about 70 mg, from about 50 mg to about 65 mg, from about 50 mg to about 60 mg, or from about 50 mg to about 55 mg.

In some embodiments, the amount of vibegron administered per day is from about 60 mg to about 90 mg, from about 65 mg to about 85 mg, or from about 70 mg to about 80 mg. In some embodiments, the amount of vibegron administered per day is from 60 mg to 90 mg, from 65 mg to 85 mg, or from 70 mg to 80 mg.

In some embodiments, the amount of vibegron administered per day is about 55 mg, about 60 mg, about 65 mg, about 70 mg, about 75 mg, about 80 mg, about 85 mg, about 90 mg, or about 95 mg. In some embodiments, the amount of vibegron administered per day is about 75 mg. In some embodiments, the amount of vibegron administered per day is 75 mg.

In some embodiments, the amount of vibegron administered per day is not about 50 mg. In some embodiments, the amount of vibegron administered per day is not about 100 mg. In some embodiments, the amount of vibegron administered per day is not 50 mg. In some embodiments, the amount of vibegron administered per day is not 100 mg.

In some embodiments the treatment period does not include a dose titration with vibegron. In some embodiments treatment is initiated with administration of 75 mg of vibegron per day.

In some embodiments the treatment period does include a dose titration with vibegron. In some embodiments treatment is not initiated with administration of 75 mg of vibegron per day.

In some embodiments, the subject has the symptoms of urgency urinary incontinence, urinary urgency, and urinary frequency.

In some embodiments, the subject has one or more symptoms of urgency urinary incontinence (or urge urinary incontinence), urinary urgency, urinary frequency and nocturia.

In some embodiments, the subject has ≤12 micturition episodes per day prior to the treatment. In some embodiments, the subject has >12 micturition episodes per day prior to the treatment.

In some embodiments, the subject has the symptom of urinary incontinence. In some embodiments, the subject does not have the symptom of urinary incontinence.

In some embodiments, the subject is a mammal. In some embodiments the subject is a human or an animal. In some embodiments, the subject is a human.

In some embodiments, the subject is over the age of 18 years. In some embodiments, the subject is over the age of 45 years. In some embodiments, the subject is over the age of 50 years. In some embodiments, the subject is over the age of 55 years. In some embodiments, the subject is over the age of 60 years. In some embodiments, the subject is over the age of 65 years. In some embodiments, the subject is over the age of 70 years. In some embodiments, the subject is over the age of 75 years.

In some embodiments, the subject suffers from renal impairment or is at risk of suffering from renal impairment. In some embodiments, the subject suffers from mild renal impairment, moderate renal impairment, or severe renal impairment.

In some embodiments, the subject has received prior OAB therapy. In some embodiments, the subject has not received prior OAB therapy.

In some embodiments, the subject has undergone or been subjected to a BPH procedure or BPH-related surgery prior to initiation of vibegron treatment. In some embodiments, the subject has undergone or been subjected to prostate surgery. In some embodiments, the subject has undergone or been subjected to a minimally invasive prostate procedure.

Examples of BPH procedures or BPH-related surgeries include but are not limited to transurethral resection of the prostate, transurethral incision of the prostate, laser enucleation of prostate, prostatectomy, prostatic stent placement, UroLift, catheterization, transurethral microwave thermotherapy, transurethral electroevaporation of the prostate, transurethral needle ablation, and high intensity focused ultrasound.

In some embodiments, the subject is administered vibegron prior to a BPH procedure or BPH-related surgery. In some embodiments, the subject is administered vibegron concurrent to a BPH procedure or BPH-related surgery.

In some embodiments the subject suffers from renal impairment and is administered about 75 mg of vibegron per day.

In some embodiments, the subject is concomitantly receiving, taking or otherwise being exposed to a cytochrome P450 inhibitor, such as a CYP3A inhibitor, and with drugs that are substrates of the following CYPs: CYP1A2, 2B6, 2C8, 2C9, 2C19, 2D6, and 3A4.

In some embodiments, the subject is concomitantly receiving, taking, or otherwise being exposed to a CYP 2D6 substrate.

In some embodiments, the subject is concomitantly receiving, taking, or otherwise being exposed to a P-glycoprotein inhibitor.

CYP3A/P-glycoprotein inhibitors include but are not limited to amiodarone, carvedilol, clarithromycin, dronedarone, itraconazole, lapatinib, lopinavir and ritonavir, propafenone, quinidine, ranolazine, ritonavir, saquinavir and ritonavir, telaprevir, tipranavir and ritonavir, verapamil, curcumin, cyclosporine A, eltrombopag, atazanavir and ritonavir, clarithromycin, cyclosporine, erythromycin, gemfibrozil, lopinavir and ritonavir, rifampin (single dose), simeprevir, p-aminohippuric acid (PAH)(b), probenecid, teriflunomide, cimetidine, dolutegravir, isavuconazole, ranolazine, trimethoprim, and vandetanib.

CYP 2D6 substrates include but are not limited to imipramine, amitriptyline, fluoxetine, paroxetine, fluvoxamine, venlafaxine, duloxetine, mianserin, mirtazapine, opioids, codeine, morphine, tramadol, O-desmethyltramadol, N,O-didesmethyltramadol, oxycodone, hydrocodone, hydromorphone, tapentadol, haloperidol, risperidone, perphenazine, thioridazine, zuclopenthixol, iloperidone, aripiprazole, chlorpromazine, levomepromazine, remoxipride, minaprine, tamoxifen, hydroxytamoxifen, beta-blockers, metoprolol, timolol, alprenolol, carvedilol, bufuralol, nebivolol, propranolol, debrisoquine, flecainide, propafenone, encainide, mexiletine, lidocaine, sparteine, ondansetron, donepezil, phenformin, tropisetron, amphetamine, methoxyamphetamine, dextromethamphetamine, atomoxetine, chlorphenamine, dexfenfluramine, dextromethorphan, dextrorphan, metoclopramide, perhexiline, phenacetin, promethazine, m-tyramine, warfarin, tolterodine, and p-tyramine.

In some embodiments, the subject is administered about 75 mg of vibegron per day and is concomitantly receiving, taking or otherwise being exposed to a CYP3A inhibitor.

In some embodiments, the subject is administered about 75 mg of vibegron per day and is concomitantly receiving, taking or otherwise being exposed to a CYP 2D6 substrate.

In some embodiments, the subject is administered about 75 mg of vibegron per day and is concomitantly receiving, taking, or otherwise being exposed to a P-glycoprotein inhibitor.

In some embodiments the subject is not concomitantly receiving, taking, or otherwise being exposed to a beta blocker.

In some embodiments the subject is not concomitantly receiving, taking, or otherwise being exposed to an alpha blocker.

In some embodiments the subject is concomitantly receiving, taking, or otherwise being exposed to an alpha blocker.

Alpha blockers include but are not limited phenoxybenzamine, phentolamine, tolazoline, trazodone, alfuzosin, doxazosin, prazosin, tamsulosin, terazosin, silodosin, aatipamezole, idazoxan, mirtazapine, yohimbine, carvedilol, labetalol.

In some embodiments, the subject is administered 75 mg of vibegron per day and is concomitantly receiving, taking or otherwise being exposed to an alpha blocker.

In some embodiments the subject is concomitantly receiving, taking, or otherwise being exposed to a 5-alpha reductase inhibitor (5-ARI).

5-ARIs include but are not limited to alfatradiol, dutasteride, episteride, finasteride, and saw palmetto extract.

In some embodiments, the subject is administered 75 mg of vibegron per day and is concomitantly receiving, taking or otherwise being exposed to a 5-ARI.

In some embodiments the subject is concomitantly receiving, taking or otherwise being exposed to an alpha blocker and 5-ARI.

In some embodiments, vibegron is administered with a meal, within 60 minutes after a meal, or within 2 hours after a meal.

In some embodiments, vibegron is administered without a meal or before a meal. In some embodiments, vibegron is administered more than two hours before a meal.

In some embodiments, vibegron is administered once per day, twice per day, or three times per day. In some embodiments, vibegron is administered once per day.

The efficacy of the treatment can be measured by a change from baseline over the treatment period (e.g., 8 weeks or 12 weeks) in average number of micturitions per 24 hours in a subject with BPH.

In some embodiments, the subject is administered about 75 mg of vibegron per day, and experiences a change from baseline over the treatment period (e.g., 8 weeks or 12 weeks) in average number of micturitions per 24 hours, wherein the change is greater than that for a subject taking placebo. The difference from placebo is from about −0.2 to about −1.5, for example, about −0.2, −0.3, −0.4, −0.5, −0.6, −0.7, −0.8, −0.9, −1.0, −1.1, −1.2, −1.3, −1.4, or −1.5, or a range between any two of the preceding values.

In some embodiments, the subject is administered about 60 mg to about 90 mg a day, for example about 65 mg to about 85 mg, from about 70 mg to about 80 mg, or about 75 mg of vibegron per day, and experiences a change from baseline over the treatment period (e.g., 8 weeks or 12 weeks) in average number of micturitions per 24 hours, wherein the change is greater than that for a subject taking placebo. The difference from placebo is from about −0.5 to about −1.0, for example, about −0.5, −0.6, −0.7, −0.8, −0.9, or −1.0, or a range between any two of the preceding values.

In some embodiments, the subject is administered about 60 mg to about 90 mg a day, for example about 65 mg to about 85 mg, from about 70 mg to about 80 mg, or about 75 mg of vibegron per day, and experiences a reduction or decrease in average number of micturitions per 24 hours, wherein the reduction or decrease is between about 1.5 and about 3.0 times greater than that for a subject taking placebo, for example, about 1.5, 1.6, 1.7, 1.8, 1.9, 2.0, 2.1, 2.2, 2.3, 2.4, 2.5, 2.6, 2.7, 2.8, 2.9, or 3.0, or a range between any two of the preceding values.

In some embodiments, the subject is administered about 60 mg to about 90 mg a day, for example about 65 mg to about 85 mg, from about 70 mg to about 80 mg, or about 75 mg of vibegron per day, and experiences a reduction or decrease in average number of micturitions per 24 hours, wherein the reduction or decrease is between about 2.0 and about 2.5 times greater than that for a subject taking placebo, for example, about 2.0, 2.1, 2.2, 2.3, 2.4, or 2.5, or a range between any two of the preceding values.

In some embodiments, the subject is administered about 60 to about 90 mg a day, for example about 65 mg to about 85 mg, from about 70 to about 80 mg, or about 75 mg of vibegron per day, and experiences a decrease in average number of micturitions per 24 hours, wherein the decrease is greater than that for a subject taking tolterodine extended release (ER) 4 mg.

In some embodiments, the subject is administered about 75 mg of vibegron per day, and experiences a change from baseline over the treatment period (e.g., 8 weeks or 12 weeks) in average number of micturitions per 24 hours of from about −1.0 to about −2.5, for example, about −1.0, −1.1, −1.2, −1.3, −1.4, −1.5, −1.6, −1.7, −1.8, −1.9, −2.0, −2.1, −2.2, −2.3, −2.4, or −2.5, or a range between any two of the preceding values.

The efficacy of the treatment can be measured by a change from baseline over the treatment period (e.g., 8 weeks or 12 weeks) in average number of urgency episodes per 24 hours in a subject with BPH.

In some embodiments, the subject is administered about 75 mg of vibegron per day, and experiences a change from baseline over the treatment period (e.g., 8 weeks or 12 weeks) in average number of urgency episodes per 24 hours, wherein the change is greater than that for a subject taking placebo. The difference from placebo is from about −0.2 to about −1.5, for example, about −0.2, −0.3, −0.4, −0.5, −0.6, −0.7, −0.8, −0.9, −1.0, −1.1, −1.2, −1.3, −1.4, or −1.5, or a range between any two of the preceding values.

In some embodiments, the subject is administered about 60 mg to about 90 mg a day, for example about 65 mg to about 85 mg, from about 70 mg to about 80 mg, or about 75 mg of vibegron per day, and experiences a change from baseline over the treatment period (e.g., 8 weeks or 12 weeks) in average number of urgency episodes per 24 hours, wherein the change is greater than that for a subject taking placebo. The difference from placebo is from about −0.4 to about −1.0, for example, about −0.4, −0.5, −0.6, −0.7, −0.8, −0.9, or −1.0, or a range between any two of the preceding values.

In some embodiments, the subject is administered about 60 mg to about 90 mg a day, for example about 65 mg to about 85 mg, from about 70 mg to about 80 mg, or about 75 mg of vibegron per day, and experiences a reduction or decrease in average number of urgency episodes per 24 hours, wherein the reduction or decrease is between about 1.2 and about 3.0 times greater than that for a subject taking placebo, for example, about 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, or a range between any two of the preceding values.

In some embodiments, the subject is administered about 60 to about 90 mg a day, for example about 65 mg to about 85 mg, from about 70 to about 80 mg, or about 75 mg of vibegron per day, and experiences a decrease in average number of urgency episodes per 24 hours, wherein the decrease is greater than that for a subject taking tolterodine extended release (ER) 4 mg.

In some embodiments, the subject is administered about 75 mg of vibegron per day, and experiences a change from baseline over the treatment period (e.g., 8 weeks or 12 weeks) in average number of urgency episodes per 24 hours from about −1.0 to about −2.5, for example, about −1.0, −1.1, −1.2, −1.3, −1.4, −1.5, −1.6, −1.7, −1.8, −1.9, −2.0, −2.1, −2.2, −2.3, −2.4, or −2.5, or a range between any two of the preceding values.

In some embodiments, the subject is administered about 75 mg of vibegron per day, and experiences a change from baseline over the treatment period (e.g., 8 weeks or 12 weeks) in average number of urgency episodes per 24 hours and average number of micturitions per 24 hours, wherein the change is greater than that for a subject taking placebo. In some embodiments, the change from baseline in average number of micturitions per 24 hours is from about −1.0 to about −2.5, for example, about −1.0, −1.1, −1.2, −1.3, −1.4, −1.5, −1.6, −1.7, −1.8, −1.9, −2.0, −2.1, −2.2, −2.3, −2.4, or −2.5, or a range between any two of the preceding values, and the change from baseline in average number of urgency episodes per 24 hours is from about −1.0 to about −2.5, for example, about −1.0, −1.1, −1.2, −1.3, −1.4, −1.5, −1.6, −1.7, −1.8, −1.9, −2.0, −2.1, −2.2, −2.3, −2.4, or −2.5, or a range between any two of the preceding values.

The efficacy of the treatment can be measured by a change from baseline over the treatment period (e.g., 8 weeks or 12 weeks) in average number of urge urinary incontinence (UUI) episodes per day in a subject with BPH.

In some embodiments, the subject has an average of ≥1, ≥2, or ≥3 urge urinary incontinence (UUI) episodes per day prior to treatment and is administered about 75 mg of vibegron per day, and experiences a change from baseline over the treatment period (e.g., 8 weeks or 12 weeks) in average number of UUI episodes, wherein the change is greater than that for a subject taking placebo. The difference from placebo is from about −0.2 to about −1.5, for example, about −0.2, −0.3, −0.4, −0.5, −0.6, −0.7, −0.8, −0.9, −1.0, −1.1, −1.2, −1.3, −1.4, or −1.5, or a range between any two of the preceding values.

In some embodiments, the subject is administered about 75 mg of vibegron per day, and experiences a change from baseline over the treatment period (e.g., 8 weeks or 12 weeks) in average number of UUI episodes of from about −1.3 to about −2.5, for example, about −1.3, −1.4, −1.5, −1.6, −1.7, −1.8, −1.9, −2.0, −2.1, −2.2, −2.3, −2.4, or −2.5, or a range between any two of the preceding values.

The efficacy of the treatment can be measured by a change from baseline over the treatment period (e.g., 8 weeks or 12 weeks) in the average volume voided (mL) per micturition.

In some embodiments, the subject is administered about 75 mg of vibegron per day, and experiences a change in the average volume voided (mL) per micturition, wherein the change is greater than that for a subject taking placebo. The difference from placebo is from about 20 mL to about 35 mL, for example, about 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, or 35 mL, or a range between any two of the preceding values.

In some embodiments, the subject has an average of ≥1, ≥2, or ≥3 urge urinary incontinence (UUI) episodes per day prior to treatment and is administered about 75 mg of vibegron per day, and experiences at least 30%, at least 40%, at least 45%, at least 50%, at least 55%, at least 60%, at least 65%, at least 70%, at least 75%, at least 80%, at least 85%, at least 90%, or at least 95% reduction in the average number of daily UUI episodes over the treatment period (e.g., 8 weeks or 12 weeks).

In some embodiments, the subject has an average of ≥1, ≥2, or ≥3 urgency episodes per day prior to treatment and is administered about 75 mg of vibegron per day, and experiences at least 30%, at least 40%, at least 45%, at least 50%, at least 55%, at least 60%, at least 65%, at least 70%, or at least 75% reduction in the average number of daily urgency episodes over the treatment period (e.g., 8 weeks or 12 weeks).

In some embodiments, the subject is administered about 75 mg of vibegron per day, and experiences at least 30%, at least 40%, at least 45%, at least 50%, at least 55%, at least 60%, at least 65%, at least 70%, at least 75%, at least 80%, at least 85%, at least 90%, at least 95%, at least 100% increase in the average volume voided (mL) per micturition, wherein the change is greater than that for a subject taking placebo.

The efficacy of the treatment can also be measured by a change from baseline over the treatment period (e.g., 8 weeks or 12 weeks) in the average International Prostate Symptom Score (IPSS) (i.e., IPSS total score) and/or IPSS Quality of Life (QoL) score in a subject with BPH.

The International Prostate Symptom Score (IPSS) is based on the responses to 7 questions concerning urinary symptoms and 1 question concerning quality of life. Each question concerning urinary symptoms allows the subject to choose 1 out of 6 answers indicating increasing severity of the particular symptom. The responses are assigned points from 0 to 5. The total score can therefore range from 0 to 35 (asymptomatic to very symptomatic). The answers to the single question to assess the quality of life question range from "delighted" to "terrible" or 0 to 6, i.e., the IPSS QoL score.

In some embodiments, the subject has an IPSS score of ≥5, ≥8, or ≥10, and is administered about 75 mg of vibegron per day, and experiences a change from baseline over the treatment period (e.g., 8 weeks or 12 weeks) in average IPSS score, wherein the change is greater than that for a subject taking placebo. The difference from placebo is from about −0.5 to about −2.5, for example, about −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.1, −2.2, −2.3, −2.4, −2.5, or a range between any two of the preceding values.

In some embodiments, the subject is administered about 75 mg of vibegron per day, and experiences a change from baseline over the treatment period (e.g., 8 weeks or 12 weeks) in average IPSS score of from about −2.5 to about −5.0, for example, about −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0 or a range between any two of the preceding values.

The efficacy of the treatment can be measured by a change from baseline over the treatment period (e.g., 8 weeks or 12 weeks) in the mean International Index of Erectile Function (IIEF) domain scores in a subject with BPH.

The 15-question IIEF Questionnaire is a validated, multidimensional, self-administered investigation that has been found useful in the clinical assessment of erectile dysfunction and treatment outcomes in clinical trials. A score of 0-5 is awarded to each of the 15 questions that examine the five main domains of male sexual function: erectile function, orgasmic function, sexual desire, intercourse satisfaction, and overall satisfaction. The IIEF does not yield a total score, only domain scores are calculated.

In some embodiments, the subject has an erectile function domain score of <25, <20, <15, or <10 prior to treatment and is administered about 75 mg of vibegron per day, and experiences a change from baseline over the treatment period (e.g., 8 weeks or 12 weeks) in erectile function domain score, wherein the change is greater than that for a subject taking placebo. The difference from placebo is from about 5.0 to about 20.0, for example, about 5.0, 6.0, 7.0, 8.0, 9.0, 10.0, 11.0, 12.0, 13.0, 14.0, 15.0, 16.0, 17.0, 18.0, 19.0, or 20.0, or a range between any two of the preceding values.

In some embodiments, the subject has an orgasmic function domain score of <8, <6, <4, or <2 prior to treatment and is administered about 75 mg of vibegron per day, and experiences a change from baseline over the treatment period (e.g., 8 weeks or 12 weeks) in orgasmic function domain score, wherein the change is greater than that for a subject taking placebo. The difference from placebo is from about 2.0 to about 8.0, for example, about 2.0, 2.5, 3.0, 3.5, 4.0, 4.5, 5.0, 5.5, 6.0, 6.5, 7.0, 7.5, or 8.0, or a range between any two of the preceding values.

In some embodiments, the subject has a sexual desire domain score of <8, <6, <4, or <2 prior to treatment and is administered about 75 mg of vibegron per day, and experiences a change from baseline over the treatment period (e.g., 8 weeks or 12 weeks) in sexual desire domain score, wherein the change is greater than that for a subject taking placebo. The difference from placebo is from about 2.0 to about 8.0, for example, about 2.0, 2.5, 3.0, 3.5, 4.0, 4.5, 5.0, 5.5, 6.0, 6.5, 7.0, 7.5, or 8.0, or a range between any two of the preceding values.

In some embodiments, the subject has an overall satisfaction domain score of <8, <6, <4, or <2 prior to treatment and is administered about 75 mg of vibegron per day, and experiences a change from baseline over the treatment period (e.g., 8 weeks or 12 weeks) in overall satisfaction domain score, wherein the change is greater than that for a subject taking placebo. The difference from placebo is from about 2.0 to about 8.0, for example, about 2.0, 2.5, 3.0, 3.5, 4.0, 4.5, 5.0, 5.5, 6.0, 6.5, 7.0, 7.5, or 8.0, or a range between any two of the preceding values.

In some embodiments, the subject has an intercourse satisfaction domain score of <12, <10, <8, or <6 prior to treatment and is administered about 75 mg of vibegron per day, and experiences a change from baseline over the treatment period (e.g., 8 weeks or 12 weeks) in intercourse satisfaction domain score, wherein the change is greater than that for a subject taking placebo. The difference from placebo is from about 2.0 to about 10.0, for example, about 2.0, 2.5, 3.0, 3.5, 4.0, 4.5, 5.0, 5.5, 6.0, 6.5, 7.0, 7.5, 8.0, 8.5, 9.0, 9.5, or 10.0, or a range between any two of the preceding values.

The safety of the treatment can be measured by a change from baseline over the treatment period (e.g., 8 weeks or 12 weeks) in the post void residual urine volume (PVR) in a subject with BPH.

In some embodiments, the subject is administered about 75 mg of vibegron per day, and experiences an increase from baseline over the treatment period (e.g., 8 weeks or 12 weeks) in PVR of not more than about 5 mL, 4 mL, 3 mL, 2 mL, or 1 mL. In some embodiments, the subject is administered about 75 mg of vibegron per day, and experiences a decrease from baseline over the treatment period (e.g., 8 weeks or 12 weeks) in PVR of at least about 1 mL, 2 mL, 3 mL, 4 mL, or 5 mL.

In some embodiments, the subject is administered about 75 mg of vibegron per day, and experiences a change from baseline over the treatment period (e.g., 8 weeks or 12 weeks) in PVR of from about 10 mL to about −20 mL, for example, about 10 mL, 8 mL, 6 mL, 5 mL, 4 mL, 3 mL, 2 mL, 1 mL, 0 mL, −1 mL, −2 mL, −3 mL, −4 mL, −5 mL, −6 mL, −7 mL, −8 mL, −9 mL, −10 mL, −12 mL, −14 mL, −16 mL, −18 mL, or −20 mL, or a range between any two of the preceding values.

The efficacy of the treatment can be measured by a change from baseline over the treatment period (e.g., 8 weeks or 12 weeks) in average number of nocturia episodes per night in a subject with BPH.

In some embodiments, the subject has an average of ≥1, ≥2, or ≥3 nocturia episodes per night prior to treatment and is administered about 75 mg of vibegron per day, and experiences a change from baseline over the treatment period (e.g., 8 weeks or 12 weeks) in average number of nocturia episodes per night, wherein the change is greater than that for a subject taking placebo. The difference from placebo is from about −0.2 to about −1.5, for example, about −0.2, −0.3, −0.4, −0.5, −0.6, −0.7, −0.8, −0.9, −1.0, −1.1, −1.2, −1.3, −1.4, or −1.5, or a range between any two of the preceding values.

In some embodiments, the subject is administered about 75 mg of vibegron per day, and experiences a change from baseline over the treatment period (e.g., 8 weeks or 12 weeks) in nocturia episodes per night of from about −1.3 to about −2.5, for example, about −1.3, −1.4, −1.5, −1.6, −1.7, −1.8, −1.9, −2.0, −2.1, −2.2, −2.3, −2.4, or −2.5, or a range between any two of the preceding values.

In some embodiments, the subject is administered about 75 mg of vibegron per day, and does not experience a substantial change in post void residual (PVR) volume over the treatment period (e.g., 8 weeks or 12 weeks). Changes from baseline in blood pressure (BP) and heart rate (HR) for the subjects taking vibegron are not substantially different for the subjects taking a placebo. In some embodiments, the subject experiences a mean maximum change of systolic blood pressure (SBP) from baseline over the treatment period (e.g., 8 weeks or 12 weeks), and the mean maximum change is less than 2.0 mm/Hg, less than 1.9 mm/Hg, less than 1.8 mm/Hg, less than 1.7 mm/Hg, less than 1.6 mm/Hg, less than 1.5 mm/Hg, less than 1.4 mm/Hg, less than 1.3 mm/Hg, less than 1.2 mm/Hg, less than 1.1 mm/Hg, less than 1.0 mm/Hg, less than 0.9 mm/Hg, less than 0.8 mm/Hg, less than 0.7 mm/Hg, less than 0.6 mm/Hg, or less than 0.5 mm/Hg from that of a subject taking a placebo.

In some embodiments, the subject is administered about 75 mg of vibegron per day, and experiences a mean maximum change of SBP from baseline over the treatment period (e.g., 8 weeks or 12 weeks) of less than 2 mm/Hg from that of a subject taking a placebo. In some embodiments, the subject is administered about 75 mg of vibegron per day, and experiences a mean maximum change of SBP from baseline over the treatment period (e.g., 8 weeks or 12 weeks) of less than 1 mm/Hg from that of a subject taking a placebo.

In some embodiments, the subject is over the age of 65 and is administered about 75 mg of vibegron per day, and experiences a mean maximum change of SBP from baseline over the treatment period (e.g., 8 weeks or 12 weeks) of less than 2 mm/Hg from that of a subject taking a placebo. In some embodiments, the subject is over the age of 65 and is administered about 75 mg of vibegron per day, and experiences a mean maximum change of SBP from baseline over the treatment period (e.g., 8 weeks or 12 weeks) of less than 1 mm/Hg from that of a subject taking a placebo.

In some embodiments, the subject is over the age of 45 and is administered about 75 mg of vibegron per day, and experiences a mean maximum change of SBP from baseline over the treatment period (e.g., 8 weeks or 12 weeks) of less than 2 mm/Hg from that of a subject taking a placebo. In some embodiments, the subject is over the age of 45 and is administered about 75 mg of vibegron per day, and experiences a mean maximum change of SBP from baseline over the treatment period (e.g., 8 weeks or 12 weeks) of less than 1 mm/Hg from that of a subject taking a placebo.

In some embodiments, the subject experiences a mean maximum change of diastolic blood pressure (DBP) from baseline over the treatment period (e.g., 8 weeks or 12 weeks), and the mean maximum change is less than 2.0 mm/Hg, less than 1.9 mm/Hg, less than 1.8 mm/Hg, less than 1.7 mm/Hg, less than 1.6 mm/Hg, less than 1.5 mm/Hg, less than 1.4 mm/Hg, less than 1.3 mm/Hg, less than 1.2 mm/Hg, less than 1.1 mm/Hg, less than 1.0 mm/Hg, less than 0.9 mm/Hg, less than 0.8 mm/Hg, less than 0.7 mm/Hg, less than 0.6 mm/Hg, or less than 0.5 mm/Hg from that of a subject taking a placebo.

In some embodiments, the subject is administered about 75 mg of vibegron per day, and experiences a mean maximum change of DBP from baseline over the treatment period (e.g., 8 weeks or 12 weeks) of less than 2 mm/Hg from that of a subject taking a placebo. In some embodiments, the subject is administered about 75 mg of vibegron per day, and experiences a mean maximum change of DBP from baseline over the treatment period (e.g., 8 weeks or 12 weeks) of less than 1 mm/Hg from that of a subject taking a placebo.

In some embodiments, the subject is over the age of 65 and is administered about 75 mg of vibegron per day, and experiences a mean maximum change of DBP from baseline over the treatment period (e.g., 8 weeks or 12 weeks) of less than 2 mm/Hg from that of a subject taking a placebo. In some embodiments, the subject is over the age of 65 and is administered about 75 mg of vibegron per day, and experiences a mean maximum change of DBP from baseline over the treatment period (e.g., 8 weeks or 12 weeks) of less than 1 mm/Hg from that of a subject taking a placebo.

In some embodiments, the subject is over the age of 45 and is administered about 75 mg of vibegron per day, and experiences a mean maximum change of DBP from baseline over the treatment period (e.g., 8 weeks or 12 weeks) of less than 2 mm/Hg from that of a subject taking a placebo. In some embodiments, the subject is over the age of 45 and is administered about 75 mg of vibegron per day, and experiences a mean maximum change of DBP from baseline over the treatment period (e.g., 8 weeks or 12 weeks) of less than 1 mm/Hg from that of a subject taking a placebo.

In some embodiments, the subject is over the age of 45, is administered about 75 mg of vibegron once per day, and experiences a mean maximum change of DBP from baseline over the treatment period (e.g., 8 weeks or 12 weeks) of less than 1 mm/Hg from that of a subject taking a placebo, and a mean maximum change of SBP from baseline over the treatment period (e.g., 8 weeks or 12 weeks) of less than 1 mm/Hg from that of a subject taking a placebo.

In some embodiments, the subject is over the age of 65, is administered about 75 mg of vibegron once per day, and experiences a mean maximum change of DBP from baseline over the treatment period (e.g., 8 weeks or 12 weeks) of less than 1 mm/Hg from that of a subject taking a placebo, and a mean maximum change of SBP from baseline over the treatment period (e.g., 8 weeks or 12 weeks) of less than 1 mm/Hg from that of a subject taking a placebo.

In some embodiments, the subject experiences a mean maximum change of systolic blood pressure (SBP) from baseline over the treatment period (e.g., 8 weeks or 12 weeks) of less than 10 mm/Hg, less than 9.5 mm/Hg, less than 9 mm/Hg, less than 8.5 mm/Hg, less than 8 mm/Hg, less than 7.5 mm/Hg, less than 7 mm/Hg, less than 6.5 mm/Hg, less than 6 mm/Hg, less than 5.5 mm/Hg, or less than 5 mm/Hg.

In some embodiments, the subject is administered about 75 mg of vibegron per day, and experiences a mean maximum change of SBP from baseline over the treatment period (e.g., 8 weeks or 12 weeks) of less than 10 mm/Hg.

In some embodiments, the subject is over the age of 65 and is administered about 75 mg of vibegron per day, and experiences a mean maximum change of SBP from baseline over the treatment period (e.g., 8 weeks or 12 weeks) of less than 10 mm/Hg.

In some embodiments, the subject is over the age of 45 and is administered about 75 mg of vibegron per day, and experiences a mean maximum change of SBP from baseline over the treatment period (e.g., 8 weeks or 12 weeks) of less than 10 mm/Hg.

In some embodiments, the subject experiences a mean maximum change of diastolic blood pressure (DBP) from baseline over the treatment period (e.g., 8 weeks or 12 weeks) of less than 7 mm/Hg, less than 6.5 mm/Hg, less than 6 mm/Hg, less than 5.5 mm/Hg, less than 5 mm/Hg, less than 4.5 mm/Hg, less than 4 mm/Hg, less than 3.5 mm/Hg, less than 3 mm/Hg, less than 2.5 mm/Hg, or less than 2 mm/Hg.

In some embodiments, the subject is administered about 75 mg of vibegron per day, and experiences a mean maximum change of DBP from baseline over the treatment period (e.g., 8 weeks or 12 weeks) of less than 7 mm/Hg.

In some embodiments, the subject is over the age of 65 and is administered about 75 mg of vibegron per day, and experiences a mean maximum change of DBP from baseline over the treatment period (e.g., 8 weeks or 12 weeks) of less than 7 mm/Hg.

In some embodiments, the subject is over the age of 45 and is administered about 75 mg of vibegron per day, and experiences a mean maximum change of DBP from baseline over the treatment period (e.g., 8 weeks or 12 weeks) of less than 7 mm/Hg.

In some embodiments, the subject over the age of 45 is administered about 75 mg of vibegron once per day, experiences a mean maximum change of DBP from baseline over the treatment period (e.g., 8 weeks or 12 weeks) of less than 7 mm/Hg, and a mean maximum change of SBP from baseline over the treatment period (e.g., 8 weeks or 12 weeks) of less than 10 mm/Hg.

In some embodiments, the subject over the age of 65 is administered about 75 mg of vibegron once per day, experiences a mean maximum change of DBP from baseline over the treatment period (e.g., 8 weeks or 12 weeks) of less than 7 mm/Hg, and a mean maximum change of SBP from baseline over the treatment period (e.g., 8 weeks or 12 weeks) of less than 10 mm/Hg.

Pharmaceutical Unit Dose Composition

The present disclosure provides pharmaceutical unit dose compositions comprising a dosage of vibegron disclosed herein, wherein the unit dosage composition is suitable for oral administration. Oral dosage forms are recognized by those skilled in the art to include, for example, such forms as liquid formulations, tablets, capsules, and gelcaps. In some embodiments, the unit dose compositions are solid dosage forms, such as tablets and capsules. In some embodiments, the unit dose compositions are tablets.

Pharmaceutically acceptable excipients are excipients generally recognized as safe such as lactose, microcrystalline cellulose, starch, calcium carbonate, magnesium stearate, stearic acid, talc, colloidal silicon dioxide, mannitol, croscarmellose sodium, hydroxypropyl cellulose. In some embodiments, the pharmaceutical unit dose composition disclosed herein comprises a diluent, a disintegrant, a binder, and a lubricant. See generally, Remington's Pharmaceutical Sciences, 20th ed., Mack Publishing, Easton PA (2000), which is incorporated herein by reference in its entirety.

In one embodiment, the pharmaceutical unit dose composition disclosed herein comprises mannitol, microcrystalline cellulose, croscarmellose sodium, hydroxypropyl cellulose, and magnesium stearate.

Oral dosage forms can be prepared by standard pharmaceutical manufacturing techniques. Such techniques include, for example, wet granulation, wet milling, fluid bed drying, dry milling, lubrication, tableting, and aqueous film coating.

In some embodiments, the pharmaceutical unit dose compositions of the present disclosure comprise from about 50 mg to about 100 mg of vibegron.

In some embodiments, the pharmaceutical unit dose compositions of the present disclosure comprise from about 55 mg to about 100 mg, from about 60 mg to about 100 mg, from about 65 mg to about 100 mg, from about 70 mg to about 100 mg, from about 75 mg to about 100 mg, from about 80 mg to about 100 mg, from about 85 mg to about 100 mg, from about 90 mg to about 100 mg, or from about 95 mg to about 100 mg of vibegron.

In some embodiments, the pharmaceutical unit dose compositions of the present disclosure comprise from about 50 mg to about 95 mg, from about 50 mg to about 90 mg, from about 50 mg to about 85 mg, from about 50 mg to about 80 mg, from about 50 mg to about 75 mg, from about 50 mg to about 70 mg, from about 50 mg to about 65 mg, from about 50 mg to about 60 mg, or from about 50 mg to about 55 mg of vibegron.

In some embodiments, the pharmaceutical unit dose compositions of the present disclosure comprise from about 60 mg to about 90 mg, from about 65 mg to about 85 mg, or from about 70 mg to about 80 mg of vibegron. In some embodiments, the pharmaceutical unit dose compositions of the present disclosure comprise from 60 mg to 90 mg, from 65 mg to 85 mg, or from 70 mg to 80 mg of vibegron.

In some embodiments, the pharmaceutical unit dose compositions of the present disclosure comprise about 55 mg, about 60 mg, about 65 mg, about 70 mg, about 75 mg, about 80 mg, about 85 mg, about 90 mg, or about 95 mg of vibegron. In some embodiments, the pharmaceutical unit dose compositions of the present disclosure comprise about 75 mg of vibegron. In some embodiments, the pharmaceutical unit dose compositions of the present disclosure comprise 75 mg of vibegron.

In some embodiments, the $AUC_{0-inf}$ after a single dose of vibegron is about 500 ng·hr/mL to about 1800 ng·hr/mL.

In some embodiments, the $C_{max}$ after a single dose of vibegron is about 30 ng/mL to about 200 ng/mL.

In some embodiments, the $T_{max}$ after a single dose of vibegron is about 2 hours to about 3 hours.

In some embodiments, the $T_{1/2}$ after a single dose of vibegron is about 50 hours to about 70 hours.

In some embodiments, after a single dose of vibegron, the $AUC_{0-inf}$ is about 500 ng·hr/mL to about 1800 ng·hr/mL, the $C_{max}$ is about 30 ng/mL to about 200 ng/mL, the $T_{max}$ is about 2 hours to about 3 hours, and the $T_{1/2}$ is about 50 hours to about 70 hours.

In some embodiments, the $AUC_{0-24}$ after multiple doses of vibegron is about 500 ng·hr/mL to about 3000 ng·hr/mL.

In some embodiments, the $C_{max}$ after a single dose of vibegron is about 40 ng/mL to about 400 ng/mL.

In some embodiments, the $T_{max}$ after multiple doses of vibegron is about 1 hour to about 3 hours.

In some embodiments, the $T_{1/2}$ after multiple doses of vibegron is about 70 hours to about 80 hours.

In some embodiments, after multiple doses of vibegron, the $AUC_{0-24}$ is about 500 ng·hr/mL to about 3000 ng·hr/mL, the $C_{max}$ is about 40 ng/mL to about 400 ng/mL, the $T_{max}$ is about 1 hour to about 3 hours, and the $T_{1/2}$ is about 70 hours to about 80 hours.

In-Vitro Assays

Vibegron was tested in several in vitro assays to determine its agonist potency at human $\beta_3$-AR, its selectivity versus the other human β-AR subtypes, and its potency at $\beta_3$-ARs from other species.

Vibegron activity was measured in a functional assay measuring increases in cellular adenylyl cyclase activity in Chinese hamster ovary (CHO) cells stably expressing the human $\beta_3$-AR. The degree of activation relative to a proven full agonist (isoproterenol) was measured along with the compound $EC_{50}$.

Vibegron is a potent and selective agonist of $\beta_3$-AR, with an $EC_{50}$ of 1.1 nM and 84% activation relative to isoproterenol. A small serum shift is observed in the presence of 40% human serum ($EC_{50}$=1.7 nM, 102% activation), consistent with the low plasma protein binding (49% unbound in human) of this compound.

In addition, the selectivity of vibegron for $\beta_3$-AR over $\beta_1$- and $\beta_2$-AR subtypes was determined by testing in CHO cells expressing either $\beta_1$-AR or $\beta_2$-AR. Vibegron is highly selective over $\beta_1$-AR and $\beta_2$-AR versus $\beta_3$-AR, demonstrating >9000-fold selectivity for activation of $\beta_3$-AR over $\beta_1$-AR or $\beta_2$-AR in cell based in vitro functional assays.

The $IC_{50}$ of vibegron was determined in a standard competition binding assay using membranes prepared from cells expressing recombinant $\beta_1$, $\beta_2$ or $\beta_3$-AR. Vibegron has a $\beta_3$-AR $IC_{50}$=193 nM (86 ng/mL) for competition of a non-specific β-AR radiolabeled antagonist $^{125}$I-CYP in a filter binding assay. The relative lack of binding affinity compared to the potent in vitro agonist activity of vibegron at the human $\beta_3$-AR is related to the relative ability of the compound to compete for uncoupled versus coupled receptors which would both be measured by the antagonist binding assay. In addition, the compound does not bind to either $\beta_1$-AR or $\beta_2$-AR as demonstrated in binding competition assays, confirming that the compound is neither an agonist nor an antagonist at these receptors.

Animal Models

Studies of OAB and BPH have used partial bladder outlet obstruction (BOO) animal models in species such as rats, mice, rabbits, guinea pigs, dogs, and pigs. The most common method of inducing BOO in animals is narrowing of the urethral diameter by ligation with thread through a transperitoneal or transperineal incision (See, for example, *Int. J. Urology* (2018) 25, 36-44). Using cystometry, non-voiding contraction (NVC) intervals and contraction pressure can be recorded. Changes in these parameters after the administration of treatments such as $\beta_3$-AR agonists can indicate whether a particular treatment may be useful in the treatment of BPH in humans.

Absorption, Distribution, Metabolism, and Excretion

Vibegron reaches maximum plasma concentrations ($C_{max}$) at approximately 1 to 3 hours after oral administration in healthy volunteers. Mean $C_{max}$ and AUC increase in a greater than dose-proportional manner up to 400 mg. Steady state concentrations were achieved within 7 days of once daily dosing of vibegron. The steady state AUC geometric mean accumulation ratios were ~2 in young male subjects and ~2.8 in elderly subjects (male and female). Vibegron exposures in young Japanese male subjects were modestly increased (<2-fold) following single-dose administration relative to exposures in non-Japanese young male subjects.

Administration of multiple oral doses of 150 mg vibegron with food in healthy middle-aged and elderly females resulted in mean $AUC_{0-24}$ and $C_{max}$ values of ~42% and 59% on Day 1 and ~20% and 43% on Day 14 compared to the same dose in the fasted state.

In a two-part, open-label, single-dose study to investigate the pharmacokinetics of vibegron in patients with hepatic insufficiency the apparent volume of distribution (Vd/F) for vibegron was approximately 9120 L. Vibegron is bound (approximately 49%) to human plasma proteins.

Vibegron is eliminated by a variety of pathways including urinary excretion, biliary excretion, and hepatic metabolism. While CYP3A4 is the predominant CYP responsible for in vitro metabolism, metabolism appears to only play a minor role in the elimination of vibegron. In a mass balance study in healthy subjects, the majority of the recovered dose was eliminated as unchanged vibegron. The mean total recovery of radioactivity in the excreta was 79%, with approximately 59% and 20% of the dose recovered in feces and urine, respectively.

Figure 2:
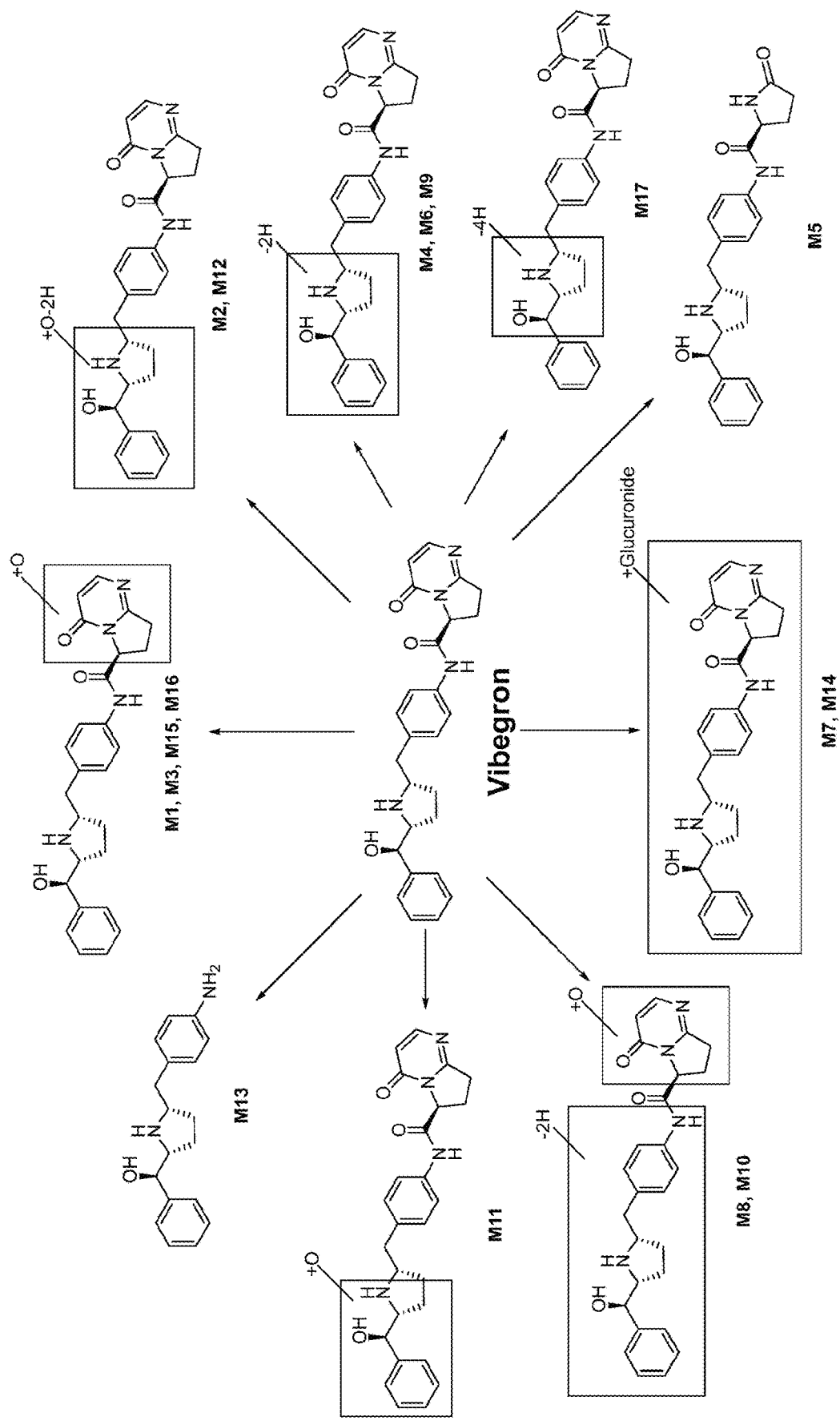
FIG. 2 depicts the chemical structures of vibegron's metabolites.

It was found that most of the vibegron dose was eliminated as the unchanged parent drug. Seven minor metabolites were detected in urine and feces, six of which (M1, M3, M4, M6, M11, and M17) were oxidative metabolites (see FIG. 2). The metabolite M7 is an O-glucuronide conjugate of vibegron. The concentration of [$^{14}$C]vibegron derived radioactivity in plasma had an average $C_{max}$ of 0.3 μM and a $T_{max}$ of 2.5 hr. The radioactive profiles of plasma samples at 2 and 4 hr indicated that ~78% and ~73% of the plasma radioactivity, respectively, was accounted for by the unchanged vibegron, and the O-glucuronide (M7) was the predominant circulating metabolite (~12-14% of the total circulating drug-related material). Two additional minor oxidative metabolites M4 (4-6%) and M17 (6-7%) were also detected in human plasma. The radioactivity in plasma samples at other time points beyond 4 h post dosing was too low to be profiled. The accumulation potential of circulating metabolites in plasma was not estimated due to insufficient data from later time points to enable estimation of half-life.

Vibegron has a terminal $t_{1/2}$ of 59-94 hours in young and elderly subjects. At steady state, the average renal clearance (CLR) in young males ranged from 150 to 187 mL/min across all dose levels, while CLR in elderly subjects (male and female) was slightly less at 127 mL/min. There was a trend of increasing fraction of the dose excreted at steady state ($fe_{0-24hr}$, ss) with increasing dose, reflecting the increase in bioavailability as the dose increased. The $fe_{0-24hr}$, ss was similar in young males and elderly, ~14% at 100 and 150 mg in young males and ~17% at 100 mg in elderly subjects. The mean $fe_{0-24hr}$ and $CL_R$ in young Japanese subjects were similar to what was observed in non-Japanese subjects.

EXAMPLES

Example 1

Vibegron Tablet Formulation

The composition of vibegron tablets (50 mg, 75 mg, and 100 mg) is shown in Table 1.

TABLE 1

Vibegron Tablet Compositions

| Components | Function | Unit Strength | | |
|---|---|---|---|---|
| | | 50 mg mg/tablet | 75 mg mg/tablet | 100 mg mg/tablet |
| Core Tablet | | | | |
| Vibegron | Active | 50.00 | 75.00 | 100.0 |
| Mannitol | Diluent | 20.75 | 31.125 | 41.50 |
| Microcrystalline Cellulose | Diluent | 20.75 | 31.125 | 41.50 |
| Croscarmellose Sodium | Disintegrant | 3.000 | 4.500 | 6.000 |
| Hydroxypropyl Cellulose | Binder | 4.500 | 6.75 | 9.000 |
| Magnesium Stearate | Lubricant | 1.000 | 1.500 | 2.000 |
| Purified Water[1] | Solvent | (35.00-45.00) | (52.5-67.5) | (70.00-90.00) |
| Total Core Weight | | 100.0 | 150.0 | 200.00 |

TABLE 1-continued

Vibegron Tablet Compositions

| Components | Function | Unit Strength | | |
|---|---|---|---|---|
| | | 50 mg mg/tablet | 75 mg mg/tablet | 100 mg mg/tablet |
| Film Coating Suspension | | | | |
| Purified Water[1] | Solvent | (45.00) | (67.50) | (90.00) |
| OPADRY II Green (39K110004) | Colorant | 5.000 | 7.500 | 10.00 |
| Total | | 105.0 | 157.5 | 210.0 |

[1]Removed during processing

Example 2

Pharmacokinetic Data 2.1 Single-Dose Pharmacokinetics

Single-dose pharmacokinetics of vibegron were examined in two double-blind, randomized, placebo-controlled, single rising oral dose Phase 1 studies. All subjects were healthy adults. A summary of the results is presented in Table 2. Following single oral vibegron doses ranging from 2 to 600 mg, the average $t_{max}$ occurred between 0.8 and 3 hours after dosing. Terminal elimination $t_{1/2}$ averaged 43 to 75 hours for all doses from 10 to 600 mg in healthy young male subjects. Systemic exposures were greater than dose proportional up to 600 mg.

Vibegron exposures in Japanese young males were modestly increased relative to exposures in non-Japanese young males. Geometric mean ratios (GMRs; Japanese/non-Japanese) for vibegron $AUC_{0-inf}$ and corresponding 90% CIs decreased with increasing dose, from 1.75 (1.38, 2.23) at 10 mg to 1.17 (0.99, 1.40) at 300 mg. The GMR (Japanese/non-Japanese) and 90% CI for vibegron $C_{max}$ did not appear to be influenced by dose and was 1.75 (1.35, 2.26) pooled across all doses. Median $T_{max}$ values (1 to 3 hours) and harmonic mean apparent terminal $t_{1/2}$ estimates (58 to 71 hours) in the Japanese subjects were similar to those in the non-Japanese subjects. Similar to non-Japanese subjects, $AUC_{0-inf}$ and $C_{max}$ in the Japanese subjects appeared to increase in a greater than dose proportional manner up to 300 mg.

Single-dose pharmacokinetics of 50 mg vibegron in non-Japanese elderly male and female subjects are also presented in Table 2. In elderly male and female subjects, mean $AUC_{0-inf}$ and $C_{max}$ following administration of 50 mg vibegron were ~70% and 60% higher, respectively, relative to corresponding values following 50 mg in young males. $T_{max}$ was similar to that observed in young males (median $T_{max}$=1.0 hr), while the apparent terminal $t_{1/2}$ was slightly longer in elderly relative to young (harmonic mean $t_{1/2}$=92 vs. 52 hr). Vibegron exposures in elderly females were somewhat higher than in elderly males.

TABLE 2

Summary of Selected Single Dose Plasma Vibegron Pharmacokinetic Parameters

| Dose (mg)[a] | N | $AUC_{0-inf}$ (ng · h/mL) | $AUC_{0-24}$ (ng · h/mL) | $C_{max}$ (ng/mL) | $T_{max}$[b] (hr) | $t_{1/2}$[c] (hr) |
|---|---|---|---|---|---|---|
| 2 | 3[d] | —[e] | 0.80 ± 0.33 | 0.28 ± 0.02 | 3.0 (1.0-3.0)[c] | —[e] |
| 5 | 6 | —[e] | 8.31 ± 4.80 | 0.79 ± 0.30 | 1.0 (0.5-6.0) | —[e] |
| 10 | 6 | 70.7 ± 34.9 | 30.0 ± 12.6 | 4.76 ± 4.58 | 2.5 (1.0-6.0) | 43.2 ± 13.0 |
| 10 | 6 | 98.7 ± 27.3 | 31.0 ± 9.33 | 3.34 ± 1.97 | 1.0 (1.0-4.0) | 57.6 ± 39.0 |

TABLE 2-continued

Summary of Selected Single Dose Plasma Vibegron Pharmacokinetic Parameters

| Dose (mg)[a] | N | AUC$_{0-inf}$ (ng · h/mL) | AUC$_{0-24}$ (ng · h/mL) | C$_{max}$ (ng/mL) | T$_{max}$[b] (hr) | t$_{1/2}$[c] (hr) |
|---|---|---|---|---|---|---|
| (Japanese) | | | | | | |
| 20 | 6 | 121 ± 48.9 | 40.0 ± 21.1 | 5.25 ± 4.25 | 0.8 (0.5-6.0) | 64.2 ± 12.6 |
| 50 | 6 | 551 ± 262 | 219 ± 123 | 31.7 ± 35.0 | 2.0 (0.5-6.0) | 52.0 ± 7.8 |
| 50 | 6 | 885 ± 241 | 385 ± 136 | 62.2 ± 20.4 | 3.0 (0.5-3.0) | 64.4 ± 8.7 |
| (Japanese) | | | | | | |
| 50 (Elderly Male and Female) | 12 | 951 ± 300 | 314 ± 119 | 50.2 ± 23.6 | 1.0 (0.5-3.0) | 92.1 ± 15.9 |
| 100 | 6 | 1890 ± 698 | 845 ± 401 | 142 ± 108 | 2.0 (1.0-4.0) | 72.8 ± 10.8 |
| 100 (Japanese) | 6 | 1770 ± 418 | 920 ± 300 | 190 ± 123 | 2.5 (0.5-4.0) | 57.6 ± 12.0 |
| 150 | 6 | 2270 ± 911 | 1050 ± 551 | 195 ± 185 | 1.0 (1.0-6.0) | 60.5 ± 10.5 |
| 200 | 18 | 3630 ± 1110 | 1740 ± 748 | 274 ± 138 | 1.0 (1.0-4.0) | 75.3 ± 9.1 |
| 200 (Japanese) | 6 | 5200 ± 791 | 3090 ± 569 | 516 ± 200 | 2.0 (0.5-4.0) | 58.4 ± 9.0 |
| 300 | 6 | 7380 ± 1410 | 4427 ± 996 | 618 ± 231 | 2.5 (2.0-3.0) | 63.4 ± 3.0 |
| 300 (Japanese) | 6 | 6270 ± 1570 | 4050 ± 1240 | 733 ± 210 | 2.0 (1.0-4.0) | 59.7 ± 9.2 |
| 450 | 6 | 9157 ± 1850 | 5510 ± 1440 | 645 ± 165 | 3.0 (0.5-6.0) | 60.0 ± 9.4 |
| 600 | 5 | 15500 ± 3450 | 10900 ± 2770 | 1330 ± 529 | 3.0 (2.0-6.0) | 60.5 ± 5.2 |

Concentration data converted from molar to ng/mL (molecular weight of vibegron = 444.5)
[a]Dosed in healthy young males unless otherwise indicated
[b]Median (minimum-maximum)
[c]Harmonic mean ± Pseudo SD
[d]Only 3 of 6 subjects had any concentrations above the limit of quantitation at the 2 mg dose. Summary statistics for C$_{max}$, T$_{max}$ and AUC$_{0-24}$ are based only on data from these subjects.
[e]The duration of sampling was too short for 2 and 5 mg, precluding an accurate determination of the apparent terminal t$_{1/2}$ and AUC$_{0-inf}$.

2.2 Multiple-Dose Pharmacokinetics

The multiple-dose pharmacokinetics of vibegron were examined in healthy non-Japanese young male subjects, middle-aged male and female subjects, and elderly male and female subjects, and in healthy Japanese young male subjects, and elderly male and female subjects in two randomized, double-blind, placebo-controlled, multiple rising dose Phase 1 studies. Non-Japanese subjects received multiple doses ranging from 25 to 400 mg for 7 to 28 days, whereas Japanese subjects received multiple doses of 50 to 200 mg for 14 days. Pharmacokinetic results after 14 days of dosing are summarized in Table 3.

On average, females tend to have 50% higher exposures (AUC) compared with males, regardless of age. Steady state AUC and C$_{max}$ values following QD doses of 100 mg vibegron in elderly subjects were about 1.7-fold and 1.3-fold higher, respectively, compared to young males.

The GM C$_{max}$ and AUC accumulation ratio were 1.78 and 1.84 for Japanese subjects at the 200 mg dose level. On average, steady state exposures in the Japanese young male subjects were ~30% higher than those in the young male non-Japanese subjects; differences in exposure were statistically significant. The GMR (Japanese/non-Japanese) and corresponding 90% CI of vibegron AUC and C$_{max}$ pooled across doses were 1.27 (1.09, 1.48) and 1.33 (1.06, 1.67), respectively.

On average, steady state exposures on Day 14 in elderly male and female Japanese subjects were 35% higher than those in elderly male and female non-Japanese subjects; differences in exposure were statistically significant. Day 14 GMR (Japanese/non-Japanese) and corresponding 90% CI of vibegron AUC$_{0-24}$ and C$_{max}$ for the elderly panel were 1.35 (1.09, 1.68) and 1.82 (1.32, 2.51), respectively.

TABLE 3

Summary of Selected Multiple Dose Plasma Vibegron Pharmacokinetic Parameters

| Dose (mg)[a] | N | AUC$_{0-24}$ (ng · h/mL) | C$_{max}$ (ng/mL) | C$_{trough}$ (ng/mL) | T$_{max}$[b] (hr) | t$_{1/2}$[c] (hr) |
|---|---|---|---|---|---|---|
| 25 | 6 | 164 ± 25.9 | 15.6 ± 6.93 | 5.07 ± 0.711 | 1.0 (0.5-2.0) | 94.0 ± 9.60 |
| 50 | 6 | 507 ± 176 | 41.5 ± 12.3 | 15.2 ± 5.07 | 2.5 (0.5-6.0) | 77.2 ± 8.9 |
| 50 (Japanese) | 5 | 613 ± 296 | 56.9 ± 34.2 | 16.5 ± 6.05 | 3.0 (0.5-3.0) | 69.4 ± 6.6 |
| 100 | 6 | 1280 ± 529 | 169 ± 80.9 | 31.9 ± 11.5 | 1.0 (0.5-4.0) | 79.7 ± 11.5 |
| 100 (Japanese) | 6 | 1710 ± 542 | 180 ± 111 | 41.0 ± 11.0 | 2.0 (2.0-4.0) | 56.8 ± 19.2 |
| 100 (Elderly Male and Female) | 12 | 2230 ± 671 | 224 ± 92.0 | 54.2 ± 15.3 | 1.0 (0.5-6.0) | 88.4 ± 10.7 |
| 100 (Elderly Japanese) | 12 | 2920 ± 693 | 393 ± 165 | 57.3 ± 12.2 | 1.5 (0.5-4.0) | 75.1 ± 3.9 |

TABLE 3-continued

Summary of Selected Multiple Dose Plasma Vibegron Pharmacokinetic Parameters

| Dose (mg)[a] | N | AUC$_{0-24}$ (ng · h/mL) | C$_{max}$ (ng/mL) | C$_{trough}$ (ng/mL) | T$_{max}$[b] (hr) | t$_{1/2}$[c] (hr) |
|---|---|---|---|---|---|---|
| 150 | 6 | 2285 ± 1140 | 305 ± 215 | 54.2 ± 16.6 | 1.5 (0.5-4.0) | 79.2 ± 9.2 |
| 150 (Middle-Aged Male) | 9 | 2170 ± 452 | 293 ± 67.1 | 46.2 ± 8.50 | 1.0 (0.5-3.0) | 72.7 ± 16.1[d] |
| 150 (Middle-Aged Female) | 9 | 3180 ± 925 | 246 ± 139 | 62.7 ± 12.4 | 2.0 (1.0-4.0) | 83.1 ± 17.2 |
| 200 | 6 | 3200 ± 1120 | 313 ± 168 | 61.8 ± 12.4 | 2.0 (1.0-3.0) | 64.7 ± 6.5 |
| 200 (Japanese) | 6 | 4370 ± 618 | 631 ± 154 | 62.2 ± 9.07 | 1.0 (0.5-6.0) | 59.5 ± 1.9 |
| 300 | 18 | 6980 ± 1040 | 733 ± 164 | 128 ± 23.6 | 2.0 (2.0-3.0) | 61.7 ± 7.3 |
| 400 | 6 | 10500 ± 2140 | 1400 ± 257 | 189 ± 54.7 | 1.5 (1.0-3.0) | 58.9 ± 5.9 |

Concentration data converted from molar to ng/mL (molecular weight of vibegron = 444.5)
[a]Dosed in healthy young males unless otherwise indicated
[b]Median (minimum-maximum)
[c]Harmonic mean ± Pseudo SD
[d]t$_{1/2}$ determined after 28 days of dosing

2.3 Bioavailability and Bioequivalence

Five Phase 1 studies were conducted using a capsule formulation of vibegron, while seven Phase 1 studies and one Phase 2b study used a tablet formulation. An open-label randomized, 2-period, crossover PK study in healthy male subjects age 18 to 45 years compared single-dose pharmacokinetics of the capsule (1×150 mg capsule) and tablet (3×50 mg tablets) formulations of vibegron.

The tablet formulation provided comparable exposures to the capsule formulation as demonstrated in Table 4. T$_{max}$ and the apparent terminal t$_{1/2}$ were also similar between the two formulations.

TABLE 4

A Summary of the Effect of Formulation on the Pharmacokinetics of 150 mg Vibegron in Healthy Male Subjects

| Pharmacokinetic Parameter | Geometric Least Squares Mean (95% CI) | | GMR | 90% CI |
|---|---|---|---|---|
| | Capsule[a] | Tablet[b] | | |
| AUC$_{0-inf}$ (ng · hr/mL) | 2840 (2512, 3220) | 2660 (2350, 3010) | 0.94 | (0.87, 1.00) |
| C$_{max}$ (ng/mL) | 237 (190, 295) | 213 (172, 264) | 0.90 | (0.75, 1.08) |

Concentration data converted from molar to ng/mL (molecular weight of vibegron = 444.5)
GMR = Geometric least-squares mean ratio of tablet to capsule
[a]1 × 150 mg vibegron capsule
[b]3 × 50 mg vibegron tablets An open-label, single-dose, randomized, two-period, two-treatment, two-sequence, crossover Phase 1 study evaluated the relative bioequivalence of two types of tablets with slightly different composition: aqueous tablet (test) and non-aqueous tablet (reference).

TABLE 5

A Summary of the Effect of Formulation on the Pharmacokinetics of 50 mg Vibegron in Healthy Male and Female Subjects

| Pharmacokinetic Parameter | Geometric Least Squares Mean (95% CI) | | GMR (%) | 90% CI |
|---|---|---|---|---|
| | Reference Tablet[a] | Test Tablet[b] | | |
| AUC$_{0-inf}$ (ng · hr/mL) | 671 (529, 853) | 671 (547, 827) | 100.2 | (91.6, 109.5.) |
| C$_{max}$ (ng/mL) | 38.0 (27.8, 52.1) | 41.0 (30.0, 56.1) | 107.7 | (87.4, 132.7) |

Concentration data converted from molar to ng/mL (molecular weight of vibegron = 444.5)
GMR = Geometric least-squares mean ratio of Phase 3 tablet to Phase 2 tablet
[a]Non-aqueous tablet (PMF1)
[b]Aqueous (PMFII)

2.4 Effect of Food on Oral Absorption

The effect of food on the single dose pharmacokinetics of vibegron 50 mg was evaluated in healthy non-Japanese and Japanese young males in two randomized, double-blind, placebo-controlled, rising single-dose Phase 1 studies, while the effect of food on multiple dose pharmacokinetics of vibegron 150 mg in middle-aged females was evaluated in a randomized, double-blind, placebo-controlled, multiple rising dose Phase 1 study. A summary of the pharmacokinetic results are listed in Table 6.

Administration of 50 mg vibegron with a high-fat meal in non-Japanese young males resulted in 46% and 67% reductions in AUC$_{0-inf}$ and C$_{max}$, respectively, and a delay in T$_{max}$ of ~1 hour compared to administration in the fasted state. Administration of 50 mg vibegron with a standard Japanese breakfast to Japanese young males resulted in 37% and 52% reductions in AUC$_{0-inf}$ and C$_{max}$, respectively, roughly similar to findings in non-Japanese male subjects administered the same dose with a high fat meal.

Administration of multiple oral doses of 150 mg vibegron with food in healthy middle-aged females resulted in 20% and 47% reductions in mean AUC$_{0-24hr}$ and C$_{max}$, respectively, on Day 14 compared to the same dose in the fasted state. T$_{max}$ at steady state was delayed in the fed state compared to the fasted state (6.0 vs. 2.0 hr).

TABLE 6

Summary of Food Effect on Vibegron Pharmacokinetic Parameters
following Single and Multiple Dose Administration in the Fed and
Fasted State to Healthy Japanese and Non-Japanese Young Male
Subjects, and to Healthy Non-Japanese Middle-Aged Female Subjects

| Single Dose (mg) in Young Males | N | Pharmacokinetic Parameters[a] | | | |
|---|---|---|---|---|---|
| | | $AUC_{0\text{-}inf}$ (ng·h/mL) | $AUC_{0\text{-}24}$ (ng·h/mL) | $C_{max}$ (ng/mL) | $T_{max}$[b] (hr) |
| 50 (Non-Japanese, fed) | 6 | 316 ± 127 | 90.7 ± 22.9 | 7.6 ± 2.27 | 3.0 (2.0-6.0) |
| 50 (Non-Japanese, fasted) | 6 | 551 ± 262 | 219 ± 123 | 31.7 ± 35.0 | 2.0 (0.5-6.0) |
| 50 (Japanese, fed) | 6 | 605 ± 222 | 226 ± 112 | 36.2 ± 33.3 | 1.5 (0.5-3.0) |
| 50 (Japanese, fasted) | 5 | 885 ± 241 | 385 ± 136 | 62.2 ± 20.4 | 3.0 (0.5-3.0) |

| Multiple Dose (mg) in Non-Japanese Middle-Aged Females | N | Pharmacokinetic Parameters[a,c] | | | |
|---|---|---|---|---|---|
| | | $AUC_{0\text{-}24}$ (ng·h/mL) | $C_{max}$ (ng/mL) | $C_{trough}$ (ng/mL) | $T_{max}$[b] (hr) |
| 150 (Fed) | 6 | 2540 ± 334 | 185 ± 32.3 | 65.3 ± 7.87 | 6.0 (3.0-6.0) |
| 150 (Fasted) | 9 | 3180 ± 925 | 346 ± 139 | 62.7 ± 12.4 | 2.0 (10-4.0) |

Concentration data converted from molar to ng/mL (molecular weight of vibegron = 444.5)
[a]Geometric mean (CV %)
[b]Median (minimum-maximum)
[c]PK parameters obtained at day 14 of vibegron dosing 2.5 Pharmacokinetics in the Target Disease Population A randomized, double-blind, placebo- and active-controlled, parallel-group two-part Phase 2b study in patients with OAB measured sparse vibegron trough concentrations ($C_{trough}$) only; the mean (±SD) $C_{trough}$ of vibegron 50 mg and 100 mg QD were 27.4 (±18.3) ng/mL and 73.6 (±65.5) ng/mL, respectively. Mean (±SD) $C_{trough}$ of vibegron 50 mg in healthy young men was 15.2 (±5.07) ng/mL. Mean (±SD) $C_{trough}$ values of vibegron 100 mg ranged from 31.9 (±11.5) in healthy young men to 54.2 (±15.3) in healthy elderly.

Example 3

Pharmacokinetics in Special Populations
3.1 Effect of Age

Vibegron exposures were evaluated in young (18 to 45 years), middle-aged (46 to 64 years) and elderly (65 to 85 years) males and females. Although exposures were similar in middle-aged males when compared to young males, plasma concentrations were higher in elderly compared to middle-aged and young subjects. After a single 50 mg dose, vibegron $AUC_{0\text{-}inf}$ and $C_{max}$ were 70% and 60% higher, respectively in elderly subjects compared with young subjects. Elimination $t_{1/2}$ was longer in the elderly at 92 hours compared to 52 hours in young subjects in a randomized, double-blind, placebo-controlled, rising single-dose study. Steady state vibegron $AUC_{0\text{-}24h}$ and $C_{max}$ values were ~1.7- fold and ~1.3-fold greater, respectively, in the elderly compared with young males in a randomized, double-blind, placebo-controlled, multiple rising dose study. Furthermore, the steady state AUC geometric mean accumulation ratios were ~2 in young males and ~2.8 in the elderly. In elderly Japanese, $AUC_{0\text{-}24}$ and $C_{max}$ were increased by ~35% and 82%, respectively compared to elderly non-Japanese.

3.2 Effect of Gender

The effect of gender on steady-state vibegron exposures after 100 or 150 mg doses was evaluated in a randomized, double-blind, placebo-controlled, multiple rising dose study. Vibegron plasma concentrations were similar in middle-aged males when compared to young males; however, exposures were slightly higher in middle-aged females compared to middle-aged males (~1.5-fold higher steady state AUC in middle-aged females), which was also observed when comparing exposures in elderly females to those in elderly males.

3.3 Effect of Renal Impairment

The pharmacokinetics of single dose vibegron 100 mg in 24 patients with impaired renal function (8 severe, 8 moderate, and 8 mild) were compared to 8 healthy control subjects in an open-label, single-dose PK study. A summary of the pharmacokinetic parameters and a statistical comparison between patients with varying degrees of renal impairment and their healthy matched subjects are presented in Table 7.

Vibegron $AUC_{0-inf}$ in patients with mild (eGFR≥60 to <90 mL/min/1.73 m2), moderate (eGFR≥30 to <60 mL/min/1.73 m2), and severe (eGFR<30 mL/min/1.73 m2 but not on dialysis) renal impairment were 49%, 106%, and 83% higher, respectively, compared to healthy matched control subjects. Vibegron $C_{max}$ in mild, moderate, and severe renal impairment patients were 96%, 68%, and 42% higher, respectively, compared to healthy matched control subjects. In summary, increasing degree of renal impairment was associated with an increase in vibegron $AUC_{0-inf}$ with no clear trend observed in $C_{max}$. Decreasing renal function was associated with lower clearance. The relationship between clearance and renal function was modeled using linear regression. Based on the slope from the regression, CL/F was found to increase ~0.8% per one mL/min/1.73 m2 increase in eGFR. Based on this linear relationship, the CL/F ratio for mild, moderate, and severe populations relative to healthy subjects was predicted to be 0.81, 0.64, and 0.50, respectively. Corresponding predicted ratios for AUC were 1.24, 1.57, and 2.00. Modeling the relationship between CL/F and creatinine Clearance yielded similar results. Renal clearance (CLR) and the fraction of dose excreted in urine over the 48-hour collection interval (fe[urine]48 hr) decreased with increasing degree of renal impairment. Patients with mild, moderate, and severe renal impairment had reduced CLR by 39%, 65%, and 82%, respectively, compared to healthy matched control subjects. The fe[urine] 48 hr was comparable between mild renal impairment patients (8.5%) and healthy matched controlled subjects (7.9%) and was 5.5% and 2.1% in moderate and severe renal impairment patients, respectively.

TABLE 7

Summary of Vibegron 100 mg Pharmacokinetic Parameters in Patients with Severe, Moderate and Mild Renal Impairment and Healthy Matched Control Subjects

| Pharmacokinetic Parameter | N | Geometric Least Squares Mean (95% CI) | | | |
|---|---|---|---|---|---|
| | | Severe Renal Impairment | Moderate Renal Impairment | Mild Renal Impairment | Healthy Matched Control Subjects |
| $AUC_{0-inf}$ (ng · hr/mL) | 8 | 2820 (2200, 3610) | 3170 (2500, 4030) | 2290 (1800, 2920) | 1540 (1180, 2010) |
| $C_{max}$ (ng/mL) | 8 | 152 (103, 225) | 180 (123-262) | 210 (144, 308) | 107 (70.8, 162) |
| CL/F (L/hr) | 8 | 35.5 (27.68, 45.53) | 31.5 (24.80, 40.06) | 43.6 (34.23, 55.61) | 64.9 (49.87, 84.47) |
| $T_{max}{}^a$ (hr) | 8 | 0.5 (0.5-4.0) | 1.3 (0.5-3.0) | 1.0 (0.5-3.0) | 1.5 (0.5-4.0) |
| Apparent terminal $t_{1/2}{}^b$ (hr) | 8 | 131 (10.0) | 108 (21.0) | 96.2 (11.5) | 98.8 (13.9) |
| $CL_R{}^b$ (L/hr) | 8 | 1.9 (30.9) | 3.6 (34.5) | 6.3 (31.1)$^c$ | 10.4 (20.2) |
| Fe[urine] 48 hr$^b$ (%) | 8 | 2.1 (57.6) | 5.5 (53.2) | 8.5 (43.9)$^c$ | 7.9 (43.0) |

| Comparison | GMR (90% CI) | | |
|---|---|---|---|
| | $AUC_{0-inf}$ | $C_{max}$ | CL/F |
| Patients with Severe Renal Impairment/Healthy Matched Control Subject | 1.83 (1.36, 2.46) | 1.42 (0.89, 2.27) | 0.55 (0.41, 0.74) |
| Patients with Moderate Renal Impairment/ Healthy Matched Control Subject | 2.06 (1.55, 2.74) | 1.68 (1.07, 2.63) | 0.49 (0.36, 0.65) |
| Patients with Mild Renal Impairment/Healthy Matched Control Subject | 1.49 (1.11, 2.00) | 1.96 (1.23, 3.13) | 0.67 (0.50, 0.90) |

Concentration data converted from molar to ng/mL (molecular weight of vibegron = 444.5)
CI = confidence interval;
GMR = Geometric least-squares mean ratio between treatment populations
$^a$Median (minimum-maximum)
$^b$Geometric mean (percent geometric coefficient of variation)
$^c$N = 7

3.4 Effect of Hepatic Impairment

The pharmacokinetics of a single dose of vibegron 100 mg were evaluated in 8 patients with moderate hepatic impairment (Child-Pugh Score of 7 to 9) and 8 healthy subjects matched for age, gender and BMI in a two-part, open-label, single-dose Phase 1 study. A statistical comparison of vibegron pharmacokinetic parameters is presented in Table 8. The $AUC_{0-inf}$ and $C_{max}$ GMRs (90% CI) for moderate hepatic impaired patients and healthy control subjects were 1.27 (0.96, 1.67) and 1.35 (0.88, 2.06), respectively suggesting that moderate hepatic impairment did not have a clinically important effect on the exposure of vibegron.

TABLE 8

Summary of Vibegron 100 mg Pharmacokinetic Parameters in Patients with Moderate Hepatic Impairment and Healthy Matched Control Subjects

| Pharmacokinetic Parameter | N | Geometric Least Squares Mean (95% CI) | | GMR | 90% CI |
|---|---|---|---|---|---|
| | | Moderate Hepatic Impairment | Healthy Matched Control Subjects | | |
| $AUC_{0-inf}$ (ng · hr/mL) | 8 | 1820 (1440, 2300) | 1440 (1140, 1810) | 1.27 | (0.96, 1.67) |
| $C_{max}$ | 8 | 168 | 125 | 1.35 | (0.88, 2.06) |

TABLE 8-continued

Summary of Vibegron 100 mg Pharmacokinetic Parameters in
Patients with Moderate Hepatic Impairment and Healthy Matched
Control Subjects

| Pharmaco-kinetic Parameter | N | Geometric Least Squares Mean (95% CI) | | GMR | 90% CI |
|---|---|---|---|---|---|
| | | Moderate Hepatic Impairment | Healthy Matched Control Subjects | | |
| (ng/mL) | | (118, 240) | (87.6, 178) | | |
| $T_{max}^{a}$ (hr) | 8 | 1.0 (0.5-3.0) | 1.5 (0.5-4.0) | | |
| Apparent terminal $t_{1/2}^{b}$ (hr) | 8 | 94.5 (8.88%) | 92.5 (9.37%) | | |
| $CL/F^{b}$ (L/hr) | 8 | 56.0 (31.2%) | 68.3 (36.0%) | | |
| $Vz/F^{b}$ (L) | 8 | 7640 (33.3%) | 9120 (30.7%) | | |

Concentration data converted from molar to ng/mL (molecular weight of vibegron = 444.5)
CI = confidence interval;
GMR = Geometric least-squares mean ratio between treatment populations
[a]Median (minimum-maximum)
[b]Geometric mean (percent geometric coefficient of variation)

3.5 Drug Interaction Studies

Four drug interaction studies evaluating vibegron in combination with six compounds were conducted. Table 9 summarizes the effect of ketoconazole, diltiazem or tolterodine on the pharmacokinetics of vibegron. Table 10 summarizes the effect of vibegron on the pharmacokinetics of digoxin, ethinyl estradiol, levonorgestrel or tolterodine.

Multiple doses of the strong CYP3A4/P-gp inhibitor, ketoconazole 200 mg and the moderate CYP3A4/P-gp inhibitor, diltiazem 240 mg were evaluated in combination with a single dose of vibegron 100 mg. GM vibegron $AUC_{0-inf}$ and $C_{max}$ increased 2.08-fold and 2.22 fold, respectively in the presence of multiple doses of 200 mg ketoconazole. GM vibegron $AUC_{0-inf}$ and $C_{max}$ increased 63% and 68%, respectively in the presence of multiple doses of 240 mg or 180 mg diltiazem. The GM $t_{1/2}$ was 75, 75.4, and 80.2 hours, respectively when vibegron was dosed alone, with diltiazem or with ketoconazole, respectively. This lack of increase of vibegron $t_{1/2}$ in the presence of ketoconazole or diltiazem suggests that the interaction occurred primarily in the absorption phase. However, these interactions are not expected to be clinically significant. Tolterodine ER 4 mg had no effect on the pharmacokinetics of vibegron.

Multiple doses of vibegron were evaluated in combination with the p-gp substrate, digoxin. The 90% CI for the $AUC_{0-inf}$ GMR of digoxin when co-administered with vibegron was contained within the 80-125% bioequivalence range suggesting that vibegron does not influence digoxin pharmacokinetics to a clinically significant degree. The pharmacokinetics of ethinyl estradiol (EE) and levonorgestrel (LNG), two common components of oral contraceptives were not altered by multiple doses of vibegron. The 90% CI for the GMR (EE/LNG+vibegron to EE/LNG alone) for the AUC and $C_{max}$ of EE were contained within 0.8 and 1.25. Although, LNG AUC and $C_{max}$ increased 18 to 21% in the presence of multiple doses of vibegron, these increases were not considered to be clinically significant. No clinically meaningful pharmacokinetic interaction occurs when vibegron 100 mg or 150 mg is co-administered with tolterodine ER 4 mg.

TABLE 9

Change in Pharmacokinetic Parameters of Vibegron in the Presence of Co-Administered Medication (Conmed)

| Conmed | Dose of Conmed (mg) | Dose of Vibegron (mg) | n | | Geometric Mean (95% CI) | | Ratio (with/without conmed) of Vibegron Pharmacokinetic Parameters; No Effect = 1.00 | |
|---|---|---|---|---|---|---|---|---|
| | | | | | Vibegron alone | Conmed + Vibegron | GMR | (90% CI) |
| Ketoconazole | 200 mg every 12 hours | 100 mg single dose | 10 | AUC | 1370 (788, 2380) | 2850 (2100, 3870) | 2.08 | (1.66, 2.61) |
| | | | | $C_{max}$ | 113 (53.1, 241) | 251 (167, 379) | 2.22 | (1.50-3.28) |
| Diltiazem ER | 240 mg QD | 100 mg single dose | 12 | AUC | 1330 (1130, 1570) | 2170 (1990, 2480) | 1.63 | (1.44, 1.85) |
| | | | | $C_{max}$ | 99.8 (73.8, 135) | 167 (129-217) | 1.68 | (1.41, 1.99) |
| Tolterodine ER | 4 mg QD | 100 mg QD | 24 | AUC | 1662 (1382, 2000) | 1791[a] (1533, 2094) | 1.08 | (0.94, 1.23) |
| | | | | $C_{max}$ | 158 (111, 224) | 163[a] (127, 209) | 1.03 | (0.74, 1.43) |
| | | 150 mg QD | 23 | AUC | 2783 (2409, 3218) | 3102[a] (2787, 3463) | 1.12 | (0.98, 1.27) |
| | | | | $C_{max}$ | 269 (210, 344) | 304[a] (260, 357) | 1.13 | (0.90, 1.42) |

[a]N = 12

Concentration data converted from molar to ng/mL (molecular weight of vibegron = 444.5)

TABLE 10

Drug Interactions: Change in Pharmacokinetic Parameters of Co-Administered Drug (Conmed) in the Presence of Vibegron

| Conmed | Dose of Conmed (mg) | Dose of Vibegron (mg) | n | | Geometric Mean (95% CI) of Conmed | | Ratio (with/without Vibegron) of Conmed Pharmacokinetic Parameters; No Effect = 1.00 | |
|---|---|---|---|---|---|---|---|---|
| | | | | | Conmed alone | Conmed + Vibegron | GMR | (90% CI) |
| Digoxin | 0.25 mg single dose | 100 mg QD | 18 | AUC | 16600 (14600, 19200) | 1840$^a$ (16200, 21000) | 1.11 | (1.03, 1.19) |
| | | | | $C_{max}$ | 1160 (965, 1400) | 1410 (1170, 1700) | 1.21 | (1.09, 1.35) |
| Oral Contraceptive | 0.03 mg EE single dose | 100 mg QD | 18 | AUC | 810 (713, 920) | 838 (734, 958) | 1.04 | (1.00, 1.07) |
| | | | | $C_{max}$ | 71.9 (62.3, 82.9) | 68.8 (60.5, 78.3) | 0.96 | (0.90, 1.02) |
| | 0.15 mg LNG single dose | | | AUC | 31000 (26800, 35900) | 37600 (32300, 43700) | 1.21 | (1.13, 1.30) |
| | | | | $C_{max}$ | 2070 (1770, 2420) | 2440 (2100, 2840) | 1.18 | (1.09, 1.27) |
| Tolterodine ER | 4 mg QD | 100 mg QD | 12 | AUC | 28.37 (15.03, 53.56) | 30.66 (16.24, 57.89) | 1.08 | (0.97, 1.21) |
| | | | | $C_{max}$ | 2.28 (1.32, 3.96) | 2.57 (1.48, 4.45) | 1.12 | (1.00, 1.26) |
| | | 150 mg QD | | AUC | 13.25$^a$ (7.39, 23.76) | 10.80 (6.02, 19.38) | 1.23 | (1.11, 1.35) |
| | | | | $C_{max}$ | 1.26$^a$ (0.66, 2.39) | 0.92 (0.48, 1.75) | 1.37 | (1.20, 1.57) |

GMR = Geometric Means Ratio; CI = confidence interval; EE = ethinyl estradiol; LNG = levonorgestrel
Concentration data converted from molar to ng/mL (molecular weight of vibegron = 444.5)
$^a$N = 17
$^b$N = 11

A pharmacokinetic study evaluating the drug interaction of vibegron and metoprolol succinate, a moderately sensitive CYP2D6 substrate, was also completed. All subjects were healthy adults. A summary of the preliminary results is presented in Table 11. Subjects received a single dose of metoprolol succinate 100 mg with warfarin 10 mg on day 1, vibegron 75 mg QD on days 8-16, a dose of vibegron 75 mg concomitantly with a dose of metoprolol succinate 100 mg and warfarin 10 mg on day 17, and vibegron 75 mg QD on days 18-23. Study treatments were well tolerated, with no evidence of increase of adverse events during combination administration with vibegron. Metoprolol geometric mean Cmax and AUC values increased slightly in the presence of vibegron. However, the elimination half-life of metoprolol was similar alone and with vibegron, suggesting CYP2D6 was unlikely inhibited. Plasma concentration over time for metoprolol alone was similar to the profile seen with metoprolol and vibegron (FIG. 3).

TABLE 11

Pharmacokinetic Parameters of Vibegron in Combination with Metoprolol

| Pharmacokinetic Parameter | Metoprolol + Vibegron (N = 24) GM (% CV) | Metoprolol (n = 24) GM (% CV) | Ratio: Metoprolol + Vibegron/Metoprolol alone Ratio of GLS Mean | 90% CI |
|---|---|---|---|---|
| $AUC_{0-\infty}$ (ng · hr/mL) | 539 (79.4) | 384 (74.7) | 1.40 | (1.30 to 1.52) |
| $C_{max}$ (ng/mL) | 32.7 (64.7) | 21.9 (67.6) | 1.49 | (1.35 to 1.65) |
| $t_{1/2}$ (hr) | 10.9 (52.8) | 9.5 (45.2) | NA | |

Metoprolol 100 mg;
Vibegron 75 mg
AUC = area under the concentration time curve from 0 to infinity;
$C_{max}$ = maximum concentration;
$t_{1/2}$ = half-life;
GM = geometric mean;
CV = coefficient of variation;
GLS = geometric least squares;
CI = confidence interval 3.6 Effect on QT Interval Prolongation The effect of vibegron on QTc interval was evaluated in a single oral dose study. Fifty-two healthy subjects received a single dose of 400 mg vibegron, a single dose of vibegron 200 mg, a single dose of moxifloxacin 400 mg and a single dose of placebo to match vibegron.

The 400 mg dose of vibegron resulted in a maximum LS mean difference (90% CI) from placebo in QTcF of 4.60 (2.71, 6.48) msec at 1 hour post dose. A similar result was noted in QTcF after the 200 mg single dose where the maximum LS mean difference (90% CI) from placebo was 4.98 (3.07, 6.88) msec at 1 hour post dose. The upper limits of the 90% CIs of all of the mean differences fell below the target of 10 msec. (Table 12). A statistically significant effect of moxifloxacin on QTcF was observed.

The GM (CV %) $C_{max}$ and $AUC_{0-23.5hr}$ achieved following a single 200 mg dose were 366 (50.4) ng/mL and 2270 (37.3) ng·h/mL respectively. Vibegron $C_{max}$ was 1.63-fold the value obtained in elderly subjects receiving multiple doses of 100 mg in a double-blind, randomized, placebo-controlled, alternating (Panels A and B), multiple-period, single rising oral dose Phase 1 study, while the AUC was similar. The GM (CV %) $C_{max}$ and $AUC_{0-23.5hr}$ achieved following a single dose of 400 mg were 1020 (39.9) ng/mL and 6450 (34.0) ng·h/mL respectively. These $C_{max}$ and $AUC_{0-23.5hr}$ values are 4.55-fold and 2.89-fold the values obtained in elderly subjects receiving multiple doses of vibegron 100 mg.

Target PK exposures at both the 200 mg and 400 mg dose levels were achieved. The steady state $C_{max}$ and $AUC_{0-24hr}$ values achieved in elderly female subjects at the highest clinical dose of 100 mg were 278 ng/mL and 2620 ng·h/mL, respectively.

proof of concept study for concomitant dosing of vibegron with tolterodine ER 4 mg. Approximately 980 subjects in Part 1 were equally randomized in a double-blind fashion to one of seven treatment arms: vibegron 3 mg, 15 mg, 50 mg, or 100 mg once daily for 8 weeks; tolterodine ER 4 mg once daily for 8 weeks; placebo once daily for 8 weeks; or vibegron 50 mg with tolterodine ER 4 mg for 4 weeks followed by vibegron 50 mg for 4 weeks. Part 2 was designed to continue to assess the safety and efficacy of concomitant dosing. In Part 2, 408 subjects were randomized in a double-blind fashion to one of four treatment arms in a 2:2:2:1 ratio: vibegron 100 mg, tolterodine ER 4 mg, vibegron 100 mg with tolterodine ER 4 mg, or placebo once daily for 4 weeks. Subjects in both Part 1 and Part 2 had the option of enrolling in a 1-year extension. Participants were required to keep a voiding diary, recording the occurrence of each strong urge, total incontinence, and urge incontinence episode. Efficacy data for Part 1 and Part 2 are summarized herein.

At baseline, subjects must have had an average number of micturitions≥8 per diary day in the Voiding Diary. In addi-

TABLE 12

Statistical Comparison for QTcF Change from Baseline Difference from Placebo (Vibegron - Placebo) by Treatment and Time Point Relative to the Administration of a Dose of 400 mg Vibegron, a Dose of 200 mg of Vibegron, and a Single Dose of Placebo to Vibegron

| Hour | Single Dose of 400 mg Vibegron (msec) | | | Single Dose of 200 mg Vibegron (msec) | | | Single Dose of Placebo to Vibegron (msec) | | |
|---|---|---|---|---|---|---|---|---|---|
| | N | LS Mean | 95% CI | N | LS Mean | 95% CI | N | LS Mean | 95% CI |
| 0.5 hour | 52 | 2.37 | (0.66, 4.07) | 50 | 1.90 | (0.16, 3.63) | 50 | −0.00 | (−2.74, 0.73) |
| 1 hour | 52 | 4.49 | (2.78, 6.19) | 50 | 4.87 | (3.13, 6.60) | 50 | −0.11 | (−1.84, 1.63) |
| 2 hour | 52 | 0.73 | (−0.97, 2.43) | 50 | 2.06 | (0.32, 3.79) | 50 | −0.08 | (−1.81, 1.65) |
| 3 hour | 52 | −0.30 | (−2.00, 1.41) | 50 | 1.14 | (−0.59, 2.88) | 50 | 0.74 | (−0.99, 2.47) |
| 4 hour | 52 | −2.53 | (−4.23, −0.82) | 50 | −0.40 | (−2.14, 1.33) | 50 | 0.43 | (−1.30, 2.17) |
| 6 hour | 52 | −8.33 | (−10.03, −6.62) | 50 | −6.89 | (−8.63, −5.16) | 50 | −5.63 | (−7.37, −3.90) |
| 8 hour | 52 | −11.60 | (−13.30, −9.89) | 50 | −9.59 | (−11.33, −7.86) | 50 | −8.36 | (−10.09, −6.62) |
| 10 hour | 52 | −10.29 | (−11.99, −8.58) | 50 | −8.82 | (−10.56, −7.09) | 50 | −6.15 | (−7.89, −4.42) |
| 12 hour | 52 | −7.10 | (−8.80, −5.39) | 50 | −6.82 | (−8.56, −5.09) | 50 | −3.10 | (−4.83, −1.37) |
| 23.5 hour | 52 | −2.87 | (−4.57, −1.17) | 50 | −2.15 | (−3.88, −0.41) | 50 | −2.53 | (−4.26, −0.79) |

| Hour | Difference From Single Dose of Placebo to 400 mg Dose of Vibegron (msec) | | Difference From Single Dose of Placebo to 200 Dose of Vibegron (msec) | |
|---|---|---|---|---|
| | LS Mean Difference | 90% CI [a] | LS Mean Difference | 90% CI [a] |
| 0.5 hour | 3.37 | (1.49, 5.25) | 2.90 | (1.00, 4.80) |
| 1 hour | 4.60 | (2.71, 6.48) | 4.98 | (3.07, 6.88) |
| 2 hour | 0.81 | (−1.07, 2.69) | 2.14 | (0.23, 4.04) |
| 3 hour | −1.04 | (−2.92, 0.85) | 0.40 | (−1.50, 2.30) |
| 4 hour | −2.96 | (−4.84, −1.08) | −0.83 | (−2.73, 1.07) |
| 6 hour | −2.70 | (−4.58, −0.81) | −1.26 | (−3.16, 0.64) |
| 8 hour | −3.24 | (−5.12, −1.36) | −1.24 | (−3.14, 0.66) |
| 10 hour | −4.14 | (−6.02, −2.25) | −2.67 | (−4.57, −0.77) |
| 12 hour | −4.00 | (−5.88, −2.11) | −3.72 | (−5.63, −1.82) |
| 23.5 hour | −0.34 | (−2.22, 1.54) | 0.38 | (−1.52, 2.28) |

Abbreviations: LS mean, least square means, CI, confidence interval
400 mg vibegron: Single dose of 400 mg vibegron (8 × 50 mg tablets).
200 mg vibegron: Single dose of 200 mg vibegron (4 × 50 mg tablets vibegron + 4 × vibegron matching placebo tablets)
Placebo: Single Dose of vibegron matching placebo (8 × vibegron matching placebo tablets).
QTcF results at baseline (arithmetic mean): Placebo = 407.38, 400 mg vibegron = 407.64, 200 mg vibegron = 406.75, Moxifloxacin = 407.77
[a] The two-sided 90% confidence intervals are equivalent to one-sided upper 95% confidence intervals.

Example 4

Clinical Efficacy Data

A randomized, double-blind, placebo- and active-controlled, parallel-group two-part Phase 2b study of vibegron in men and women with OAB (stratified as OAB wet and OAB dry) was completed. Part 1 was a dose-ranging study to assess the safety, tolerability, and efficacy of vibegron and tion, subjects in the OAB wet strata must have had an average number of urgency incontinence episodes≥1 per diary day. Subjects in the OAB dry strata must have had an average number of urgency episodes≥3 per diary day and an average of <1 urgency incontinence episodes per diary day. The total number of urgency incontinence episodes must have exceeded the total number of stress incontinence episodes for all subjects.

The primary objectives of this study were to assess the safety and tolerability of treatment with selected vibegron doses (alone or in combination with tolterodine) and to investigate dose-related reductions in average number of daily micturitions compared with placebo at Week 8.

In Part 1, statistically significant decreases in the average number of daily micturitions were observed in the vibegron 100 mg and 50 mg treatment groups as compared to the placebo group at Week 8. Statistically significant decreases from baseline as compared to placebo were also observed in the vibegron 100 mg and 50 mg treatment groups for secondary endpoints which included urgency incontinence and total incontinence (in subjects with OAB wet), and urgency episodes in all subjects. Statistically significant increases from baseline as compared to placebo were also observed for the secondary endpoint volume voided per micturition in the vibegron 15, 50 and 100 mg treatment groups. (Tables 13 and 14).

TABLE 13

Analysis of Change from Baseline In The Volume Voided (ML) Per Micturition at Week 8

| Treatment | N | Difference in LS Means | p-value |
|---|---|---|---|
| Vibegron 3 mg | 144 | 15.99 | 0.032 |
| Vibegron 15 mg | 131 | 28.23 | <0.001 |
| Vibegron 50 mg | 146 | 29.05 | <0.001 |
| Vibegron 100 mg | 148 | 23.36 | 0.002 |
| Tolterodine ER 4 mg | 133 | 30.77 | <0.001 |

Difference from Placebo Week 8

A double-blind, randomized, placebo controlled, multi-center, Phase 3 study designed to evaluate the safety and efficacy of vibegron in males and females with OAB was completed. Upon completion of the placebo Run-in period, 1,232 patients were randomized to receive blinded study treatment for 12 weeks including: vibegron 50 mg (N=370), vibegron 100 mg (N=369), placebo (N=369), or imidafenacin 0.2 mg (comparator; N=117). The results demonstrate that once daily vibegron produced statistically significant reductions in efficacy parameters including: micturitions, UUI episodes, total incontinence episodes, and urgency episodes (Table 15).

TABLE 15

Analysis of Change from Baseline in Average Daily Number Events at Week 12 - Constrained Longitudinal Data Analysis (cLDA) Model[a]

| Event | 50 mg Dose | 100 mg Dose |
|---|---|---|
| Micturitions | −0.86 (−1.12, −0.60) p < 0.0001 | −0.81 (−1.07, −0.55) p < 0.0001 |
| Urge Urinary Incontinence Episodes | −0.27 (−0.44, −0.10) p = 0.0015 | −0.39 (−0.55, −0.22) p < 0.0001 |
| Total Incontinence Episodes | −0.30 (−0.49, −0.12) p = 0.0015 | −0.43 (−0.61, −0.24) p < 0.0001 |
| Urgency Episodes | −0.51 (−0.76, −0.25) p = 0.0001 | −0.67 (−0.93, −0.42) p < 0.0001 |
| Volume Voided (mL) | 25.76 (20.02, 31.46) p < 0.0001 | 22.16 (16.44, 27.89) p < 0.0001 |

[a]Results presented as least squares mean placebo adjusted change from baseline (95% confidence interval [CI]), p-value.

TABLE 14

Analysis of Change from Baseline in Average Daily Number Events at Week 8 - Constrained Longitudinal Data Analysis (cLDA) Model[a] (Full-Analysis-Set Population - Part 1 Base Study)

| Event | Treatment | N | Baseline Mean | Baseline SD | Week 8 Mean | Week 8 SD | Change from Baseline Week 8 Mean | Change from Baseline Week 8 SD | Difference in LS Means[b] | p-value |
|---|---|---|---|---|---|---|---|---|---|---|
| Micturitions | Placebo | 141 | 10.86 | 2.84 | 9.77 | 2.51 | −1.09 | 2.17 | n/a | n/a |
| | Vibegron 3 mg | 144 | 10.93 | 2.35 | 9.35 | 2.43 | −1.56 | 1.97 | −0.46 | 0.056 |
| | Vibegron 15 mg | 132 | 11.32 | 3.48 | 9.53 | 2.85 | −1.71 | 2.22 | −0.45 | 0.064 |
| | Vibegron 50 mg | 148 | 11.21 | 3.16 | 9.05 | 2.28 | −1.87 | 1.78 | −0.64 | 0.007 |
| | Vibegron 100 mg | 148 | 11.15 | 2.32 | 9.02 | 2.59 | −2.11 | 1.81 | −0.91 | <0.001 |
| | Tolterodine ER 4 mg | 134 | 11.00 | 2.17 | 9.24 | 2.11 | −1.73 | 2.02 | −0.54 | 0.026 |
| Urgency Incontinence Episodes[c] | Placebo | 118 | 3.11 | 2.68 | 1.71 | 2.50 | −1.34 | 1.77 | n/a | n/a |
| | Vibegron 3 mg | 113 | 2.70 | 1.94 | 1.21 | 1.68 | −1.38 | 1.38 | −0.28 | 0.167 |
| | Vibegron 15 mg | 111 | 2.94 | 2.23 | 1.12 | 2.06 | −1.81 | 1.60 | −0.57 | 0.005 |
| | Vibegron 50 mg | 121 | 2.81 | 2.06 | 0.86 | 1.16 | −1.90 | 1.75 | −0.72 | <0.001 |
| | Vibegron 100 mg | 122 | 2.96 | 2.42 | 0.84 | 1.74 | −2.05 | 1.99 | −0.71 | <0.001 |
| | Tolterodine ER 4 mg | 100 | 2.80 | 2.13 | 1.15 | 2.18 | −1.67 | 1.55 | −0.46 | 0.030 |
| Total Incontinence Episodes[c] | Placebo | 118 | 3.61 | 3.26 | 1.88 | 2.68 | −1.68 | 2.01 | n/a | n/a |
| | Vibegron 3 mg | 113 | 3.05 | 2.11 | 1.38 | 1.75 | −1.56 | 1.55 | −0.18 | 0.401 |
| | Vibegron 15 mg | 111 | 3.32 | 2.44 | 1.31 | 2.26 | −1.99 | 1.64 | −0.48 | 0.029 |
| | Vibegron 50 mg | 121 | 3.10 | 2.26 | 1.02 | 1.40 | −2.02 | 1.82 | −0.60 | 0.005 |
| | Vibegron 100 mg | 122 | 3.43 | 2.83 | 1.12 | 2.08 | −2.26 | 2.41 | −0.58 | 0.007 |
| | Tolterodine ER 4 mg | 100 | 3.08 | 2.39 | 1.32 | 2.38 | −1.80 | 1.47 | −0.34 | 0.140 |
| Urgency Episodes | Placebo | 141 | 6.52 | 4.37 | 4.99 | 3.77 | −1.57 | 3.28 | n/a | n/a |
| | Vibegron 3 mg | 144 | 6.49 | 3.66 | 4.68 | 4.16 | −1.69 | 2.65 | −0.18 | 0.598 |
| | Vibegron 15 mg | 132 | 6.93 | 4.69 | 4.42 | 4.40 | −2.35 | 2.50 | −0.67 | 0.052 |
| | Vibegron 50 mg | 148 | 6.43 | 4.22 | 3.71 | 3.76 | −2.36 | 2.35 | −0.76 | 0.024 |
| | Vibegron 100 mg | 148 | 7.34 | 4.14 | 4.22 | 4.36 | −2.98 | 2.84 | −1.24 | <0.001 |
| | Tolterodine ER 4 mg | 134 | 6.39 | 3.78 | 3.91 | 3.65 | −2.52 | 2.73 | −0.94 | 0.007 |

[a]Constrained longitudinal data analysis model includes terms for time, region and interaction of time by treatment.
[b]Negative mean treatment differences are in favor of former treatments in comparison.
[c]Only in OAB Wet subjects.

Example 5

Safety Data

5.1 Phase I Safety Data

Safety data from 16 Phase 1 studies, which include 15 completed Phase 1 studies and 1 study that was terminated early (this study was terminated for reasons unrelated to efficacy or safety) was collected. In the Phase 1 program, a total of 466 subjects received at least one dose of vibegron; 238 subjects received single doses ranging from 2 to 600 mg and 238 subjects received multiple doses ranging from 25 to 400 mg for up to 28 days. Across the Phase 1 program, vibegron has been generally well tolerated. There were no treatment-emergent serious adverse events (SAEs) or deaths reported, and the majority of adverse events (AEs) were transient and mild or moderate in intensity.

In Phase 1 studies, there were isolated occurrences of orthostatic hypotension (decrease in systolic blood pressure>20 mmHg and/or decrease in diastolic blood pressure>10 mmHg), with or without symptoms (e.g., lightheadedness, dizziness, presyncope). The incidence of orthostatic AEs following co-administration of vibegron 100 mg or 150 mg and tolterodine ER 4 mg was similar to the incidence of these AEs following administration of vibegron or tolterodine alone. At doses up to 100 mg in Phase 1 multiple dose studies, AEs such as postural dizziness, dizziness, presyncope, or syncope have not exhibited a clear dose-response relationship. However, postural dizziness appeared to increase at doses of 100 mg and above and the incidence of the AE "orthostatic hypotension with symptoms" has tended to be higher at vibegron doses>200 mg. There were no occurrences of orthostatic AEs when vibegron 100 mg was coadministered to subjects with essential hypertension who were on a stable regimen of either metoprolol (a representative beta-blocker), or amlodipine (a representative vasodilator).

Review of preliminary Phase 1 safety data suggest no clinically meaningful changes in laboratory safety parameters (chemistry, hematology and urinalyses) or ECG parameters, including PR, QRS and QTc intervals. A thorough QT study has been completed, which found no clinically meaningful effect on QTc or blood pressure

5.2 Phase II Safety Data

Phase 2 safety data from a single Phase 2B study that has completed in which 933 subjects received at least one dose of vibegron was collected. Subjects received vibegron doses ranging from 3 to 100 mg for up to 8 weeks during the main study (alone or in combination with tolterodine). Of those completing the parent study, 605 subjects received doses of vibegron 50 mg (alone) or vibegron 100 mg (alone or in combination with tolterodine 4 mg) for up to 52 weeks during an extension study. A placebo group was included in the main study, and a group that received tolterodine monotherapy was included in the main study and in the extension. There were no deaths reported during the study. Vibegron was generally well tolerated. No meaningful differences in the overall incidence or severity of AEs or drug-related AEs were observed among the treatment groups compared to placebo.

Adverse events were reported in 607 (43.6%) of the 1393 allocated subjects in the main study. The proportion of subjects with one or more AEs in the vibegron 50 mg and vibegron 100 mg treatment groups was similar to placebo (see Table 14). A higher proportion of subjects reported one or more AEs in the vibegron 15 mg and vibegron 50 mg+tolterodine 4 mg treatment groups compared to placebo. The most frequently reported AEs were dry mouth, headache, urinary tract infections (UTI), and nasopharyngitis. The incidence of dry mouth was higher in groups that received tolterodine (alone or with vibegron) compared to the placebo or vibegron monotherapy groups.

There were 221 subjects with drug-related AEs, with the lowest incidence of drug-related AEs reported in the vibegron 100 mg treatment group. The proportion of subjects with drug-related AEs was similar in the vibegron monotherapy groups compared to placebo and only slightly higher in the concomitant treatment groups compared to placebo or either monotherapy. The proportion of subjects who discontinued due to a drug-related AE was low and similar across all treatment groups.

There were a total of 9 SAEs reported in 8 subjects and occurred across the treatment groups (2 placebo; 1 vibegron 3 mg; 1 vibegron 50 mg; 3 tolterodine 4 mg; 1 vibegron 50 mg+tolterodine 4 mg). The reported SAEs were atrial fibrillation, anaphylactic reaction, lung adenocarcinoma stage IV, chronic obstructive pulmonary disease, hypertension, overdose, foot fracture, and in one subject both gastroesophageal reflux disease and dizziness occurred after a pan endoscopic procedure that prolonged hospitalization. No specific AE term was reported in more than 1 subject. All SAEs were considered unrelated to study drug by the investigator.

During the 52-week extension, no meaningful differences in overall incidences of adverse events or serious adverse events were observed among the treatment groups.

Adverse events were reported in 531 (62.8%) of the 845 subjects. The proportion of subjects with one or more AEs was similar across all treatment groups. The most frequently reported adverse events were UTI, nasopharyngitis, upper respiratory tract infection, and dry mouth. The incidence of dry mouth was higher in the tolterodine ER 4 mg treatment group compared to the other treatment groups. The incidence of constipation was higher in the concomitant treatment group compared to the monotherapy treatment groups.

The proportion of subjects with drug-related AEs was slightly higher for tolterodine ER 4 mg and the concomitant dose arm compared to the vibegron 50 mg and 100 mg treatment arms. The proportion of subjects who discontinued due to an AE or a drug-related AE was higher for tolterodine ER 4 mg compared to the other treatment groups. There were total of 46 SAEs reported in 41 subjects during the extension. An overall higher incidence rate was reported in the tolterodine ER 4 mg and vibegron 50 mg treatment groups compared to the vibegron 100 mg treatment group. There was one drug-related SAE of ileus paralytic reported in the tolterodine ER 4 mg treatment group; the subject was discontinued due to this AE.

Table 16 below summarizes adverse events commonly seen in the vibegron Phase 2 program in patients with overactive bladder.

TABLE 16

Adverse Events in ≥2% Subjects in Phase 2 Study (First 12 weeks of Treatment)

| | Placebo<br>N = 205<br>n (%) | Vibegron<br>3 mg<br>N = 144<br>n (%) | Vibegron<br>15 mg<br>N = 134<br>n (%) | Vibegron<br>50 mg<br>N = 148<br>n (%) | Vibegron<br>100 mg<br>N = 261<br>n (%) | Tolterodine<br>ER<br>4 mg<br>N = 257<br>n (%) | Vibegron<br>100 mg +<br>tolterodine<br>ER 4 mg<br>N = 110<br>n (%) | Vibegron<br>50 mg +<br>Tolterodine ER<br>4 mg/Vibegron<br>50 mg<br>N = 134<br>n (%) | Total<br>N = 1,393<br>n(%) |
|---|---|---|---|---|---|---|---|---|---|
| ≥1 AE | 88 (42.9) | 55 (38.2) | 70 (52.2) | 62 (41.9) | 107 (41.0) | 116 (45.1) | 40 (36.4) | 69 (51.5) | |
| Serious AE | 2 (1.0) | 1 (0.7) | 0 | 1 (0.7) | 0 | 3 (1.2) | 0 | 8 (0.7) | |
| Drug-related AE | 30 (14.6) | 21 (14.6) | 23 (17.2) | 23 (15.5) | 31 (11.9) | 42 (16.3) | 21 (19.1) | 30 (14.6) | |
| Discontinuation due to AE | 5 (2.4) | 3 (2.1) | 4 (3.0) | 2 (1.4) | 6 (2.3) | 4 (1.6) | 2 (1.8) | 3 (2.2) | |
| Discontinuation due to drug-related AE | 3 (1.5) | 2 (1.4) | 4 (3.0) | 0 | 3 (1.1) | 0 | 1 (0.9) | 2 (1.5) | |
| SOC/Preferred Term | | | | | | | | | |
| Eye disorders | | | | | | | | | |
| Dry eye | 10 (4.9) | 2 (1.4) | 4 (3.0) | 2 (1.4) | 4 (1.5) | 10 (3.9) | 3 (2.7) | 2 (1.5) | 18 (1.3) |
| Gastrointestinal disorders | | | | | | | | | |
| Constipation | 5 (2.4) | 5 (3.5) | 6 (4.5) | 6 (4.1) | 2 (0.8) | 5 (1.9) | 4 (3.6) | 6 (4.5) | 39 (2.8) |
| Diarrhea | 5 (2.4) | 4 (2.8) | 2 (1.5) | 1 (0.7) | 5 (1.9) | 9 (3.5) | 1 (0.9) | 6 (4.5) | 33 (2.4) |
| Dry mouth | 6 (2.9) | 5 (3.5) | 6 (4.5) | 7 (4.7) | 4 (1.5) | 22 (8.6) | 13 (11.8) | 11 (8.2) | 74 (5.3) |
| Nausea | 3 (1.5) | 2 (1.4) | 2 (1.5) | 3 (2.0) | 3 (1.1) | 6 (2.3) | 0 (0.0) | 2 (1.5) | 21 (1.5) |
| General disorders and administration site conditions | | | | | | | | | |
| Fatigue | 1 (0.5) | 4 (2.8) | 6 (4.5) | 5 (3.4) | 2 (0.8) | 6 (2.3) | 2 (1.8) | 2 (1.5) | 28 (2.0) |
| Infections and infestations | | | | | | | | | |
| Nasopharyngitis | 14 (6.8) | 3 (2.1) | 7 (5.2) | 8 (5.4) | 10 (3.8) | 4 (1.6) | 2 (1.8) | 3 (2.2) | 51 (3.7) |
| Sinusitis | 2 (1.0) | 0 0 | 2 (1.5) | 1 (0.7) | 0 0 | 1 (0.4) | 0 (0.0) | 4 (3.0) | 10 (0.7) |
| Urinary tract infection | 7 (3.4) | 5 (3.5) | 5 (3.7) | 8 (5.4) | 8 (3.1) | 12 (4.7) | 5 (4.5) | 7 (5.2) | 57 (4.1) |
| Injury, poisoning and procedural complications | | | | | | | | | |
| Accidental overdose | 2 (1.0) | 3 (2.1) | 6 (4.5) | 4 (2.7) | 11 (4.2) | 6 (2.3) | 1 (0.9) | 2 (1.5) | 35 (2.5) |
| Investigations | | | | | | | | | |
| Alanine aminotransferase increased | 0 (0.0) | 0 (0.0) | 0 (0.0) | 0 (0.0) | 0 (0.0) | 1 (0.4) | 0 (0.0) | 3 (2.2) | 4 (0.3) |
| Aspartate aminotransferase increased | 0 (0.0) | 0 (0.0) | 1 (0.7) | 0 (0.0) | 0 (0.0) | 0 (0.0) | 0 (0.0) | 3 (2.2) | 4 (0.3) |
| Musculoskeletal and connective tissue disorders | | | | | | | | | |
| Arthralgia | 2 (1.0) | 0 0 | 2 (1.5) | 3 (2.0) | 0 (0.0) | 3 (1.2) | 1 (0.9) | 0 (0.0) | 11 (0.8) |
| Osteoarthritis | 1 (0.5) | 2 (1.4) | 1 (0.7) | 4 (2.7) | 1 (0.4) | 0 (0.0) | 0 (0.0) | 0 (0.0) | 9 (0.6) |
| Pain in extremity | 0 0 | 2 (1.4) | 0 0 | 2 (1.4) | 1 (0.4) | 1 (0.4) | 3 (2.7) | 2 (1.5) | 11 (0.8) |
| Nervous system disorders | | | | | | | | | |
| Dizziness | 5 (2.4) | 1 (0.7) | 6 (4.5) | 3 (2.0) | 7 (2.7) | 5 (1.9) | 3 (2.7) | 1 (0.7) | 31 (2.0) |
| Headache | 9 (4.4) | 3 (2.1) | 6 (4.5) | 6 (4.1) | 12 (4.6) | 9 (3.5) | 7 (6.4) | 6 (4.5) | 58 (4.0) |
| Renal and urinary disorders | | | | | | | | | |
| Dysuria | 1 (0.5) | 0 (0.0) | 0 (0.0) | 1 (0.7) | 0 (0.0) | 3 (1.2) | 3 (2.7) | 0 (0.0) | 8 (0.6) |

Serious adverse events observed during the first 12 weeks of treatment with vibegron monotherapy included lung adenocarcinoma stage IV (n=1) and chronic obstructive pulmonary disease (n=1); an SAE of overdose was reported in the vibegron-tolterodine combination arm. During the Phase 2 extension study, SAEs reported by 2 or more subjects receiving monotherapy included cerebrovascular accident (n=2) and osteoarthritis (n=2). The only SAE reported in the vibegron-tolterodine combination arm was borrelia infection. SAEs potentially related to a change in heart rate or blood pressure (at any time during treatment) included: loss of consciousness after 8 weeks of vibegron that did not recur on rechallenge (n=1), and in the tolterodine monotherapy arm atrial fibrillation (n=1) and dizziness (n=1). The frequency of injuries was numerically higher in the tolterodine arm than with vibegron (2.1%, n=5, vs. 0.9%, n=4). Given the low incidence and lack of a pattern for SAEs, no serious event is considered expected for vibegron.

Potential risks that may be associated with vibegron treatment, based on nonclinical data and data available for similar compounds, include orthostatic hypotension and increased exposure (~2-fold) in patients taking concomitant strong P-gp inducers.

5.3 Cardiovascular Safety

The cardiovascular safety of vibegron has been evaluated in patients with OAB and healthy volunteers. In a randomized, placebo- and active comparator (tolterodine)-controlled, 2-part efficacy and safety study with 52-week extension, seven orthostatic related AEs (which included the adverse event terms of postural dizziness, presyncope, and orthostatic hypotension) occurred in 6 (0.4%) subjects. The events occurred in one subject each in the placebo group (0.5%), the vibegron 15 mg group (0.3%), and the vibegron 50 mg+tolterodine ER/vibegron 50 mg treatment group (0.8%), and in 3 subjects in the vibegron 100 mg group (1.1%). The events occurred at random times throughout the study and were judged by the investigator to be mild in severity. None led to discontinuation. The overall incidence of orthostatic symptoms was low.

Changes from baseline in BP and HR across treatment groups are shown in Table 17. For systolic blood pressure (SBP) and diastolic blood pressure (DBP), the mean changes at Week 1 and mean maximum changes over 8 weeks for 50 mg and 100 mg were comparable between placebo and vibegron, with differences of <1 mm Hg. Categorical changes in SBP and DBP also were similar between placebo and vibegron, with a slight increase at 100 mg in percent of vibegron subjects with a change from baseline in DBP>15 mmHg (1.3% 100 mg vs 0.5% placebo). No dose-dependent pattern was detectable for HR, as the mean maximum changes over 8 weeks were comparable to placebo (<2 bpm). Small differences in the percent of subjects exceeding categorical heart rate and blood pressure thresholds for vibegron were similar to those in the tolterodine arm.

TABLE 18

Maximum MA4 HR and Difference between Vibegron and Placebo at Day 14

| Panel | Dose (mg) | $N^a$ | $_{Maximum}$ MA4 HR$^b$ | | Difference from Placebo$^c$ | |
|---|---|---|---|---|---|---|
| All | Placebo | 14 | 3.07 | (0.26, 5.88) | | |
| A | 25 | 5 | 1.47 | (−3.24, 6.17) | −1.60 | (−7.09, 3.88) |
| B | 50 | 6 | 1.50 | (−2.79, 5.79) | −1.57 | (−6.70, 3.56) |
| C | 100 | 6 | 3.28 | (−1.02, 7.57) | 0.21 | (−4.93, 5.34) |
| D | 150 | 6 | 3.17 | (−1.13, 7.46) | 0.10 | (−5.04, 5.23) |
| G | 200 | 5 | 5.67 | (0.96, 10.37) | 2.60 | (−2.89, 8.08) |
| H | 300 | 6 | 9.06 | (4.76, 13.35) | 5.98 | (0.85, 11.12) |
| I | 400 | 6 | 10.33 | (6.04, 14.63) | 7.26 | (2.13, 12.39) |

$^a$One subject each in panels A and G discontinued and had no available data at day 14
$^b$Least-square mean and corresponding 90% confidence interval
$^c$Difference of least squares (active - placebo) and corresponding 90% confidence interval calculated from the linear fixed effects model

TABLE 17

Vital Sign Changes from Baseline for Vibegron and Tolterodine by Dose

HR Change from Baseline

| Treatment | n | Mean (95% CI) (week 1) | n | Mean (95% CI) Maximum | ⩾5 mm Hg n/N (%) | ⩾10 bpm n/N (%) | ≥15 bpm n/N (%) |
|---|---|---|---|---|---|---|---|
| Placebo | 186 | 0.12 (−1.04, 1.28) | 200 | 5.08 (4.02, 6.13) | 17/188 (9.0) | 1/188 (0.5) | 0 |
| 3 mg | 141 | 0.36 (−0.90, 1.62) | 143 | 5.57 (4.25, 6.90) | 16/140 (11.4) | 5/140 (3.6) | 1/140 (0.7) |
| 15 mg | 126 | 0.35 (−1.15, 1.85) | 134 | 6.56 (5.20, 7.92) | 17/132 (12.9) | 4/132 (3.0) | 1/132 (0.8) |
| 50 mg | 140 | 0.29 (−0.88, 1.46) | 146 | 5.49 (4.28, 6.69) | 12/144 (8.3) | 4/144 (2.8) | 1/144 (0.7) |
| 100 mg | 237 | 0.35 (−0.69, 1.38) | 257 | 6.12 (5.10, 7.15) | 28/237 (11.8) | 7/237 (3.0) | 1/237 (0.4) |
| Tolterodine 4 mg | 246 | 0.68 (−0.31, 1.67) | 257 | 5.66 (4.69, 6.63) | 29/242 (12.0) | 11/242 (4.5) | 4/242 (1.7) |

SBP Change from Baseline

| Treatment | n | Mean (95% CI) (week 1) | n | Mean (95% CI) Maximum | ⩾5 mm Hg n/N (%) | ⩾10 mm Hg n/N (%) | ≥15 mm Hg n/N (%) |
|---|---|---|---|---|---|---|---|
| Placebo | 186 | −0.21 (−1.85, 1.43) | 200 | 7.84 (6.27, 9.40) | 24/188 (12.8) | 10/188 (5.3) | 3/188 (1.6) |
| 3 mg | 141 | −0.35 (−2.34, 1.65) | 143 | 7.14 (5.18, 9.10) | 21/140 (15.0) | 10/140 (7.1) | 4/140 (2.9) |
| 15 mg | 126 | −0.34 (−2.46, 1.78) | 134 | 8.93 (7.18, 10.67) | 22/132 (16.7) | 9/132 (6.8) | 1/132 (0.8) |
| 50 mg | 140 | −0.79 (−2.65, 1.08) | 146 | 7.01 (5.31, 8.70) | 24/144 (16.7) | 14/144 (9.7) | 3/144 (2.1) |
| 100 mg | 237 | −0.77 (−2.22, 0.68) | 257 | 6.51 (5.09, 7.93) | 28/237 (11.8) | 10/237 (4.2) | 3/237 (1.3) |
| Tolterodine 4 mg | 246 | 0.04 (−1.36, 1.43) | 257 | 7.29 (6.01, 8.57) | 41/242 (16.9) | 19/242 (7.9) | 7/242 (2.9) |

DBP Change from Baseline

| Treatment | n | Mean (95% CI) (week 1) | n | Mean (95% CI) Max | ⩾5 mm Hg n/N (%) | ⩾10 mm Hg n/N (%) | ≥15 mm n/N Hg (%) |
|---|---|---|---|---|---|---|---|
| Placebo | 186 | 0.11 (−0.94, 1.17) | 200 | 4.89 (3.89, 5.89) | 18/188 (9.6) | 6/188 (3.2) | 1/188 (0.5) |
| 3 mg | 141 | −0.37 (−1.69, 0.95) | 143 | 5.03 (3.92, 6.15) | 14/140 (10.0) | 3/140 (2.1) | 1/140 (0.7) |
| 15 mg | 126 | 0.03 (−1.52, 1.59) | 134 | 6.37 (5.20, 7.53) | 15/132 (11.4) | 3/132 (2.3) | 1/132 (0.8) |
| 50 mg | 140 | −0.70 (−2.07, 0.67) | 146 | 4.19 (3.10, 5.29) | 11/144 (7.6) | 5/144 (3.5) | 1/144 (0.7) |
| 100 mg | 237 | −0.69 (−1.72, 0.34) | 257 | 4.80 (3.88, 5.72) | 31/237 (13.1) | 8/237 (3.4) | 3/237 (1.3) |
| Tolterodine 4 mg | 246 | −0.12 (−1.10, 0.86) | 257 | 5.19 (4.26, 6.13) | 30/242 (12.4) | 13/242 (5.4) | 3/242 (1.2) |

Mean maximum is from week 1 to 8.
Counts based on 3 Consecutive Post-Baseline Visits.

More intensive assessments of heart rate and blood pressure were performed in healthy volunteers in several Phase 1 studies. A 6-part, double-blinded, randomized, placebo-controlled study to assess the safety, tolerability and multiple-dose PK of vibegron in healthy subjects that included specific analyses for heart rate. Doses ranged from 25 to 400 mg once daily for 7 to 28 days depending on the cohort. Least squares mean and 90% confidence intervals of maximum change from baseline in moving average of heart rate over 4 hours postdose (MA4 HR) are presented in Table 18. Effects on heart rate were dose dependent and the 100 mg dose demonstrated a <1 bpm difference from placebo.

Cardiovascular safety was also assessed in healthy volunteers in the thorough QT study following single doses of 200 and 400 mg, which approximate vibegron steady-state exposures at 100 mg and 200 mg, respectively. Mean maximum effects on blood pressure and RR interval were reduced with the lower dose as shown in Table 19. Using a log-log regression analysis from multiple-dose vibegron exposures (from three Phase 1 studies), the calculated mean±standard deviation $C_{max}$ and AUC from a 75 mg dose were 120±74.7 ng/mL and 1140±476 ng·h/mL, respectively. These estimations represent a $C_{max}$ and AUC that are approximately 3.3-fold and 2-fold lower, respectively, than the 200 mg single dose and 9.2-fold and 6-fold lower, respectively, than the 400 mg single dose.

TABLE 19

Single-Dose Pharmacokinetic Parameters and Mean Placebo-Corrected Change from Baseline RR interval and Blood Pressure

| Dose (mg) | Mean ± SD $C_{max}$ (ng/mL) | Mean ± SD AUC (ng · h/mL) | Maximum Mean Placebo Corrected Change from Baseline RR interval (90% CI) (msec) | Maximum Mean Placebo Corrected Change from Baseline Systolic BP (90% CI) (mmHg) | Maximum Mean Placebo Corrected Change from Baseline Diastolic BP (90% CI) (mmHg) |
|---|---|---|---|---|---|
| Vibegron 400 | 1100 ± 436 | 6800 ± 2300 | −162.45 (−184.24, −140.65) | 3.97 (2.12, 5.81) | 3.99 (2.62, 5.36) |
| Vibegron 200 | 406 ± 180 | 2430 ± 974 | −84.36 (−106.37, −62.35) | 2.20 (0.34, 4.06) | 2.42 (1.04, 3.81) |

Example 6

Dose Selection 5.1 Dose Comparison Efficacy

The Phase 2 study discussed in Example 4 demonstrated a dose-dependent effect on micturitions as seen in Table 20. Conversely, a dose dependent effect on urge incontinence or total incontinence was not observed. These data reveal a relatively shallow dose-response relationship between 50 and 100 mg once daily. Since vibegron efficacy begins to plateau from 50 to 100 mg, 75 mg captures a majority of the efficacy achieved with 100 mg.

TABLE 20

Efficacy of Vibegron 50 mg and 100 mg in Phase 2 Study

| Parameter | 50 mg-Placebo | 100 mg-Placebo | 100 mg-50 mg |
|---|---|---|---|
| Micturitions[a] | −0.64 | −0.91 | −0.27 |
| Urgency incontinence[b] | −0.72 | −0.71 | 0.01 |
| Total incontinence[b] | −0.60 | −0.58 | 0.02 |
| Urgency Episodes[b] | −0.76 | −1.24 | −0.48 |
| Volume voided[c] (ml) | 29.1 | 23.4 | −5.69 |

Data reported as difference in LS means
[a] change from baseline in average number of micturitions at week 8
[b] change from baseline in average number of episodes at week 8
[c] change from baseline in average volume per void over one diary day at week 8

5.2 Mitigating Side Effects

Vibegron demonstrates greater than a dose proportional increase in exposures. Surprisingly, an increase in dose from 50 to 100 mg results in an approximate 4-fold increase in $C_{max}$, the PK parameter considered most closely associated with cardiovascular effects. In order to contextualize PK parameters of a 75 mg dose, dose-$C_{max}$ and dose-AUC models were created using data from Phase 1 studies. Based on simulations, it was found that a vibegron dose of 75 mg avoids approximately 29% of the exposures observed with a 100 mg dose, subsequently reducing the upper range of exposures that would be achieved with a 100 mg dose. This reduction in outlier $C_{max}$ values reduces the potential for clinically relevant cardiovascular effects.

In Phase 1 multiple dose studies, at doses up to 100 mg, adverse events such as postural dizziness, dizziness, presyncope, syncope did not exhibit a clear dose-response relationship. However, postural dizziness appeared to increase at doses≥100 mg and the incidence of the adverse event "orthostatic hypotension with symptoms" was higher at vibegron doses greater than 150 mg. The risk of these dose-related adverse events can be disproportionally reduced by decreasing the dose from 100 mg to 75 mg, as a 25% reduction in dose produces an approximate 40% reduction in $C_{max}$ (120 ng/mL with 75 mg vs. 206 ng/mL with 100 mg). Without wishing to be bound by theory, the greater than dose-proportional increase in bioavailability with increasing dose may be due to saturable P-glycoprotein (P-gp)-mediated efflux in the gut.

A lower exposure with the 75 mg dose compared to a 100 mg dose disproportionally reduces the risk of adverse events in special populations as well. Subjects with moderate renal impairment had a mean increase in AUC of 1.6-fold compared to subjects with normal renal function whereas subjects receiving a potent CYP3A/P-gp inhibitor had an approximate 2-fold higher exposure. Assuming a 2 fold increase in $C_{max}$ of a 75 mg dose, the probability of these special populations achieving a vibegron $C_{max}$ greater than those observed with 100 mg is 15% (see FIG. 1). Minimizing exposures of subjects who fall at the extremes is important for elderly and females who demonstrated approximately a 50-70% higher $C_{max}$ than healthy young males.

All patents, patent applications, and other publications cited herein are fully incorporated by reference herein in their entirety.

Example 7

A Phase 3 Double-Blind, Randomized, Placebo-Controlled, Multi-Center Study to Evaluate the Efficacy, Safety and Tolerability of Vibegron in Men with Overactive Bladder (OAB) Symptoms on Pharmacological Therapy for Benign Prostatic Hyperplasia (BPH)

Some beta-3 adrenergic receptors ($\beta_3$-ARs) agonists have shown efficacy (with improved safety relative to anticholinergics) in treating persistent OAB symptoms in men on BPH therapies. This subset of the broader OAB population setting has unique safety needs (e.g., possibility of urinary retention) that have not been fully evaluated in previous clinical programs of OAB treatments. This study is designed to evaluate the safety, tolerability, and efficacy of vibegron (75 mg once daily (QD) administered for 24 weeks) or placebo in men with symptoms of OAB while receiving pharmacological therapy for BPH.

The primary study objective is to assess the efficacy, safety, and tolerability of vibegron versus placebo in men with OAB symptoms on pharmacological therapy for BPH. The primary clinical efficacy assessment is to evaluate whether vibegron+BPH pharmacological therapy is more effective than placebo+BPH pharmacological therapy in reducing both a) the mean daily micturition episodes and b) mean daily urgency episodes, based on a 3-day diary. The safety assessment will evaluate whether vibegron+BPH pharmacological therapy is safe and tolerable in men with OAB symptoms and BPH.

This study is an international Phase 3, randomized, double-blind, placebo-controlled, 2-part, parallel-group, multicenter study to evaluate the safety, tolerability, and efficacy of vibegron 75 mg in men with symptoms of OAB on stable doses of pharmacological therapy for BPH. At Baseline, subjects who meet all eligibility criteria are randomized 1:1 to receive either vibegron 75 mg, or placebo in a double-blind fashion. Randomization will be stratified based on baseline average number of micturition episodes per day (≤12 or >12), alpha blocker use with or without 5-ARI (yes or no), and urinary incontinence (yes or no).

The study consists of two parts: Part 1 (approximately 80 subjects) and Part 2 (approximately 1008 subjects). Part 1 includes additional orthostatic blood pressure and heart rate measurements at Screening, Run-in, Baseline, Week 2, and Week 4 to assess for potential orthostatic changes (pre-dose through 6 hours post dose except pre-dose for Screening and Run-In), but is otherwise consistent with the schedule for Part 2. Part 2 will proceed following review of 4-week safety data from Part 1 (including results from the orthostatic blood pressure) by an independent Data and Safety Monitoring Board (DSMB). Part 2 will also include a urodynamics sub-study (approximately 60 subjects).

Both study parts will consist of a Screening Period (1 to 4 weeks), a single-blind Run-in Period (2 weeks) in which placebo is added to BPH pharmacological therapy, and a randomized double-blind Treatment Period (24 weeks). Subjects who complete the Week 24 Visit maybe offered the opportunity to enroll in a 28-week extension study, which will be conducted under a separate study protocol (See Example 8). Subjects who do not enroll into the extension study will have a Safety Follow-up assessment (via telephone call) approximately 21 days (+up to 4 days) after the subject's last dose of study treatment (i.e., at Week 27 for subjects who complete the Week 24 Visit, or approximately 3 weeks after withdrawal for subjects who discontinue the study early). Additionally, Unscheduled Visit(s) may be arranged as needed.

At the Visit 1 (Screening) visit, a subject will be eligible for inclusion in this study only if all of the following criteria apply, unless otherwise noted:

1. Capable of giving written informed consent, which includes compliance with the requirements and restrictions listed in the consent form.
2. Male subjects of 45 years of age and above.
3. Body weight≥50 kg (inclusive).
4. Subject should have been on and agree to continue to stay on a stable dose of BPH treatment with either a) alpha blocker monotherapy orb) alpha blocker+5 ARI. Subjects on alpha blockers should have started their therapy at least 3 months prior to screening and be on a stable dose at the start of screening. Subjects on a 5-ARI should have started therapy at least 6 months prior to screening and be on a stable dose at screening.
5. Has a history of overactive bladder symptoms (frequency of ≥8 micturition episodes per day and urgency episodes of ≥3 per day with or without incontinence) while taking pharmacological therapy for at least 2 months to treat LUTS due to BPH.
6. Subject has an IPSS total score of ≥8 at Screening and Visit 3 (Baseline).
7. Subject has a prostate-specific antigen (PSA) level<4 ng/mL or 4≤PSA level<10 ng/mL with prostate cancer that has been ruled out to the satisfaction of the investigator.
8. Subjects agrees to not participate in another interventional drug or device clinical trial during the study.
9. In the opinion of the Investigator, is able and willing to comply with the requirements of the protocol, including completing study questionnaires and the Bladder Diary.
10. Visit 2 (Run-in) and Visit 3 (Baseline) visits, subject must have both additional qualifications based on the 3-day bladder diary period: a) having an average of ≥8 but ≤20 micturition episodes per day over the 3-day diary period, and (b) having an average of ≥3 urgency episodes per day over the 3-day diary period.
11. Subject must have a post void residual (PVR) volume value of <100 mL.
12. Visit 2 (Run-in) and Visit 3 (Baseline) visits, having at least 2 average nocturia episodes per night based on 3-day Bladder Diary at baseline. Nocturia is defined as waking to pass urine during the main sleep period.

At the Visit 1 (Screening) visit, a subject will not be eligible for inclusion in this study if any of the following criteria apply, unless otherwise noted:

1. Subject has a history of 24-hour urine volume greater than 3,000 mL.
2. Subject is a night-shift worker or plans to become a night-shift worker during the study.
3. Has lower urinary tract pathology that could, in the opinion of the Investigator, be responsible for urgency, frequency, or incontinence; including, but not limited to, bladder stones, interstitial cystitis, prostate cancer, persistent urethral stricture, urogenital tuberculosis, and urothelial tumor, as judged by the Investigator.
4. Has a history of prostate surgery, including minimally invasive transurethral or transrectal procedures, procedural treatments for BPH within 6 months of Screening or has a planned prostate surgery, including minimally invasive prostate procedures, during the study period.
5. Has a previous or planned pelvic radiation, low anterior resections (LAR), or any abdominoperineal resections (APR) during the study period.
6. Subject had a prostatitis in the past 6 months.
7. Has a history of urinary retention requiring an intervention (e.g., catheterization) for any reason.
8. Subject is taking or using any medications to treat erectile dysfunction (ED) and is not using them on a regular schedule. (ED medications with a short half-life such as sildenafil and vardenafil are allowed if used 2 times or less per week in the past 3 months and during the study.)
9. Subject has any planned procedures to treat ED (e.g., implantation of a penile device) during the treatment period, or has any planned prostate procedure.
10. Subject is using any herbal medications to treat overactive bladder, lower urinary tract symptoms/BPH symptoms, or erectile dysfunction in the past 3 months.
11. Subject started using diuretics within 3 months prior to the screening. Subjects already taking any diuretics on stable doses for at least 3 months prior to screening are allowed to enroll to the study.
12. Has maximum urinary flow (Qmax)<5.0 mL/second with a minimum voided volume of 125 mL.
13. Has a history of or current nocturnal polyuria at Visit 2 (Run-In) or Visit 3 (Baseline) visits, based on a 3-Day Bladder Diary. Nocturnal polyuria is defined as more than one third of the total urine output per 24 hours occurring at night time.
14. Has undergone bladder training or electrostimulation within 28 days prior to screening or plans to initiate either during the study.
15. Has an active or recurrent (>3 episodes per year) urinary tract infection by clinical symptoms or laboratory criteria (≥5 white blood cells (WBC)/hpf with presence of red blood cell (RBC) and/or a positive urine culture, defined as ≥$10^5$ colony forming units (CFU)/mL in 1 specimen). Subjects diagnosed with a urinary tract infection (UTI) at the Screening Visit may be treated and re-screened once the infection has resolved.

16. Has received an intravesical or intraprostatic treatment with any botulinum toxin, resiniferatoxin, or capsaicin within 6 months prior to Screening.

17. Has an implanted sacral neurostimulation (SNS) or use of any posterior tibial nerve stimulation (PTNS) device.

18. Has uncontrolled hyperglycemia (defined as fasting blood glucose>150 mg/dL or 8.33 mmol/L or non-fasting blood glucose>200 mg/dL or 11.1 mmol/L) or, if in the opinion of the Investigator, is uncontrolled.

19. Has diagnosis of diabetes insipidus.

20. Has a diagnosis of sleep apnea.

21. Has a concurrent malignancy or history of any malignancy within 5 years prior to screening, except for adequately treated basal cell or squamous cell skin cancer or in situ cervical cancer.

22. Has known or suspected HIV or AIDS or unexplained alarm symptoms (e.g., anemia, gastrointestinal bleeding, unintentional weight loss, suspected malignancy).

23. Has history of clinically relevant liver disease or severe hepatic impairment (Child-Pugh Class C).

24. Has clinically significant electrocardiogram (ECG) abnormality that, in the opinion of the Investigator, exposes the patient to risk by participating in the study.

25. Has uncontrolled hypertension (systolic blood pressure of ≥180 mmHg and/or diastolic blood pressure of ≥100 mmHg) or has a resting heart rate (by pulse) >100 beats per minute.

26. Subjects who have systolic blood pressures≥160 mmHg but <180 mmHg are excluded, unless deemed by the Investigator as safe to proceed in this study and able to complete the study per protocol; these subjects must be on stable hypertension medication for at least 3 months prior to screening.

27. All subjects with signs and symptoms of uncontrolled hypertension, regardless of blood pressure measurement, are excluded from the study. These include, but are not limited to neurological symptoms or findings, hematuria, proteinuria, retinopathy, unstable angina, and acute heart failure.

28. Has a history of cerebral vascular accident, transient ischemic attack, unstable angina, myocardial infarction, coronary artery interventions (e.g., coronary artery bypass grafting or percutaneous coronary interventions [e.g., angioplasty, stent insertion]), or neurovascular interventions (e.g., carotid artery stenting) within 6 months prior to the Screening Visit. Subjects with these conditions should be on stable medical therapy for at least 3 months prior to the Screening Visit.

29. Has a history of injury, surgery, or neurodegenerative diseases (e.g., multiple sclerosis, Parkinson's) that could affect the lower urinary tract or its nerve supply.

30. Has hematuria that was not evaluated, including microscopic hematuria (>5 RBCs/hpf). Subjects with known, fully evaluated, benign hematuria may participate. Documentation must be obtained indicating an unremarkable upper urinary tract (kidneys and ureters) imaging study (e.g., computerized tomography (CT) scan with and without contrast, renal ultrasound, magnetic resonance imaging (MM), intravenous pyelogram, etc.) and cystoscopy. Subjects whose hematuria has not been previously evaluated may not be enrolled.

31. Has alanine aminotransferase or aspartate aminotransferase>2.0 times the upper limit of normal (ULN), or bilirubin (total bilirubin)>1.5×ULN (or >2.0×ULN if secondary to Gilbert syndrome or pattern consistent with Gilbert syndrome).

32. Has an estimated glomerular filtration rate (eGFR)<30 mL/min/1.73 m².

33. Use of any prohibited medications.

34. Had changed the dose of any medications within 4 weeks prior to the Screening Visit or plans to initiate or change the dosing of any of these medications during the study.

35. History of sensitivity to any of the study treatments, or components thereof or a history of drug or other allergy that, in the opinion of the Investigator, contraindicates their participation.

36. Is currently participating or has participated in a study with an investigational compound or device or procedure within 28 days prior to screening.

37. Is currently participating in or has participated in a study with vibegron.

38. Has a history of significant drug or alcohol abuse/dependence within a year prior to screening, as assessed by the investigator.

39. Has coronary or neurovascular interventions planned during the duration of the study.

40. Has a history or current evidence of any condition, therapy, laboratory abnormality, or other circumstances that might, in the opinion of the Investigator, confound the results of the study, interfere with the subject's ability to comply with the study procedure, or make participation in the study not in the subject's best interest.

41. At Visit 3 (Baseline), subject was non-compliant during the 2-week placebo-controlled run-in period (taking <80% or >120% of the study medication).

Primary and secondary study endpoints are as follows: (Note "per day" refers to a continuous 24-hour period.)

Co-Primary Efficacy Endpoints
    Change from baseline (CFB) at Week 12 in the average number of micturition episodes per day.
    CFB at Week 12 in the average number of urgency episodes (urgency: need to urinate immediately) per day.

Secondary Efficacy Endpoints
    CFB at Week 12 in the average number of nocturia episodes per night.
    CFB at Week 12 in the average number of urge urinary incontinence episodes per day for subjects with urinary incontinence at baseline.
    CFB at Week 12 in the average of International Prostate Symptom Score (IPSS) Storage score (1-week recall).
    CFB at Week 12 in the average volume voided per micturition.

Other Endpoints
    CFB at Week 2, Week 4, Week 8, Week 16, Week 20 and Week 24 in the average number of micturition episodes per day.
    CFB at Week 2, Week 4, Week 8, Week 16, Week 20, and Week 24 in the average number of urgency episodes per day.
    CFB at Week 2, Week 4, Week 8, Week 16, Week 20 and Week 24 in the average number of nocturia episodes per night.
    CFB at Week 4, Week 8, Week 16, Week 20, and Week 24 in the IPSS Storage score (1-week recall).
    CFB at Week 4, Week 8, Week 12, Week 16, Week 20, and Week 24 in the IPSS Quality of Life score (1-week recall).
    CFB at Week 2, Week 4, Week 8, Week 16, Week 20, and Week 24 in the average number of urge urinary incontinence episodes per day for subjects with urinary incontinence at baseline.
    CFB at Week 2, Week 4, Week 8, Week 16, Week 20, and Week 24 in the average volume voided per micturition.

CFB at Week 2, Week 4, Week 8, Week 12, Week 16, Week 20, and Week 24 in the average number of total incontinence episodes per day for subjects with urinary incontinence at baseline.

Percent of all subjects with a 50% reduction from baseline in urgency episodes (urgency: need to urinate immediately) per day at Week 2, Week 4, Week 8, Week 12, Week 16, Week 20, and Week 24.

Percent of subjects with urinary incontinence at baseline with a 75% reduction from baseline in urge urinary incontinence episodes per day at Week 2, Week 4, Week 8, Week 12, Week 16, Week 20, and Week 24.

Other/Exploratory Endpoints—Quality-of-Life

CFB at Week 12 in Symptom Bother Score as assessed by Overactive Bladder Questionnaire Long Form (OAB-q-LF), (1-week recall).

CFB at Week 12 in heath related quality of life (HRQL) total score as assessed by OAB-q-LF. (HRQL includes subscales: coping, concern, sleep and social interaction. The total score will be calculated by adding the 4 subscales scores.)

CFB at Week 12 and Week 24 in HRQL subscale Coping score as assessed by OAB-q-LF.

CFB at Week 12 and Week 24 in HRQL subscale Concern score as assessed by OAB-q-LF.

CFB at Week 12 and Week 24 in HRQL subscale Sleep score as assessed by OAB-q-LF.

CFB at Week 12 and Week 24 in HRQL subscale Social Interaction score as assessed by OAB-q-LF.

CFB at Week 12 and Week 24 in EQ-5D-5L as assessed by measure of health status questionnaire developed by the EuroQolGroup.

CFB at Week 4, Week 12, and Week 24 in overall bladder symptoms based on Patient Global Impression of Severity (PGI-Severity).

CFB at Week 4, Week 12, and Week 24 in overall control over bladder symptoms based on Patient Global Impression of Control (PGI-Control).

CFB at Week 4, Week 12, and Week 24 in overall symptom frequency based on Patient Global Impression of Symptom Frequency (PGI-Frequency).

CFB at Week 4, Week 12, and Week 24 in overall urgency-related leakage over bladder symptoms based on Patient Global Impression of Urgency-Related Leakage (PGI-Leakage) in subjects with urinary incontinence at baseline.

Overall change of bladder symptoms based on Patient Global Impression of Change (PGI-Change) at Week 4, Week 12, and Week 24.

CFB at Week 12 and Week 24 in the International Index of Erectile Function (IIEF).

Efficacy assessments will be collected in the form of 3-day Subject Bladder Diary. Information collected in the diaries will be used for assessment of the primary and secondary efficacy endpoints related to the number of micturition, urgency, nocturia, and incontinence episodes per day as well as one 24-hr the volume voided of urine. In addition, subjects will complete IPSS assessments, OAB-q LF, EQ-5D-5L, and PGI scores to assess quality of life endpoints.

Subjects will complete questionnaires at the site at the start of each required study visit (before vital signs and blood draws) to assess subject-perceived symptom relief and health-related quality of life.

Bladder Diaries

The Bladder Diary is used by subjects to record the frequency of daily OAB symptoms including all micturitions, urgency, incontinence, nocturia, one 24-hr volume voided of urine, and main reason for incontinence, and volume voided per micturition (over one 24-hour period) by selecting the respective box for each symptom occurring during the course of a given day and night.

The Bladder Diary should be completed by the subject on all 3 days within the 7 days prior to Visit 2 (Run-in), Visit 3 (Baseline) and Weeks 2, 4, 8, 12, 16, 20 and 24. Urine volume may be collected during any one (1) of the 7 Diary Days prior to the visit, and it should be recorded for ~24-hours starting from the time the patient gets up for the day and continues until the time the patient gets up for the day on the next day.

A "Diary Day" is defined as the time between when the subject gets up for the day each morning (i.e., the time the subject got up for the day yesterday to the time the subject got up for the day today; approximately a 24-hour period).

To be eligible for the study, subjects must have a minimum of:

3 consecutive Diary Days during the Screening Period (over the 7 days prior to the Run-in Visit), and 3 consecutive Diary Days during the Run-in Period (over the 7 days prior to the Baseline Visit), and be capable in the Investigator's opinion of maintaining compliance with the diary requirements, including the measurement and recording of urine volume, as required, at Baseline and throughout the course of the study.

At all study visits, the site staff should inquire whether the subject had any difficulties with the diary and address any questions subjects may have. Instructions for proper completion of the diary should be re-reviewed. Subjects will be trained to enter data immediately following each event (in real time) and to input data from any "missed" events as soon as they are able. They will review and confirm that data from all events occurring within the preceding Diary Day (approximately 24 hours) have been entered at a consistent time each morning (e.g., upon getting up for the day).

Responses to the Bladder Diary will be reviewed by the site staff to assess whether subjects are capable of completing the diary and if subjects meet eligibility criteria. The daily averages for micturitions, urgency episodes, nocturia episodes, and UUI episodes will be calculated as average of the total by the number of events on Diary Days. Subjects who do not meet the OAB entry criteria will be excluded from the study.

Patient-Reported Outcomes

Subjects will complete questionnaires at the site at the start of each required study visit (before vital signs and blood draws) to assess subject-perceived symptom relief, symptom bother, and health-related quality of life at the study visits. Recommended guidelines for the use of patient-reported outcome measures can be found in "Guidance for Industry, Patient-Reported Outcome Measures: Use in Medical Product Development to Support Labeling Claims," U.S. Department of Health and Human Services, Food and Drug Administration, December 209, which is incorporated by reference in its entirety. These include the following questionnaires:

The International Prostate Symptom Score (IPSS) includes 8 questions (7 concerning urinary symptoms and 1 concerning quality of life), each with answers based on a 6-point scale indicating increasing severity. The urinary symptom responses are assigned points from 0 to 5. The Total IPSS Score can therefore range from 0 to 35 (asymptomatic to very symptomatic). The quality of life responses are assigned points from 0 to 6.

Global Impression Items include Patient Global Impression of Severity (PGI Severity), Patient Global Impression of Control (PGI-Control), Patient Global Impression of Frequency (PGI-Frequency), Patient Global Impression of Leakage (PGI-Leakage), and Patient Global Impression of Change (PGI-Change).

Overactive Bladder Questionnaire (OAB-q long form [OAB-q LF], 1-week recall) is a 33-item patient-administered, disease-specific questionnaire that includes a Health-Related QoL (HRQL) scale (25 items) and a Symptom Bother Scale (8 items). The HRQL is a multidomain concept that represents the patient's general perception of the effect of illness and treatment on physical, psychological, and social aspects of life. Claiming a statistical and meaningful improvement in HRQL implies: (1) that all HRQL domains that are important to interpreting change in how the clinical trial's population feels or functions as a result of the targeted disease and its treatment were measured; (2) that a general improvement was demonstrated; and (3) that no decrement was demonstrated in any domain. In the present study, the HRQL scale is divided into 4 subscales: Coping, Concern/Worry, Sleep, and Social Interaction. The Coping subscale was a key secondary endpoint, with items scored from 1 (none of the time) to 6 (all the time), with higher scores indicating better QoL. The HRQL total score is calculated by summating the individual HRQL subscale scores. The Symptom Bother Scale items are scored from 1 (not at all) to 6 (a very great deal), with higher Symptom Bother scores indicating greater symptom severity. The instrument was developed and validated in both continent and incontinent OAB patients, including both men and women.

The EQ-5D health questionnaire is a standardized instrument for use as a measure of health outcome. See, Rabin et al. Value in Health; 17(1):70-76 (2014).

The Internal Index of Erectile Function (IIEF) is a 15-question assessment of erectile dysfunction, examining the 4 main domains of male sexual function: erectile function, orgasmic function, sexual desire, and intercourse satisfaction.

It is applicable to a wide range of health conditions and treatments; it provides a simple descriptive profile and a single index value for health status.

The safety endpoints include safety and tolerability parameters such as adverse events (AEs), clinical laboratory values, and vital sign assessments.

An AE is any untoward medical occurrence in a clinical study subject, temporally associated with the use of study drug, whether or not considered related to the study drug. An AE can therefore be any unfavorable and unintended sign (including an abnormal laboratory finding), symptom, or disease (new or exacerbated) temporally associated with the use of study drug.

Example 8

A Phase 3 Open-Label Extension Study to Evaluate the Long-Term Safety and Efficacy of Vibegron in Men with Overactive Bladder (OAB) Symptoms on Pharmacological Therapy for Benign Prostatic Hyperplasia (BPH)

An international, Phase 3, open-label 28-week study is being conducted as an extension of the study described in Example 7 ("parent study") to evaluate the safety and efficacy of vibegron 75 mg in men with symptoms of OAB on stable doses of pharmacological therapy for BPH. Approximately 300 men with symptoms of OAB on stable doses of pharmacological therapy for BPH who completed 24 weeks in the parent study and continue to qualify for this study may be permitted to enroll in this extension study, from approximately 60 study sites.

During this extension study, subjects who had been randomized in the parent study to receive vibegron 75 mg will continue their same treatment once daily for an additional 28 weeks, and subjects who had been randomized in the parent study to the placebo group will receive study treatment of vibegron 75 mg once daily for 28 weeks during the extension. Thus, through participation in both the parent and extension studies, subjects originally randomized to vibegron will receive 52 weeks total of vibegron treatment, and subjects originally randomized to placebo will receive 28 weeks total of vibegron treatment.

Subjects will continue on the same alpha-blockers (e.g., tamsulosin, doxazosin, and alfuzosin) with or without 5α-reductase inhibitors 5-ARIs) use (e.g., finasteride, dutasteride, and alfatradiol) in the extension study as administered in the parent study.

Primary and secondary study endpoints are shown below. Assessments are referenced to the initial Baseline from the parent study. Therefore, change from baseline (CFB) study endpoints for the extension study are relative to the parent study baseline. At the Week 52 visit, CFB comprises 52 weeks of vibegron exposure for subjects randomized to vibegron in the baseline study and 28 weeks of vibegron exposure for subjects randomized to placebo.

With respect to study endpoints, "per day" refers to a "Diary Day," which is defined as the time between when the subject gets up for the day each morning and the time the subject gets up for the day the next morning as recorded in the subject bladder diary (approximately a 24-hour period).

Primary Endpoints—Safety
  Including AEs, clinical laboratory, vital sign assessments, PVR volume, and Total IPSS
Secondary Endpoints—Efficacy
  CFB at Week 52 in the average number of micturition episodes per day
  CFB at Week 52 in the average number of urgency episodes (urgency: need to urinate immediately) per day
  CFB at Week 52 in the average number of nocturia episodes per night
  CFB at Week 52 in the average number of urge urinary incontinence episodes per day in subjects with incontinence at the parent study baseline
  CFB at Week 52 in the average of International Prostate Symptom Score (IPSS) Quality of Life score (1-week recall)
  CFB at Week 52 in the average volume voided per micturition
Other Endpoints
  CFB at Week 52 in the average number of total incontinence episodes per day in subjects with incontinence at parent study baseline
  Percent of all subjects with a 50% reduction from baseline in urgency episodes (urgency: need to urinate immediately) per day at Week 52
  Percent of subjects with urinary incontinence at parent study baseline with a 75% reduction from baseline in urge urinary incontinence episodes per day at Week 52
Other/Exploratory Endpoints—Quality-of-Life
  CFB at Week 52 in the IPSS subscale Voiding score (1-week recall)
  CFB at Week 52 in the IPSS subscale Quality of Life score (1-week recall)

CFB at Week 52 in Symptom Bother Score as assessed by Overactive Bladder Questionnaire Long Form (OAB-q-LF), (1-week recall)

CFB at Week 52 in heath related quality of life (HRQL) total score as assessed by OAB-q-LF. (HRQL includes subscales: coping, concern, sleep and social interaction. The total score will be calculated by adding the 4 subscales scores.)

CFB at Week 52 and Week 24 in HRQL subscale Coping score as assessed by OAB-q-LF CFB at Week 52 and Week 24 in HRQL subscale Concern score as assessed by OAB-q-LF CFB at Week 52 and Week 24 in HRQL subscale Sleep score as assessed by OAB-q-LF CFB at Week 52 and Week 24 in HRQL subscale Social Interaction score as assessed by OAB-q-LF CFB at Week 52 in EQ-5D-5L as assessed by measure of health status questionnaire developed by the EuroQol-Group CFB at Week 52 in overall bladder symptoms based on Patient Global Impression of Severity (PGI-Severity)

CFB at Week 52 in overall control over bladder symptoms based on Patient Global Impression of Control (PGI-Control)

CFB at Week 52 in overall symptom frequency based on Patient Global Impression of Symptom Frequency (PGI-Frequency)

CFB at Week 52 in overall urgency-related leakage over bladder symptoms based on Patient Global Impression of Urgency-Related Leakage (PGI-Leakage) in subjects with urinary incontinence at parent study baseline Overall change of bladder symptoms based on Patient Global Impression of Change (PGI-Change) at Week 52

Example 9

A Phase 3 Randomized, Double-Blind, Placebo- and Active (Tolterodine)-Controlled Clinical Study An international, Phase 3, randomized, double-blind, placebo-controlled with active control (tolterodine), parallel-group, multicenter study in men and women with overactive bladder, was conducted. Enrollment of patients included individuals with OAB Wet (those with UUI, the involuntary loss of urine accompanied by urgency) and OAB Dry (those without UUI). A total of 1,518 patients were randomized across 215 study sites into one of three groups for a 12-week treatment period.

The study consisted of a Screening Period (1 to 5 weeks), a single-blind Run-in Period (2 weeks), a randomized double-blind Treatment Period (12 weeks), and a Follow-up Period (4 weeks).

The study assessed the safety, tolerability, and efficacy of 75 mg vibegron versus placebo. Tolterodine ER 4 mg was the active control. Patients were randomized 5:5:4 in a double-blind fashion to one of three treatment arms: vibegron 75 mg, placebo, or tolterodine ER 4 mg, all administered once daily for 12 weeks during the Treatment Period. Between the Baseline and Week 12 Visits, patients had study assessments at Week 4 and Week 8.

8.1. Eligibility Criteria

To be eligible for participation in this study, a patient must have met all the following Inclusion Criteria, and none of the following Exclusion Criteria, before enrollment.

8.1.1 Inclusion Criteria

1. Willing and able to provide written informed consent.
2. Males or females≥18 years of age. Note: Up to 15% of patients can be male.
3. Has a history of OAB (as diagnosed by a physician) for at least 3 months prior to the Screening Visit. Note: OAB is defined as urgency, with or without urge urinary incontinence (UUI), usually associated with frequency and nocturia. Urodynamic evaluation is not required.
4. Meets either the OAB Wet or OAB Dry criteria described below, based on the Patient Voiding Diary returned both at the Run-in Visit and Baseline Visit (all Complete Diary Days must be used in determining eligibility). A minimum of 5 Complete Diary Days [not necessarily consecutive] are required for the diary returned at the Run-in Visit, and 4 Complete Diary Days are required for the diary returned at the Baseline Visit. Averages should not be rounded up to the whole number:
   a. OAB Wet criteria:
   i. An average of ≥8.0 micturitions per Diary Day; and
   ii. An average of ≥1.0 UUI episodes per Diary Day; and
   iii. If stress urinary incontinence is present, the total number of UUI episodes must be greater than the total number of stress urinary incontinence episodes from the previous visit diary.
   b. OAB Dry criteria:
   i. An average of ≥8.0 micturitions per Diary Day; and,
   ii. An average of ≥3.0 urgency episodes per Diary Day; and
   iii. An average of <1.0 UUI episodes per Diary Day; and
   iv. If stress urinary incontinence is present, the total number of UUI episodes must be greater than the total number of stress urinary incontinence episodes from the previous visit diary.
5. For females of reproductive potential: Agrees to remain abstinent or use (or have their male partner use) an acceptable method of birth control (as defined in Section 5.2.1) each time the patient has intercourse from the Screening Visit until completion of the Follow-up Visit.
6. For females of reproductive potential: Agrees not to donate ova (eggs) until at least 1 month after the last dose of Study Treatment.
7. Has demonstrated ≥80% compliance with self-administration of Study Treatment during the Run-in Period.
8. Is ambulatory and in good general physical and mental health as determined by the Investigator.
9. In the opinion of the Investigator, is able and willing to comply with the requirements of the protocol, including completing electronic versions of questionnaires, the Patient Voiding Diary, and the Urine Volume Diary (will require ability to collect, measure, and record voided volume by herself/himself using a graduated urine collection and measurement container [provided by the Sponsor, if needed]).

8.1.2 Exclusion Criteria

Urology Medical History
1. Patient has a history of 24-hour urine volume greater than 3,000 mL in the past 6 months, or a Urine Volume Diary day measurement greater than 3,000 mL during the Run-in Period.
2. Has lower urinary tract pathology that could, in the opinion of the Investigator, be responsible for urgency, frequency, or incontinence; including, but not limited to, urolithiasis, interstitial cystitis, prostate cancer, gastrointestinal (GI) cancer, tuberculosis, stone disease, urothelial tumor, prostatitis, and clinically relevant benign prostatic hypertrophy (BPH) or bladder outlet obstruction, as judged by the Investigator. Note: Male patients with mild to moderate BPH without evidence of bladder obstruction as determined by the Investigator may be included as long as they have been taking a medication for the treatment of BPH for at a least 1-year prior to Screening, with no change in dose of herbal medications, alpha antagonist medications or other symptomatic treatments or medications within 3 months prior to Screening, and no change in dose of 5 alpha reductase inhibitors within 6 months of Screening.

3. Has a history of surgery to correct stress urinary incontinence, pelvic organ prolapse, or procedural treatments for BPH within 6 months of Screening.

4. Has current history or evidence of Stage 2 or greater pelvic organ prolapse (prolapse extends beyond the hymenal ring).

5. Patient is currently using a pessary for the treatment of pelvic organ prolapse. 6. Has a known history of elevated post-void residual volume defined as greater than 150 mL.

7. Has undergone bladder training or electrostimulation within 28 days prior to Screening or plans to initiate either during the study.

8. Has an active or recurrent (>3 episodes per year) urinary tract infection by clinical symptoms or laboratory criteria (≥5 white blood cells [WBC] or a positive urine culture, defined as ≥105 colony forming units [CFU]/mL in 1 specimen). Patients diagnosed with a urinary tract infection (UTI) at the Screening Visit may be treated and re-screened once the infection has resolved.

9. Has a requirement for an indwelling catheter or intermittent catheterization.

10. Has received an intradetrusor injection of botulinum toxin within 9 months prior to Screening.

Other Medical History

11. Has uncontrolled hyperglycemia (defined as fasting blood glucose>150 mg/dL or 8.33 mmol/L and/or non-fasting blood glucose>200 mg/dL or 11.1 mmol/L) or, if in the opinion of the Investigator, is uncontrolled.

12. Has evidence of diabetes insipidus.

13. Is pregnant, breast-feeding, or is planning to conceive within the projected duration of the study.

14. Has a concurrent malignancy or history of any malignancy within 5 years prior to signing informed consent, except for adequately treated basal cell or squamous cell skin cancer or in situ cervical cancer.

15. Has uncontrolled hypertension (systolic blood pressure of ≥180 mmHg and/or diastolic blood pressure of ≥100 mmHg) or has a resting heart rate (by pulse)>100 beats per minute.

16. Patients who have systolic blood pressures≥160 mmHg but <180 mmHg are excluded, unless deemed by the Investigator and/or Medical Monitor as safe to proceed in this study and able to complete the study per protocol; these patients must be on stable hypertension medication for at least 90 days.

17. All patients with signs and symptoms of uncontrolled hypertension, regardless of blood pressure measurement, are excluded from the study. These include, but are not limited to neurological symptoms or findings, hematuria, proteinuria, retinopathy, unstable angina, and acute heart failure.

18. Has narrow angle glaucoma (primary open angle glaucoma is not excluded).

19. Has a history of cerebral vascular accident, transient ischemic attack, unstable angina, myocardial infarction, coronary artery interventions (e.g., coronary artery bypass grafting or percutaneous coronary interventions [e.g., angioplasty, stent insertion]), or neurovascular interventions (e.g., carotid artery stenting) within 6 months prior to the Screening Visit. Patients with these conditions should be on stable medical therapy for at least 3 months prior to the Screening Visit.

20. Has a known history of liver disease.

21. Has a history of injury, surgery, or neurodegenerative diseases (e.g., multiple sclerosis, Parkinson's) that could affect the lower urinary tract or its nerve supply.

8.2 Study Assessments And Procedures

The Investigator or qualified designee reviewed prior medication use, including any protocol-specified washout requirement, and recorded prior medication taken by the patient within 28 days prior to beginning completion of the Screening eDiary.

All medications for the treatment of OAB taken within 1 year of the Screening Visit were recorded. Medication history was assessed for male patients with history of mild to moderate BPH to ensure a stable treatment regimen that meets eligibility criteria.

Concomitant medications were reviewed and recorded at each study visit from Screening through Week 12 and at any Unscheduled Visits.

Male patients with mild to moderate BPH without evidence of bladder obstruction as determined by the Investigator could be included as long as they had been taking a medication for the treatment of BPH for at a least 1-year prior to Baseline, with no change in dose of herbal medications, alpha antagonist medications, or other symptomatic treatments or medications within 3 months prior to Baseline. To be eligible for the study, these BPH medication/s must have been stable from Screening until Baseline Visit.

Patients with a history of hypertension must have been on a stable blood pressure treatment regimen for 90 days prior to the Baseline Visit and must have been deemed by the Investigator and/or Medical Monitor as safe to proceed in this study and able to complete the study per protocol.

8.2.1 Post-Void Residual Volume

The risk of acute urinary retention or morbidities related to an increase in Post-Void Residual (PVR) is a concern with antimuscarinic therapy that promotes smooth muscle relaxation by inhibiting acetylcholine-induced smooth muscle contraction. If, during contraction, the bladder cannot generate enough pressure to overcome the outlet resistance in the urethra, either because of poor detrusor contractility or profound obstruction (most commonly from BPH), acute urinary retention or incomplete emptying of the bladder may result.

The volume of urine that remains in the bladder after voiding (PVR) is an objective measurement that may serve as a proxy for impaired ability to void.

PVR were performed via ultrasound at the visits indicated in the Schedule of Activities.

8.3 Statistical Analyses

For the analysis of the co-primary endpoints (change from baseline in average number of daily micturitions at Week 12 and change from baseline in average number of daily urge urinary incontinence episodes at Week 12, and placebo adjustment of each), a mixed model for repeated measure (MMRM) with restricted maximum likelihood estimation was used. This model corrects for dropout and accounts for the fact that measurements taken on the same patient over time tend to be correlated by using all available information on patients within the same covariate set to derive an estimate of the treatment effect for a dropout-free population. The analysis model for each efficacy endpoint includes terms for treatment, visit, OAB Type (Wet vs Dry), Sex (Female vs Male), Region (US vs Rest of World), baseline score, and interaction of visit by treatment.

Primary inferences were drawn from treatment differences for the changes from baseline derived from the MMRM models at Week 12. As part of secondary objectives, the treatment differences for each post baseline visit were also derived using the same MMRM model. The estimated treatment difference for at each visit was displayed in the summary of statistical analysis together with the 95% confidence interval and the associated p-value.

An unstructured covariance matrix was used to model the correlation among repeated measurements. The Kenward-Roger adjustment was used with restricted (or residual) maximum likelihood (REML) to make statistical inference. If the unstructured covariance model fails to converge with the default Newton-Raphson algorithm, the Fisher scoring algorithm or other appropriate methods can be used to provide initial values of the covariance parameters. In the rare event that none of the above methods yield convergence, a structured covariance would be used to model the correlation among repeated measurements.

The change from baseline efficacy endpoints was analyzed using the same MMRM model described for co-primary endpoints.

Analysis of the efficacy endpoints of proportion of patients with at least 75% reduction in the average number of daily UUI episodes at Week 12 and proportion of patients with 50% reduction in the average number of daily urgency episodes at Week 12 was analyzed using the Cochran-Mantel-Haenszel risk difference estimate. Missing Week 12 data was analyzed using multiple imputation. The estimated difference in the proportion of responders and 95% confidence interval for the difference was calculated using the Cochran-Mantel-Haenszel risk difference estimate stratified by OAB Type (Wet vs Dry) and Sex (Female vs Male), with weights proposed by Greenland and Robins.

The same statistical methods that were used to analyze the co-primary and secondary efficacy endpoints were used for the exploratory analyses. Exploratory responder analyses were analyzed using the same Cochran-Mantel-Haenszel model as described above for secondary endpoints.

Safety analyses were conducted using the SAF and summarized by treatment group as treated. The treatment-emergent period is defined as the period of time from the first dose date of the double blinded Study Treatment through 28 days after the last dose of Study Treatment, or the date of initiation of another investigational agent or surgical intervention or rollover to the extension study, whichever occurs first. Safety was assessed through summaries of adverse events, the frequency of treatment discontinuations due to adverse events, and clinical laboratory evaluations.

The results or effects reported herein should be understood as being statistically significant based on the statistical analysis described above. The level of statistical significance can be, for example, of at least p<0.05, of at least p<0.01, of at least p<0.005, or of at least p<0.001. When a measurable result or effect is expressed or identified herein, it will be understood that the result or effect can be evaluated based upon its statistical significance relative to a baseline, typically placebo based.

8.4 Clinical Trial Data and Results

In this study, once-daily vibegron 75 mg demonstrated significantly better efficacy compared with placebo across three key secondary endpoints (as well as two co-primary endpoints), indicating further benefit of vibegron for patients with UUI and total incontinence episodes (see Table 21).

TABLE 21

Week 12 LS Mean Change from Baseline (Placebo-Adjusted)

| Endpoint | Vibegron | n | p-value | Tolterodine | n | p-value |
|---|---|---|---|---|---|---|
| UUI Episodes[1] | −0.6 | 383 | <0.0001 | −0.4 | 286 | 0.0123 |
| Micturitions[1] | −0.5 | 492 | <0.001 | −0.3 | 378 | 0.0988 |
| Urgency Episodes[2] | −0.7 | 492 | 0.0020 | −0.4 | 378 | 0.0648 |
| Total Incontinence Episodes[2] | −0.7 | 383 | <0.0001 | −0.5 | 286 | 0.0074 |
| Volume Voided (ml)[2] | 21.2 | 490 | <0.0001 | 13.3 | 375 | <0.001 |
| OAB-q Coping Score[2] | 3.6 | 512 | 0.0038 | 3.1 | 401 | 0.0212 |

[1]Co-primary endpoint; [2]Key Secondary Endpoint; LS = Least Squares.

Vibegron 75 mg demonstrated statistically significantly reductions in total incontinence by week 2 and maintained this significance throughout the 12-week treatment period. Vibegron 75 mg demonstrated a clear increase in volume voided per micturition, a relatively objective measure increasing bladder capacity. Total incontinence episodes were reduced by half in the vibegron group vs baseline, and almost half of vibegron-treated patients with UUI at baseline had at least 75% reductions in UUI episodes after 12 weeks of vibegron therapy. Vibegron tolerability was favorable, with very few adverse events>2% and greater than placebo.

Changes in daily urge urinary incontinence (UUI) episodes for all subjects and for men with and without a medical history of BPH are shown in Table 22.

TABLE 22

UUI: Overall and by Subgroup (Descriptive Statistics: Week 12 CFB Mean (Q1,Q3))

| Subgroup | Placebo Mean (Q1,Q3) | n | Vibegron Mean (Q1,Q3) | n | Tolterodine Mean (Q1,Q3) | n |
|---|---|---|---|---|---|---|
| Overall | −1.46 (−0.21, −0.29) | 372 | −2.01 (−3.00, −0.60) | 383 | −1.75 (−2.43, −0.71) | 286 |
| Males with BPH | −1.05 (−1.29, −0.71) | 8 | −1.09 (−1.57, −0.08) | 16 | −2.15 (−2.71, −1.36) | 9 |
| Males without BPH | −1.71 (−2.71, −0.43) | 30 | −1.51 (−2.25, −0.33) | 26 | −2.05 (−2.29, −0.93) | 24 |

Changes in micturitions for all subjects and for men with and without a medical history of BPH are shown in Table 23. Descriptive statistics are shown in Table 24.

TABLE 23

Micturitions: Overall and by Subgroup (Descriptive Statistics: Week 12 CFB Mean (Q1, Q3)

| Subgroup | Placebo Mean (Q1, Q3) | n | Vibegron Mean (Q1, Q3) | n | Tolterodine Mean (Q1, Q3) | n |
|---|---|---|---|---|---|---|
| Overall | −1.62 (−2.89, 0.14) | 475 | −2.04 (03.43, −0.57) | 492 | −1.78 (−3.14, −0.29) | 378 |
| Males with BPH | −0.68 (−2.29, 0.43) | 15 | −1.50 (−2.90, −0.14) | 29 | −1.25 (−2.29, 0.29) | 21 |
| Males without BPH | −1.60 (−2.29, 0.29) | 54 | −2.26 (−3.43, −0.57) | 46 | −1.29 (−3.13, 0.29) | 39 |

TABLE 24

Micturitions: Males With and Without BPH (Descriptive Statistics)

| Subgroup | Visit | Placebo | n | Vibegron | n | Tolterodine | n |
|---|---|---|---|---|---|---|---|
| Overall for Males | Baseline Mean (Q1, Q3) | 11.95 (9.71, 13.14) | 75 | 11.79 (9.14, 12.86) | 77 | 12.12 (9.14, 13.43) | 65 |
| | Week 12 CFB Mean (Q1, Q3) | −1.40 (−2.29, 0.29) | 69 | −1.97 (−3.43, −0.38) | 75 | −1.28 (−2.99, 0.29) | 60 |
| Males with BPH | Baseline Mean (Q1, Q3) | 11.45 (9.79, 12.21) | 15 | 11.22 (8.83, 12.14) | 29 | 12.65 (10.00, 14.29) | 21 |
| | Week 12 CFB Mean (Q1, Q3) | −0.68 (−2.29, 0.43) | 16 | −1.50 (−2.90, −0.14) | 16 | −1.25 (−2.29, 0.29) | 9 |
| Males without BPH | Baseline Mean (Q1, Q3) | 12.09 (9.67, 13.29) | 59 | 12.14 (9.36, 14.39) | 48 | 11.84 (9.14, 13.29) | 43 |
| | Week 12 CFB Mean (Q1, Q3) | −1.60 (−2.29, 0.29) | 54 | −2.26 (−3.43, −0.57) | 46 | −1.29 (−3.13, 0.29) | 39 |

Data on reduction in urgency episodes are shown for all subjects and for men with and without a medical history of BPH in Table 25.

TABLE 25

Urgency Episodes: Overall and by Subgroup
(Descriptive Statistics: Week 12 CFB Mean (Q1, Q3))

| Subgroup | Placebo Mean (Q1, Q3) | n | Vibegron Mean (Q1, Q3) | n | Tolterodine Mean (Q1, Q3) | n |
|---|---|---|---|---|---|---|
| Overall | −2.26 (−4.00, −0.29) | 475 | −2.93 (−4.71, −0.65) | 492 | −2.57 (−4.17, −0.57) | 378 |
| Males with BPH | −2.43 (−4.29, −0.0) | 15 | −1.90 (−4.71, 0.10) | 29 | −3.29 (−5.14, 0.31) | 21 |
| Males without BPH | −2.38 (−3.84, −0.40) | 54 | −2.56 (−3.71, 0.24) | 46 | −2.32 (−4.29, −0.04) | 39 |

In addition, the data on the Post Void Residual Urine Volume (PVR) in all males and males with a medical history of BPH is shown in Tables 26 and 27, respectively.

TABLE 26

Change in Post Void Residual Urine Volume (PVR) in All Males from Baseline to Week 12

| PVR (mL) in Males | Placebo N = 81 | Vibegron N = 82 | Tolterodine N = 66 |
|---|---|---|---|
| Mean Baseline (SD)* | 27.8 (29.47) | 38.8 (37.20) | 31.5 (33.00) |
| Mean Change from Baseline at Week 12 (SD) | 13.1 (43.63) | 2.2 (48.45) | 10.2 (44.24) |
| PVR Categories at Week 12 | | | |
| <100 mL | 92.0% | 89.7% | 85.2% |
| ≥100 mL to <200 mL | 6.7% | 7.7% | 11.5% |
| ≥200 mL to <350 mL | 1.3% | 2.6% | 3.3% |
| ≥350 mL | 0 | 0 | 0 |

Note
that the protocol required the baseline PVR to be below 150 mL
*n's for each treatment group at baseline are 80, 82 and 66 patients for placebo, vibegron and tolterodine, respectively.

TABLE 27

Change in Post Void Residual Urine Volume (PVR) in Males with Medical History of BPH from Baseline to Week 12

| PVR (mL) in Males with BPH | Placebo N = 17 | Vibegron N = 29 | Tolterodine N = 22 |
|---|---|---|---|
| Mean Baseline (SD) | 27.3 (26.73) | 35.3 (33.57) | 41.0 (43.17) |
| Mean Change from Baseline at Week 12 (SD) | 28.6 (62.36) | −3.4 (42.45) | 3.7 (50.64) |
| PVR Categories at Week 12 | | | |
| <100 mL | 82.4% | 96.6% | 71.4% |
| ≥100 mL to <200 mL | 11.8% | 0 | 28.6% |
| ≥200 mL to <350 mL | 5.9% | 3.4% | 0 |
| ≥350 mL | 0 | 0 | 0 |

Note
that the protocol required the baseline PVR to be below 150 mL

By comparison, the PVR in the study population as a whole is shown in Table 28.

TABLE 28

Change in Post Void Residual Urine Volume (PVR)

| PVR (mL) | Placebo N = 540 | Vibegron N = 545 | Tolterodine N = 430 |
|---|---|---|---|
| Mean Baseline (SD)* | 27.1 (31.05) | 28.8 (32.49) | 27.9 (37.94) |
| Mean Change from Baseline at Week 12 (SD) | 2.1 (37.25) | 0.4 (38.27) | 3.1 (40.93) |
| PVR Categories at Week 12 | | | |
| <100 mL | 89.1% | 89.9% | 86.5% |
| ≥100 mL to <200 mL | 3.7% | 3.5% | 5.8% |
| ≥200 mL to <350 mL | 0.6% | 0.6% | 0.7% |
| ≥350 mL | 0 | 0 | 0 |

Note:
the phrotocol required the baseline PVR to be below 150 mL
*n's for each treatment group at baseline are 539, 544 and 430 for placebo, vibegron and tolterodine, respectively

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating at least one overactive bladder symptom in a human male subject in need thereof, the method comprising orally administering to the subject an amount of from about 60 mg to about 90 mg of vibegron per day, wherein the subject is on pharmacological therapy for benign prostatic hyperplasia.

2. The method of claim 1, wherein the at least one overactive bladder symptom is selected from the group consisting of urge urinary incontinence, urgency, urinary frequency, nocturia, and a combination thereof.

3. The method of claim 1, wherein the at least one overactive bladder symptom is urge urinary incontinence, urgency, and urinary frequency.

4. The method of claim 1, wherein the subject is over the age of 45 years.

5. The method of claim 1, wherein the pharmacological therapy for benign prostatic hyperplasia is a 5-alpha reductase inhibitor.

6. The method of claim 1, wherein the pharmacological therapy for benign prostatic hyperplasia is an alpha blocker.

7. The method of claim 1, wherein the pharmacological therapy for benign prostatic hyperplasia is a combination of a 5-alpha reductase inhibitor and an alpha blocker.

8. The method of claim 1, wherein vibegron is administered once per day.

9. The method of claim 1, wherein the amount of vibegron is about 75 mg.

10. The method of claim 9, wherein vibegron is administered once per day.

11. The method of claim 9, wherein the at least one symptom is selected from the group consisting of urge urinary incontinence, urgency, urinary frequency, nocturia, and a combination thereof.

12. The method of claim 9, wherein the pharmacological therapy for benign prostatic hyperplasia is a 5-alpha reductase inhibitor.

13. The method of claim 9, wherein the pharmacological therapy for benign prostatic hyperplasia is an alpha blocker.

14. The method of claim 9, wherein the pharmacological therapy for benign prostatic hyperplasia is a combination of a 5-alpha reductase inhibitor and an alpha blocker.

15. The method of claim 9, wherein the method is to provide a change from baseline in average number of micturitions per 24 hours of from about −1.4 to about −2.5, and/or at least a 30% reduction from baseline in urgency episodes per day, and/or a change from baseline in an average number of nocturia episodes per night of from about −0.2 to about −0.4 greater than a change from baseline for a placebo treatment.

16. The method of claim 9, wherein the method is to provide a change from baseline in post void residual urine volume of from about 10 mL to about-20 mL.

17. A method of decreasing micturitions in a human male subject in need thereof, the method comprising orally administering to the subject an amount of from about 60 mg to about 90 mg of vibegron per day, wherein the subject is on pharmacological therapy for benign prostatic hyperplasia.

18. The method of claim 17, wherein the amount of vibegron is about 75 mg.

19. A method of treating overactive bladder symptoms in a human male subject in need thereof, the method comprising orally administering to the subject about 75 mg of vibegron per day, wherein the symptoms comprise urge urinary incontinence, urgency, and urinary frequency, wherein the subject is on pharmacological therapy for benign prostatic hyperplasia.

20. The method of claim 19, wherein the symptoms further comprise nocturia.

21. The method of claim 19, wherein the pharmacological therapy for benign prostatic hyperplasia is a 5-alpha reductase inhibitor.

22. The method of claim 19, wherein the pharmacological therapy for benign prostatic hyperplasia is an alpha blocker.

23. The method of claim 19, wherein the pharmacological therapy for benign prostatic hyperplasia is a combination of a 5-alpha reductase inhibitor and an alpha blocker.

24. The method of claim 19, wherein the method is to provide at least a 30% reduction from baseline in urgency episodes per day, and/or at least a 30% increase from baseline in an average volume voided per micturition, and/or a change from baseline in an average number of nocturia episodes per night of from about −0.2 to about −0.4 greater than a change from baseline for a placebo treatment.

25. The method of claim 19, wherein the method is to provide a change from baseline in post void residual urine volume of from about 10 mL to about-20 mL.

26. A method of treating at least one overactive bladder symptom in a human male subject in need thereof, the method comprising orally administering to the subject about 75 mg of vibegron per day, wherein the subject is on pharmacological therapy for benign prostatic hyperplasia and wherein the subject does not experience a substantial change in post void residual volume.

27. The method of claim 26, wherein the at least one overactive bladder symptom is selected from the group consisting of urge urinary incontinence, urgency, urinary frequency, nocturia, and a combination thereof.

28. The method of claim 26, wherein the method is to provide a change from baseline in post void residual urine volume of about 10 mL or less.

29. The method of claim 10, wherein steady state concentrations are achieved within 7 days.

* * * * *

UNITED STATES PATENT AND TRADEMARK OFFICE
CERTIFICATE OF CORRECTION

| | | |
|---|---|---|
| PATENT NO. | : 12,357,636 B2 | Page 1 of 1 |
| APPLICATION NO. | : 17/311239 | |
| DATED | : July 15, 2025 | |
| INVENTOR(S) | : Mudd, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 944 days.

Signed and Sealed this
Sixteenth Day of December, 2025

John A. Squires
*Director of the United States Patent and Trademark Office*